United States Patent [19]

Pahno et al.

[11] Patent Number: 5,269,030
[45] Date of Patent: Dec. 14, 1993

[54] APPARATUS AND METHOD FOR MANAGING WASTE FROM PATIENT CARE, MAINTENANCE, AND TREATMENT

[75] Inventors: Demetrios A. Pahno, Mt. Pleasant; James R. Stolpmann, Charleston; James M. C. Thomas, Mt. Pleasant; David N. Ashcraft; Michael V. Bolden, both of Charleston; Roger D. Dalton, Ladson; James J. Romano, Charleston; Kenneth R. Smith, Charleston; Timothy R. Trauernicht, Charleston, all of S.C.

[73] Assignee: SSI Medical Services, Inc., Charleston, S.C.

[21] Appl. No.: 792,216

[22] Filed: Nov. 13, 1991

[51] Int. Cl.⁵ ............................................ A61G 7/02
[52] U.S. Cl. ........................................ 5/604; 5/914; 5/453; 5/455; 5/468; 4/615; 4/480; 4/482
[58] Field of Search ................ 5/604, 606, 450, 453, 5/455, 461, 463, 468, 469, 503.1, 910, 914, 928, 484; 4/450, 453–457, 480, 482, 615, 616

[56] References Cited

U.S. PATENT DOCUMENTS

| | | | |
|---|---|---|---|
| Re. 28,405 | 5/1975 | Sollerud | 4/616 |
| D. 281,535 | 11/1985 | Atkinson et al. | |
| 2,656,549 | 10/1953 | Osbon, Jr. | 5/463 |
| 2,761,149 | 9/1956 | Kay | 4/450 X |
| 3,014,224 | 12/1961 | Hall | |
| 3,129,438 | 4/1964 | Hall | |
| 3,503,083 | 3/1970 | Barnett | |
| 3,562,824 | 2/1971 | White | |
| 3,605,145 | 9/1971 | Graebe | |
| 3,757,355 | 9/1973 | Allen et al. | 5/604 |
| 3,757,356 | 9/1973 | Freeman | |
| 3,805,305 | 4/1974 | Lunblad | 5/616 |
| 3,870,450 | 3/1975 | Graebe | |
| 3,919,730 | 11/1975 | Regan | |
| 4,005,236 | 1/1977 | Graebe | |
| 4,054,959 | 10/1977 | DiMatteo et al. | |
| 4,085,471 | 4/1978 | DiMatteo et al. | |
| 4,085,472 | 4/1978 | DiMatteo | |
| 4,258,445 | 3/1981 | Zur | |
| 4,483,030 | 11/1984 | Flick et al. | |
| 4,541,136 | 9/1985 | Graebe | |

(List continued on next page.)

Primary Examiner—Michael F. Trettel
Attorney, Agent, or Firm—Dority & Manning

[57] ABSTRACT

An apparatus and method for managing waste from patient care, maintenance, and/or treatment includes an inflatable bladder member disposed to support at least a first portion of the body of the patient. A flexible basin member is fitted over the bladder and receives waste materials, and a filter sheet is disposed atop the basin member. The basin member is connected to a holding reservoir and a vacuum blower. A liquid waste pump is connected to the holding reservoir to transfer liquid waste to a waste jug. A vacuum wand provides rinsing liquid from a rinse liquid jug via a rinse liquid pump and provides suction via the vacuum blower. Liquid levels in each of the rinse liquid jug, the waste jug, and the holding reservoir, are monitored by liquid level sensing devices which supply signals to a microprocessor which controls various functions of the apparatus. Special inflatable sacks are provided to assist turning the patient to facilitate cleansing of the patient. Inflatable cushions receive the inflatable bladder member and dispose it to become coextensive with the support of the rest of the patient in a patient support apparatus, if desired.

72 Claims, 18 Drawing Sheets

U.S. PATENT DOCUMENTS

| | | | |
|---|---|---|---|
| 4,542,547 | 9/1985 | Sato . | |
| 4,561,431 | 12/1985 | Atkinson . | |
| 4,620,333 | 11/1986 | Ritter | 5/606 X |
| 4,631,762 | 12/1986 | Fugett . | |
| 4,635,621 | 1/1987 | Atkinson . | |
| 4,662,012 | 5/1987 | Torbet . | |
| 4,692,140 | 9/1987 | Olson . | |
| 4,698,864 | 10/1987 | Graebe . | |
| 4,722,105 | 2/1988 | Douglas . | |
| 4,745,647 | 5/1988 | Goodwin . | |
| 4,754,508 | 7/1988 | Nishiguchi . | |
| 4,768,249 | 9/1988 | Goodwin . | |
| 4,800,599 | 1/1989 | Korchinski et al. . | |
| 4,805,249 | 2/1989 | Usman et al. . | |
| 4,821,348 | 4/1989 | Pauna . | |
| 4,821,350 | 4/1989 | Feldt . | |
| 4,864,671 | 9/1989 | Evans . | |
| 4,870,710 | 10/1989 | Hartmann | 5/606 |
| 4,914,760 | 4/1990 | Hargest et al. . | |
| 4,942,635 | 7/1990 | Hargest et al. . | |
| 4,949,413 | 8/1990 | Goodwin . | |
| 4,949,414 | 8/1990 | Thomas et al. . | |
| 4,965,900 | 10/1990 | Smith . | |
| 4,989,280 | 2/1991 | Bair . | |
| 5,001,790 | 3/1991 | Kuhn . | |
| 5,003,654 | 4/1991 | Vrzalik . | |
| 5,023,967 | 6/1991 | Ferrand . | |
| 5,035,014 | 7/1991 | Blanchard . | |
| 5,051,673 | 9/1991 | Goodwin . | |
| 5,058,222 | 10/1991 | Workman et al. | 4/480 X |
| 5,077,845 | 1/1992 | Tokunaga et al. | 5/403 X |

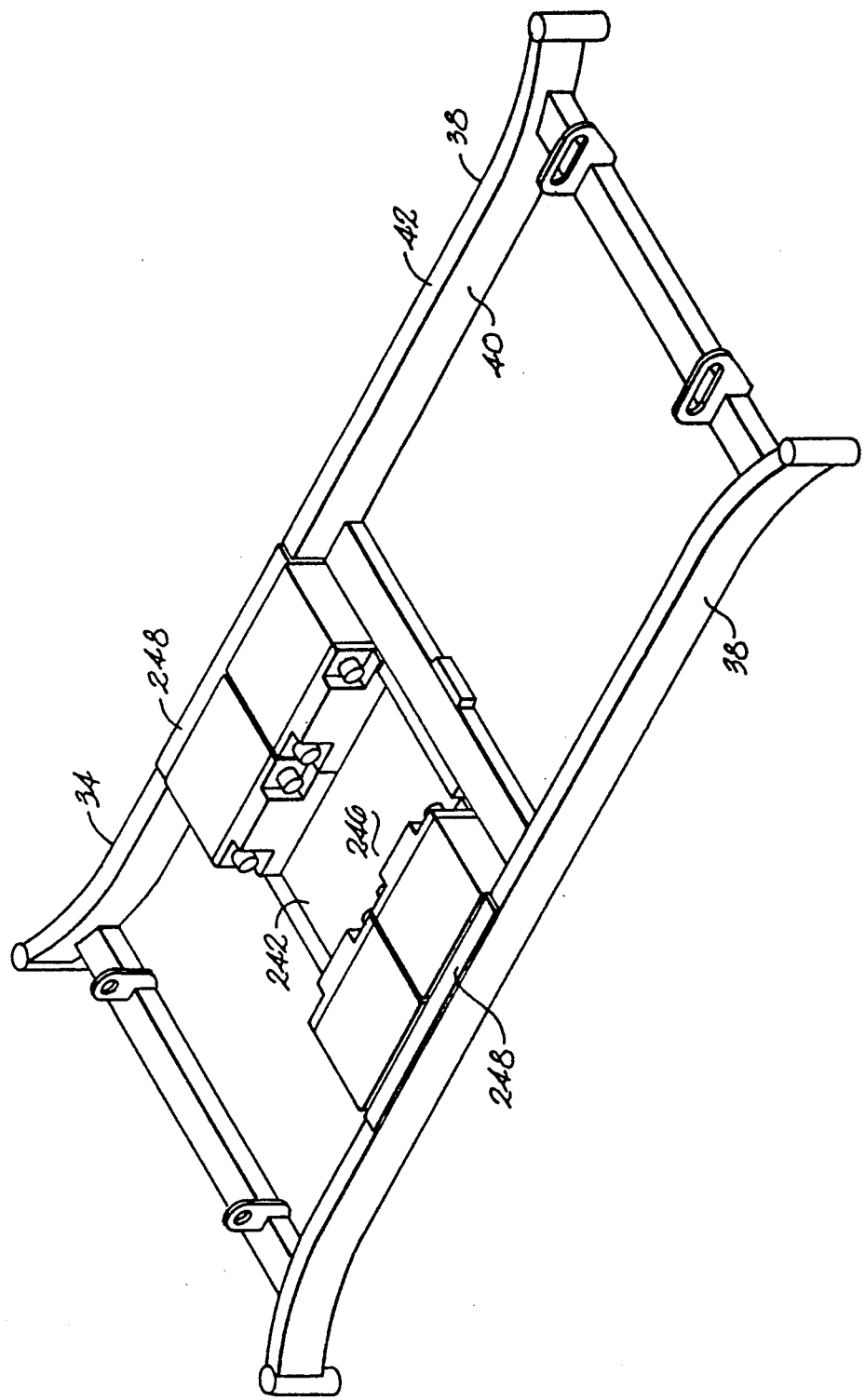

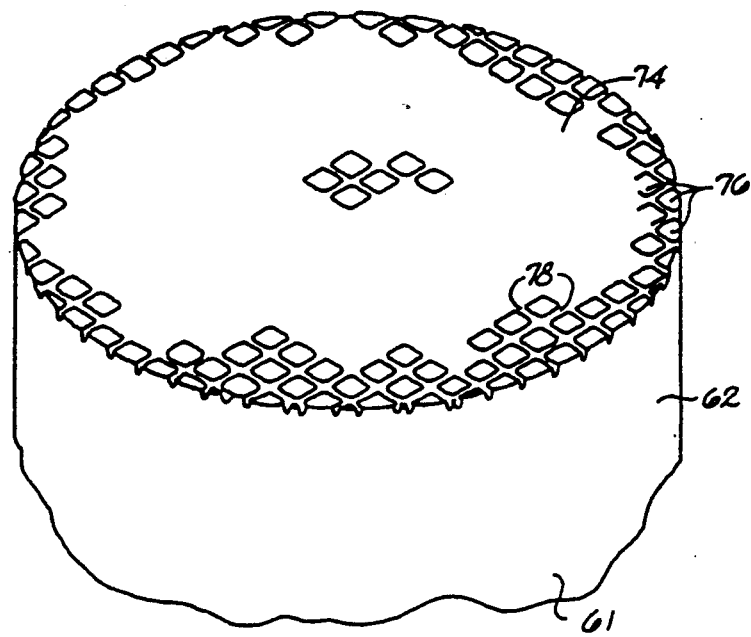
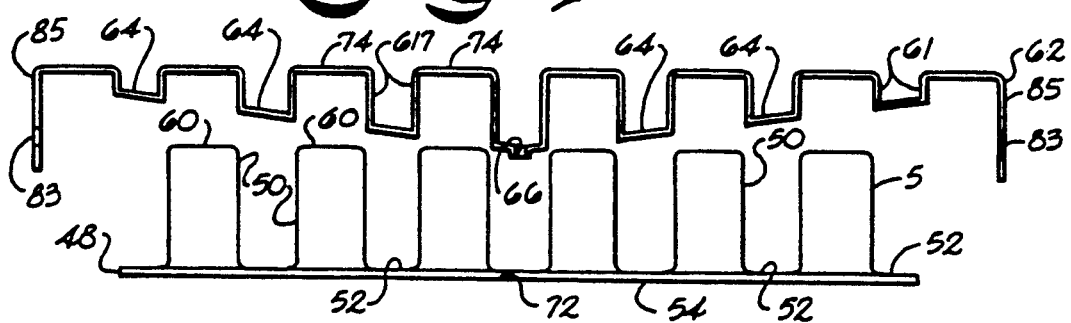
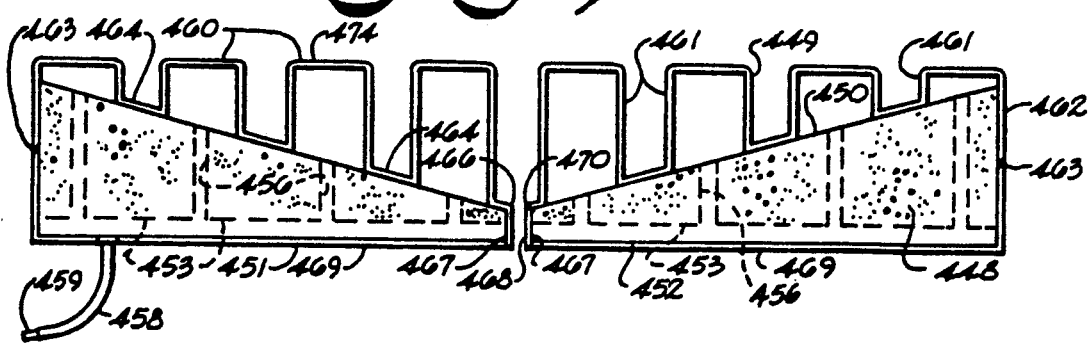

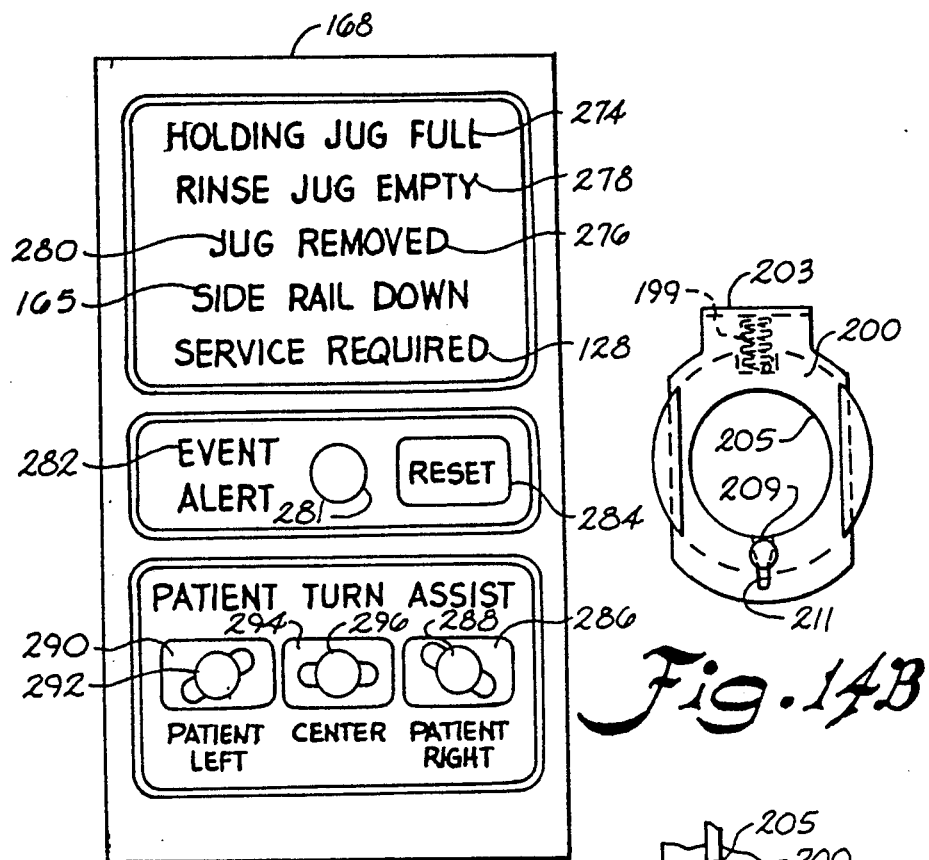
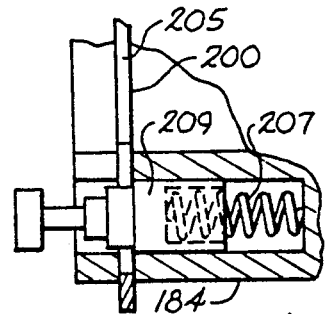
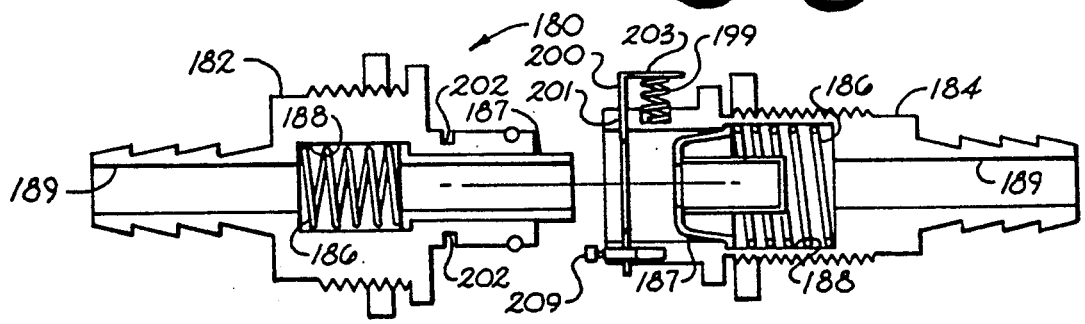

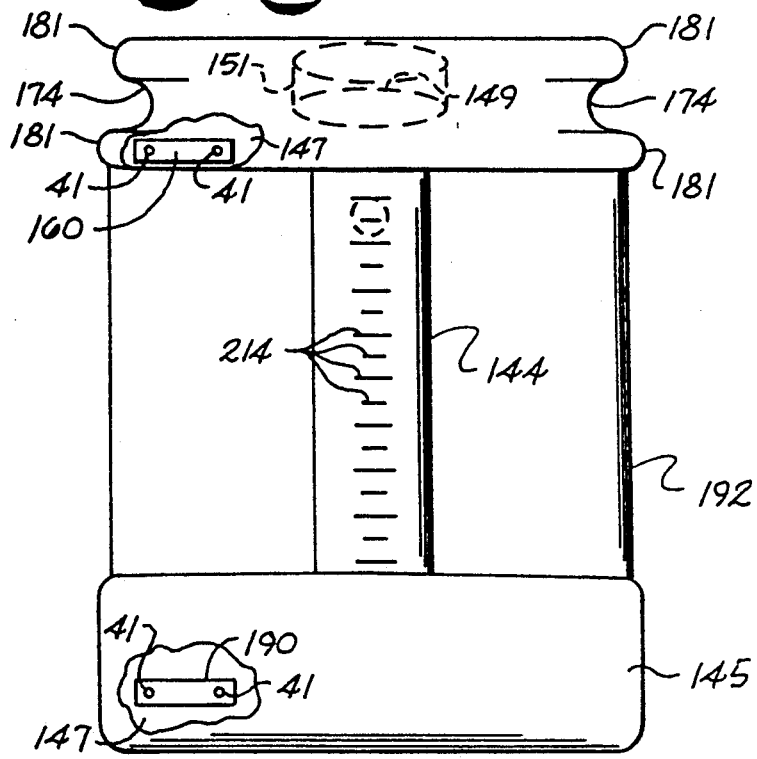
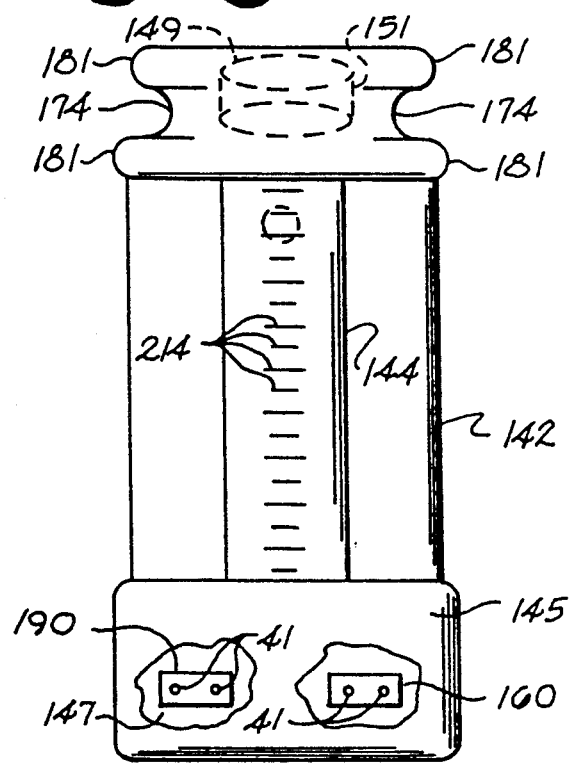

APPARATUS AND METHOD FOR MANAGING WASTE FROM PATIENT CARE, MAINTENANCE, AND TREATMENT

BACKGROUND OF THE INVENTION

The present invention relates to apparatuses and methods for managing liquid wastes associated with patients confined to a hospital bed, wheelchair, treatment table or the like.

The management of incontinence of a patient is an especially burdensome chore. A large number of patients are unable to control their bowels and bladders or are sufficiently incapacitated that they are unable to transport themselves to conventional toilet facilities when the need arises. When such patients suffer an episode of bowel and/or bladder incontinence, they may be subjected to a relatively prolonged period of time contacting the waste products so produced. In addition to being socially unacceptable for the patient, the waste products can cause skin maceration and breakdown. Moreover, cleaning the patient and the bedding pose especially undesirable chores for the nursing staff and thus adversely affect nursing morale. Moreover, each episode can require up to 20 to 40 minutes of nursing time to clean up a single patient who has suffered an incontinence event. For some patients, up to 40% of nursing time devoted to such patient is devoted to clean up activities associated with incontinence events. In addition, a single nurse is often incapable of turning the patient to the degree needed for adequate cleansing of the patient after an incontinence event. Thus, more than one member of the nursing staff must be involved in the clean up chore.

One method currently employed to manage bladder incontinence is to catheterize the patient. This method does not require any positive effort or cooperation of the patient. However, in-dwelling catheters often cause infection which is one of the leading causes of death in older patients who have been so catheterized.

Devices such as disclosed in U.S. Pat. No. 4,631,762 to Fugett, require the patient to be aware that an incontinence event is imminent and further require the patient to be able to indicate same to the nursing staff or to take action to activate the device to assume a configuration ready to accommodate an incontinence event. For example, the Fugett device requires a section of the mattress to be removed and a toilet seat to be raised flush with the level of the mattress. Other devices which require reconfiguration before they are ready to accommodate an incontinence event, are disclosed in U.S. Pat. Nos. 3,014,224 to Hall; 3,129,438 to Hall: 3,503,083 to Barnett; 3,562,824 to White: 4,054,959 and 4,085,471 to DiMatteo et al: 4,258,445 to Zur; 4,821,348 to Pauna: 4,754,508 to Nishiouchi: 4,800,599 to Korchinski et al; 4,805,249 to Usman et al; and 5,001,790 to Kuhn. Moreover, such devices can require significant moving about of the patient. Such movement is particularly undesirable for certain types of patients, for example those with sensitive skin conditions like decubitus ulcers. Furthermore, such devices are not readily adaptable to certain types of patient supports such as low air loss beds like the ones disclosed in U.S. Pat. Nos. 4,745,647 to Goodwin, 4,949,414 to Thomas et al. and 5,003,654 to Vrzalik because of the extensive pneumatic "plumbing" which exists beneath the main horizontal weight-bearing support structures forming such beds.

A device such as disclosed in U.S. Pat. No. 5,023,967 to Ferrand contains inflatable support cushions with a large opening 540 (FIGS. 58 and 60) formed in the region of the cushions disposed to receive the excretory organs of the patient so that any excreted wastes fall into the opening. However, such devices severely restrict movement of the patient in a manner that would misalign the patient's excretory organs with the opening in the cushions. Moreover, such devices fail to support the patient's backside in a manner sufficient for the patient's comfort.

Other devices such as disclosed in U.S. Pat. Nos. 3,757,356 to Freeman and 5,001,790 to Kuhn rest atop the normal support surface of the bed and thus involve all of the discomforting drawbacks of an uneven support surface.

Still other devices such as disclosed in U.S. Pat. No. 4,965,900 to Smith present several drawbacks, not the least of which is the failure to address the odor problem and the failure to signal the staff of the occurrence of an incontinence event by any means other than the malodor arising long after the event. Moreover, such devices fail to deal effectively with solid waste.

OBJECTS AND SUMMARY OF THE INVENTION

It is a principal object of the present invention to provide a pressure-relieving waste management system that supports the weight of the patient at interface pressures less than 32 millimeters of mercury at all patient and bed position attitudes and with reduced shear when the head of the bed is articulated at an incline to the horizontal.

It is a further principal object of the present invention to provide a waste management system for urinary and fecal incontinence events and other liquid wastes associated with patient care and treatment, wherein the system can be retrofitted as a modular add-on component to an existing articulatable low air loss patient support system.

Another principal object of the present invention is to provide an incontinence management system that combines the attributes of being easy to use, technically advanced, superior to current methods, conserving nursing staff time and disposable materials, and eliminating the need for vigilance or cooperation by either the patient or the nursing staff prior to the incontinence event.

Still another principal object of the present invention is to provide an apparatus and method that manages wastes associated with patient care wherein the cooperation and/or effort of the patient is not required to render the apparatus and/or method effective to manage bowel and/or bladder incontinence of the patient.

An additional principal object of the present invention is to provide a waste management system that collects wastes associated with patient care and patient treatment wherein the inventive system facilitates containment, ease of clean up, and disposal of such wastes.

A yet additional principal object of the present invention is to provide an incontinence management system that collects urine and fecal matter in a manner which facilitates containment, ease of clean up, and disposal of such wastes.

A further principal object of the present invention is to provide a liquid waste management system that keeps the patient drier and cleaner than conventional technologies.

Still a further principal object of the present invention is to provide an incontinence management system that reduces the time and effort that nurses spend managing each patient incontinence event.

Another principal object of the present invention is to provide an incontinence management system that enhances patient care with means for assisting in turning the patient to either of the patient's sides wherein the effort of two hospital staff members is not required.

Yet a further principal object of the present invention is to provide an incontinence management system that reduces the cost associated with management of patient incontinence.

Yet another principal object of the present invention is to provide an incontinence management system that reduces the amount of supplies used per incontinence event.

Still another principal object of the present invention is to provide an incontinence management system that includes a non-abrasive skin cleansing technique to reduce or prevent further damage to patients' tissues during clean-up after an incontinence event.

A further principal object of the present invention is to provide an incontinence management system that eliminates the need for invasive catheterization for those patients not requiring urine output measurements or for those patients for which it is acceptable to net out total waste fluids from rinse fluids.

Yet another principal object of the present invention is to provide an incontinence management system that controls odors associated with incontinence events.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, the apparatus for managing waste associated with the care, maintenance and/or treatment of a patient, whether from incontinence, bathing, or control of liquids during patient treatment, comprises a means for supporting at least a portion of the patient's body. The means for supporting a portion of the patient's body desirably enables the portion of the patient's body to be supported in a pressure-relieving manner and typically at a level that is coextensive with any support surface of any patient support apparatus that may be used to support other portions of the patient's body. Accordingly, the means for supporting a portion of the patient's body desirably defines a surface which is at substantially the same height as the support surface of any patient support surface being used in conjunction with the apparatus of the present invention. For example, if a patient support surface is defined by the upper surfaces of inflatable sacks of a low air loss bed, the means for supporting a portion of the patient's body desirably supports this portion of the patient's body coplanar with the support surfaces of the patient support apparatus.

As embodied herein, the means for supporting a portion of the patient's body includes a support member. The support member can be provided in the form of an inflatable bladder which defines a gas tight enclosure configured to contain pressurized air. An alternative embodiment of the support member can include a support cushion formed of polyurethane open-cell foam, which is configured identically to the support bladder. The support member desirably defines a plurality of cylindrical fingers which rise vertically above the floor of the support member. The transverse cross-sectional shape of each finger can be circular or can be a polygonal shape. The free end of each finger defines a patient support surface disposed to support the weight of the portion of the body of the occupant of the apparatus of the present invention. The plurality of fingers can be arrayed in a regular pattern in which the pressure exerted on the body of the patient amounts to less than the typical capillary closure threshold pressure of 32 millimeters of mercury. The ratio of the support area of each finger versus the area of the gap between the fingers is desirably greater than one. The height of each finger must be tall enough to accommodate deformation that would maintain the heaviest part of the patient's body in the neutral plane. However, the height of each finger should not be so tall relative to the transverse cross-sectional area of each finger, that the finger becomes unstable.

In accordance with the present invention, means can be provided for catching the waste from an incontinence event, bathing, or other treatment of the patient whose body is supported, at least as to one portion of the patient's body, in the means for supporting the portion of the patient's body. The catching means desirably is supported by the means for supporting the portion of the patient's body and desirably is supported between that portion of the patient's body and the means for supporting same. As embodied herein, the catching means desirably includes a basin member which is configured to conform snugly to the configuration of at least the free ends of the support fingers of the support member. The basin member is formed of material that is flexible enough so that the basin member offers no substantial impediment to collapsing into a flat surface when the support member collapses. The material forming the basin member desirably is liquid impermeable, such as very flexible elastomer having a thickness of about 20 mils. Antimicrobial properties desirably are provided in the material forming the basin member. The upper surface of the basin member desirably is formed of or coated with a layer of hydrophobic material which assists in assuring gravity drainage of liquid waste. The basin member includes a floor that is disposed beneath the level of the support surfaces of the support fingers. The floor of the basin member desirably slopes toward at least one drain opening defined through the floor of the basin member. Thus, the floor of the basin member is desirably configured with a constantly declining height gradient as one proceeds from the peripheral portion of the basin member toward the drain opening. The drain opening of the basin member desirably is connected via a waste removal conduit to a drain fitting that inserts through a centrally located opening defined through the base portion of the support member.

The basin member also defines a plurality of grid configurations. Each grid configuration is disposed in one of the portions of the basin member that is located above one of the support surfaces of one of the support fingers of the support member. Each grid configuration defines a local exterior topography formed of a plurality of slightly raised portions separated from one another by recessed channel portions. While the raised portions may be providing support to the body of the patient, the channel portions assure rapid liquid drainage away from the body of the patient.

In further accordance with the present invention, the catching means can include a liquid permeable filter sheet that is disposed to be carried above the basin member and closer to the patient's body than the basin member. As embodied herein, the liquid permeable filter sheet is disposed to be carried atop the basin member by the grid configuration sections and constitutes a section of the catching means that is permeable to liquids. The filter sheet is configured to trap larger solid waste material and acts as a filter to prevent these larger particulates from clogging the basin member and a waste removal conduit (described hereafter), which desirably is connected to the drain opening of the basin member. The filter sheet desirably defines a fabric, such as a flexible screen, having a plurality of small individual pores. The filter sheet desirably should be formed of material that is antimicrobial, hypoallergenic, flame retardant, sufficiently hydrophobic so as to dry quickly, odor resistant, bacteriostatic, and non-staining for repeated use in an environment that anticipates staining from urine, fecal matter, and fluids normally found and used in the hospital environment. In addition, the material forming the filter sheet should have a very high tensile strength that is at least equal to the tensile strength of current hospital draw sheets and have a very small coefficient of friction to facilitate use of the filter sheet as a draw sheet. The filter sheet desirably has reinforced edges forming a continuous border around the portion containing the small pores and can be provided with handles or grip openings secured to the border portions.

In further accordance with the present invention, a means can be provided for detachably securing the filter sheet against movement away from a position resting over the basin member. As embodied herein, the filter sheet's detachably securing means desirably includes a plurality of fastening means in the form of snaps that are mateable with other snaps mounted on the exterior surfaces of side panels. The side panels are themselves attached to the free endwall surfaces of an adaptor shell that is described hereafter. The fastening end of the filter sheet snaps desirably can be exposed for service on the surface of the border portions of the filter sheet. The inside surfaces of the side panels can be provided with a plurality of other snaps which are detachably attachable to a plurality of mating snaps (described hereafter) of air inflated cushions (described hereafter) and thus hold the filter sheet in place yet permit disengagement of the filter sheet by grasping the handles and pulling away from the adapter shell whenever the use of the filter sheet as a draw sheet is desired.

In further accordance with the present invention, means can be provided for removing the waste materials that are caught by the catching means. As embodied herein, the waste removing means desirably includes at least one waste removal conduit that is configured to be connected in communication with at least one drain opening of the basin member. Desirably, a drain fitting extends through the drain opening and is connected to the waste removal conduit. The removing means also desirably includes a holding reservoir connected in communication with the waste removal conduit. As embodied herein, the removing means further includes a vacuum blower that is configured and disposed so that it can create a suction force in at least the catching means and the waste removal conduit and is connected in communication with the holding reservoir.

In further accordance with the present invention, the removing means can include a portable, manually directed suction device in the form of a vacuum wand that is connected in communication with the holding reservoir and the vacuum blower via a flow diverter valve so that the vacuum blower is disposed in a manner that can create a suction force at the free end of the vacuum wand. The suction line that connects the tip of the vacuum wand in communication with the vacuum blower can be prelubricated by a spray of liquid that is introduced when the suction operates through the vacuum wand.

In accordance with the present invention, means can be provided that prevent operation of the vacuum blower from drawing wastes out of the removing means and backing same into the vacuum blower conduits which enable the vaccum blower to communicate with the interior of the holding reservoir. As embodied herein, the waste backup prevention means can include a controller which receives a signal from a high liquid level sensor disposed at a high level in the holding reservoir and turns off the blower while signaling the operator that service is required.

In still further accordance with the present invention, means can be provided for controlling odor. As embodied herein, the odor control means can include a cannister containing an odor filter such as activated carbon and connected so that either the vacuum blower exhausts into and through the cannister or draws air into and through the cannister before the air enters the vacuum blower.

In yet further accordance with the present invention, the removing means can include means for cleansing. As embodied herein, the cleansing means can include a rinse solution container for holding rinse solutions. The cleansing means also can include a rinse solution conduit that carries the rinse solution from the rinse solution container to the vacuum wand. The cleansing means also can include a rinse pump that provides the rinse solution under pressure to the vacuum wand. The cleansing means also can include a rinse spray nozzle that is mounted on the vacuum wand and through which the rinse solution is pumped by the rinse pump upon activation of a rinse trigger. The spray nozzle is configured and disposed so that it does not come into contact with the tip of the vacuum wand and directs the spray at the base of the back side of the tip of the vacuum wand. The tip of the vacuum wand has safety louvers on the back side so that suction can be applied via this tip directly to a surface without the pooling of rinse liquid.

In accordance with the present invention, means can be provided for detecting a predetermined level of liquid in the rinse solution container and providing a signal upon detecting same. The rinse solution level detecting means can include a liquid sensor having a portion permanently mounted and disposed inside the rinse solution container and producing an electrical response and providing same to a detection circuit when the level of liquid within the rinse container uncovers the liquid sensor. The detection circuit can be electrically connected to a controller such as a microprocessor, which in turn can activate an alert signal on a control panel to advise the operator to refill the rinse solution container with liquid.

In accordance with the present invention, means can be provided so that the rinse pump automatically provides rinse solution to the vacuum wand whenever the vacuum wand is going to be used by the operator. As embodied herein, the automatic activation means for the rinse pump can include a microswitch which is activated to turn on the rinse pump whenever the operator tries to use the vacuum wand. Desirably, the controller should be preprogrammed to check the liquid level sensor in the rinse solution container so that the rinse pump does not operate if the level of rinse solution inside the rinse container is too low.

In accordance with the present invention, means can be provided for receiving the rinse solution container. As embodied herein, the rinse container receiving means desirably includes a first housing configured for receiving the rinse solution container. The first housing desirably includes a slide receptacle configured for slidably engaging a mutually configured portion of the rinse solution container.

In still further accordance with the present invention, means can be provided for detecting when the rinse solution container is securably received by the housing. As embodied herein, the securably received detecting means is connected to provide a signal to the controller, which the controller in turn can provide to a control panel. The securably received detecting means can include an electrical circuit which includes an electrically conducting plate permanently mounted and disposed in the exterior of the rinse container and electrically connected in communication with the controller, whereupon the circuit changes its electrical status when the rinse solution container is securably received by the housing.

In yet further accordance with the present invention, the first housing can include means for automatically connecting the rinse solution container in communication with the rinse spray nozzle of the vacuum wand when the housing receives the rinse solution container. As embodied herein, the rinse container connecting means can be configured to prevent any of the rinse solution from escaping the rinse solution container when the connecting means is disengaged from the housing. The connecting means desirably includes a dripless connector having a male member and a female member, each provided with spring-loaded poppet type closures that seal their openings unless mutually engaged to one another. One of the members is formed as part of an inlet/outlet valve formed in the exterior of the rinse solution container, and can be connected to a siphon member having its free end disposed just below the level of the level sensor. The other of the connector members can be attached to the exterior of the housing and disposed in communication with the rinse solution conduit that connects to the vacuum wand.

The first housing desirably also is provided with a means for automatically coupling the liquid level detecting means to the controller when the rinse solution container is received by the first housing. As embodied herein, the automatic coupling means desirably includes an electrically conducting contact plate disposed on the rinse solution container and a pair of electrically conducting spring-loaded probes mounted in the first housing to engage the contact plate when the rinse solution container is received by the first housing.

In still further accordance with the present invention, means can be provided for collecting the waste that is removed from the catching means by the removing means. The waste collecting means desirably is disposed to be in communication with the removing means and contains the waste in a manner that isolates the waste from the patient and facilitates the eventual disposal of the contained waste by persons attending the patient. As embodied herein, the collecting means desirably includes a waste collection container. The waste collection container is desirably provided with similar means to those that are provided for the rinse solution container, except that the level sensing means detects a full container rather than an almost empty container and accordingly is disposed near the top of the container.

As embodied herein, the collecting means can further include a waste transfer pump and waste transfer conduits. The waste transfer conduits connect an outlet opening defined in the bottom of the holding reservoir to the waste collection container via the waste transfer pump.

In still further accordance with the present invention, means can be provided for automatically controlling the operation of the waste transfer pump so as to transfer waste from the removing means to the waste collection container whenever a predetermined level of waste has accumulated within the holding reservoir. As embodied herein, the waste transfer pump control means desirably includes another liquid level sensor which can be disposed with respect to the holding reservoir so as to detect when the waste transfer pump should be activated for the purpose of pumping waste from the holding reservoir into the waste collection container. One embodiment of a suitable liquid level sensor can include an electrically conducting probe having a portion disposed inside the bottom of the holding reservoir. In addition, the means for automatically controlling operation of the waste transfer pump so as to transfer waste from the removing means to the collection means, can further include an electrical circuit which includes the probe. The electrical circuit powers a signal and provides this signal to the controller. Upon receipt of this signal from the electrical circuit, the controller can perform any of a number of preprogrammed functions or operations, one of which is activating the waste transfer pump. However, the controller additionally can be preprogrammed to check the liquid level sensor in the waste collection container so that operation of the waste transfer pump does not occur if the level sensor indicates that the level of waste inside the waste container is too high.

In yet further accordance with the present invention, means can be provided for automatically detecting a predetermined level of liquid within the holding reservoir and providing a signal upon detection of same. As embodied herein, this liquid level detecting and signalling means desirably includes an electrical probe configured and disposed for detecting and signaling when the holding reservoir becomes filled to a predetermined proportion of its capacity. The probe is part of an electrical liquid level detection circuit, which provides a signal to the controller depending upon the absence or presence of liquid at a predetermined level inside the holding reservoir. The controller activates an alerting signal appropriate to the signal sent by the detection circuit.

Each of the containers, the waste collection container and the rinse container, desirably is separately configured so that each provides means for preventing interchange of the waste collection container with the rinse solution container when being connected to the waste managing means of the present invention. Alternatively, either the connectors for each container would be differently configured or located in a relatively different position. In either case, it would be impossible to interchange the two containers. Each of the connectors desirably is formed as a quick-disconnect type connector which automatically remains open when the container is connected so as to receive waste and automatically remains sealed when the container is disconnected so that the container can be transported to a remote site for refilling or emptying, as appropriate.

In yet further accordance with the present invention, means can be provided for keeping track of the amount of fluids that is expelled by the patient through incontinence events. As embodied herein, the expelled fluid accounting means can include forming the waste collection containers of translucent material and providing volume graduations on the inside or outside surfaces of the container to provide a visually observable level indicator for the fluid inside the container.

In still further accordance with the present invention, means can be provided for detecting and signalling a waste-producing event. The detecting and signalling means desirably communicates with at least one of the catching means, the removing means, and the collecting means. As embodied herein, the detecting and signalling means can include a moisture sensor, which is disposed so that it can detect liquid in at least one of the catching means, the removing means, and the collecting means. The moisture sensor can be disposed in a drain fitting near the upper region of the waste removal conduit just below the catching means and can include a pair of electrically conducting rings secured to the inside wall of the fitting and spaced from one another by about one-quarter inch. Desirably, the rings are electrically connected in an electrical circuit that is complete when moisture flows between the two rings. A signalling mechanism can be provided on a control panel so that when moisture flows between the two rings, a signal is sent to a controller, which in turn activates the signalling mechanism on the control panel.

In further accordance with the present invention, means can be provided for controlling operation of the vacuum blower in response to moisture detection by the moisture detecting and signalling means. As embodied herein, the vacuum blower control means can include a controller that can be programmed to activate the vacuum blower to a higher speed upon receipt of a signal from the moisture detection circuit indicating that moisture has entered the upper region of the waste removal conduit. At the higher speed, the vacuum blower provides sufficient suction to pull the moisture out of the waste removal conduit and into the holding reservoir.

In accordance with the present invention, means can be provided for counting the number of waste producing events that occur during a given period of time. As embodied herein, the counting means can include a controller that is suitably programmed to keep track of the number of signals received from the moisture detecting and signalling means during a given interval of time.

In further accordance with the present invention, means can be provided for adapting the managing means apparatus of the present invention to be carried by the frame of a patient support apparatus. The carrying adapting means desirably is supported by the frame of the patient support apparatus. As embodied herein, the carrying adapting means can include an adaptor shell that defines a bottom surface configured for being carried by the frame of the patient support apparatus. The adaptor shell defines a receiving opening in a central location of the shell. The receiving opening is configured for securingly and supportingly receiving the support member of the managing means apparatus of the present invention in a manner that disposes the support surfaces of the support member substantially in the same plane with the support surfaces of the patient support apparatus. In a low air loss bed for example, this patient support surface is defined by the upper surfaces of the sacks of the low air loss bed. The adaptor shell desirably is formed by a plurality of individual inflatable cushions that have a generally U-shaped external configuration which defines the receiving opening. An elongated slot can be defined in the intermediate portion of an extra wide cushion located near the center of the adapter shell. This slot provides access for the waste removal conduit that connects the holding reservoir in communication with the drain opening of the basin member. Desirably, the cushions are formed as air-tight enclosures and are inflatable with pressurized air. Alternatively, the adaptor shell can be formed of urethane foam.

As embodied herein, the means for carrying the managing means can further include a tray which mounts to the frame of the patient support apparatus and can support the battery power supply. The carrying means also can include a foot-mounted container that includes an enclosure and a base plate which slides horizontally into and out of the enclosure. The holding reservoir, the waste transfer pump, and the vacuum blower can be mounted on the base plate. Alternatively, the carrying means can be formed as a mobile service cart, which is either upright or has an undercarriage with a low profile that can be slid beneath one end of the frame of the patient support apparatus.

In yet further accordance with the present invention, means can be provided for turning the patient to facilitate cleansing after a waste-producing event. Desirably, the turning means is carried by the frame of the patient support apparatus and can include a plurality of specially configured turning sacks which are provided with pressurized air in one or more configurations under the control of a controller. Desirably, a turning sack can be alternated with a conventional low air loss bed support sack. In addition, a pair of air flow diverter valves can be configured and disposed in series and actuatable by the controller to enable the controller to selectively inflate or deflate either the turning sacks or the conventional support sacks.

In yet further accordance with the present invention, means can be provided for alerting and/or informing the operator to various conditions of the apparatus of the present invention. The alerting and informing means can include a control panel that is electrically connected to the controller and provided with various indicators that the controller can operate as well as reset after the indicator has been operated.

The accompanying drawings, which are incorporated in and constitute a part of this specification, illustrate one embodiment of the invention and, together with the description, serve to explain the principles of the invention.

BRIEF DESCRIPTION OF THE DRAWINGS

FIG. 1A schematically illustrates components of a preferred embodiment of the present invention from an elevated perspective view;

FIG. 3 schematically illustrates a representative portion of a grid configuration structure provided on the surface of a portion of a component of the present invention;

FIG. 4 schematically illustrates a side plan view of components of a preferred embodiment of the present invention;

FIG. 4 schematically illustrates a cross-sectional view of components of a preferred embodiment of the present invention;

FIG. 14 schematically illustrates components of a preferred embodiment of the present invention from a side plan view with portions cut away;

FIG. 14A illustrates an expanded cross-sectional view of details of components of an embodiment of the present invention illustrated in FIG. 14;

FIG. 14B illustrates an expanded front plan view of components of the present invention illustrated in FIG. 14;

FIG. 5 schematically illustrates components of an alternative preferred embodiment of the present invention from a side plan view with portions indicated in phantom by the dashed lines;

FIG. 23 schematically illustrates components of a preferred embodiment of the present invention from a front plan view;

FIG. 29A illustrates a rear plan view of a preferred embodiment of waste collection container 192 of the present invention with portions cut away to illustrate features on the front of the container and portions shown in phantom by dashed lines; and FIG. 29B illustrates a rear plan view of a preferred embodiment of rinse solution container 142 of the present invention with portions cut away to illustrate features on the front of the container and portions shown in phantom by dashed lines.

DETAILED DESCRIPTION OF THE PREFERRED EMBODIMENTS

Reference now will be made in detail to the presently preferred embodiments of the invention, one or more examples of which are illustrated in the accompanying drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents.

Figure 1:
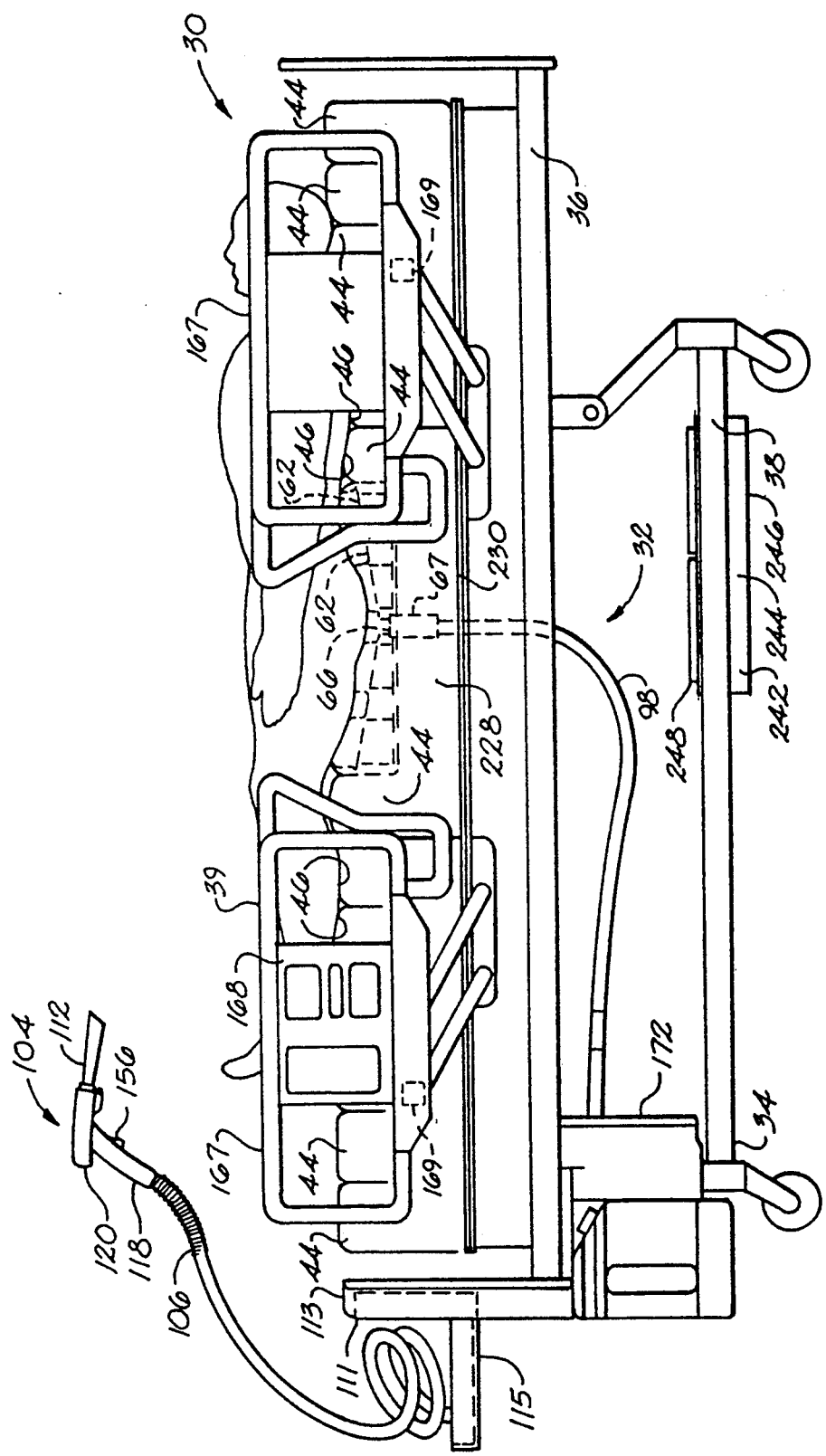
FIG. 1 schematically illustrates a preferred embodiment of the present invention viewed from an elevated side plan perspective in a low air loss patient support system.

In accordance with present invention, there is provided a low air loss patient support apparatus which incorporates means for managing waste from a patient who is supported at least in part on patient support surfaces of the low air loss patient support apparatus. The numeral 30 in FIG. 1 refers generally to a presently preferred embodiment of a low air loss patient support apparatus which incorporates means for managing waste from a patient who is supported at least in part by patient support surfaces of apparatus 30. As is conventional, bed 30 includes a frame having rigid members for carrying a plurality of sacks 44 which are configured to be inflatable with a pressurized gas. As embodied herein and shown in FIGS. 1 and 1A for example, the frame can include a lower frame 34 and an upper frame 36. Each of lower frame 34 and upper frame 36 can be formed of a pair of opposed, rigid tubular frame rails 38 for carrying various components of the present invention. As shown in FIG. 1A for example, each tubular frame rail 38 defines a rectangular configuration including an interior sidewall 40 defining the height of frame rail 38 and disposed at a right angle to a top wall 42 defining the width of frame rail 38. As embodied herein and shown in FIG. 1 for example, upper frame 36 provides a rigid support beneath a plurality of inflatable sacks 44 carried by the frame. In order to avoid unduly complicating FIG. 1, the articulating sections of upper frame 36 are not specifically illustrated. Similarly, the side panels normally attached to snaps mounted on the outside surfaces of the end walls of air sacks 44 are not illustrated in FIG. 1 in order to avoid unduly complicating the drawing. However, examples of such side panels are disclosed in each of U.S. Pat. Nos. 4,745,647 to Goodwin: 4,768,249 to Goodwin; 4,914,760 to Hargest et al: 4,942,635 to Hargest et al: 4,949,413 to Goodwin: 4,949,414 to Thomas et al; 5,035,014 to Blanchard: and 5,051,673 to Goodwin: the entire disclosures of each of the foregoing patents being hereby incorporated into this patent application by this reference.

Air sacks 44 are constructed and configured in a manner that permits them to define a support surface that conforms to at least a first portion of the body of the patient. The support surface supports the patient above the frame when the sacks are inflated with the pressurized gas. Examples of details concerning the frame, the sacks, and the manner of articulating the frame and supplying and controlling pressurized gas to the sacks are disclosed in one or more of the above-referenced U.S. Patents.

In accordance with the present invention, means are provided for managing waste associated with the care and/or treatment of a patient. The waste managing means of the present invention effectively manages different types of wastes, including, but not limited to, wastes from patient incontinence, patient bathing, patient wound irrigation, and emergency treatment of a patient. Moreover, different embodiments of the waste managing means of the present invention can be provided to suit different types of beds, different environments, and different users. For example, an embodiment of the waste managing means can be provided for managing incontinence from patients confined to wheelchairs. Another embodiment can serve as a bathing apparatus for patients who have very sensitive skin conditions. Yet another embodiment can serve as a working surface in a hospital emergency room setting in which trauma victims can be treated while controlling and containing blood, other bodily fluids, and treatment fluids that are present in such environments. For purposes of illustrating the waste managing means of the present invention, an embodiment of the waste managing means will be described for a patient whose body is supported at least in part on the support surface of a low air loss patient support apparatus. Accordingly, the numeral 32 in FIG. 1 refers generally to an embodiment of the waste managing means associated with the patient occupant of low air loss bed 30.

In accordance with the present invention, at least some portion of the patient's body is supported by the waste managing means, which provides means for receiving, removing, collecting and containing for disposal, waste from patient-related events, whether such events occur during routine patient care such as by patient incontinence or bathing, or during patient treatment procedures, wherein such waste managing means operate independent of active cooperation of the patient prior to the occurrence of the waste-producing event, independent of prepositioning the patient prior to the occurrence of the waste-producing event, independent of active cooperation of the hospital staff prior to the occurrence of the waste-producing event, and independent of movement of any section of the waste managing means prior to the occurrence of the waste-producing event.

While at least a first portion of the patient's body is supported in a patient support apparatus, such as a loss bed 30 for example, the waste managing means desirably includes means for supporting at least a second portion of the patient. The second portion of the patient desirably is supported at a level that enables the patient to be supported in the neutral plane. The body rests in its neutral plane when the body is supported so that its muscular/skeletal system is maintained at equilibrium, i.e., without muscular tension. Thus, the second portion of the patient desirably is supported at a level that is coextensive with the way that the rest of the patient's body is carried by the support surface of the patient support apparatus and thus is desirably at substantially the same height above the frame of the patient support apparatus. Accordingly, the second portion supporting means defines a first surface that is configured and disposed substantially coextensive with the support surface of the patient support apparatus. As illustrated in FIG. 1 in a low air loss patient support apparatus 30 for example, the patient support surface is defined by the plurality of upper surfaces 46 of the inflatable sacks 44. In embodiments of the waste managing means intended to address patient incontinence, the second portion of the patient's body desirably includes the portion of the patient's body that defines the excretory organs of the patient. Moreover, the second patient body portion supporting means desirably functions to support the second portion of the patient's body "coplanar" with the support surfaces 46 of the patient support apparatus 30. In this sense, the word "coplanar" defines a plane that follows along the contour of the outline of the body of the patient being supported, rather than a strictly flat plane.

The second patient body portion supporting means includes a support member. The support member carries the weight of the second portion of the patient's body. The support member carries this weight in a manner that provides pressure relieving support to the second portion of the patient's body. In this way, the support member of the waste managing means can cooperate with a low air loss bed to provide overall pressure relieving support to the patient's entire body.

In one embodiment, as shown in FIGS. 2, 2A, 5 and 19 for example, the support member of the waste managing means can be provided in the form of a support bladder 48 which defines an envelope formed of flexible, elastic material that defines a gas tight enclosure configured to contain pressurized air. Configured as such, the rigidity of support bladder 48 can be varied by varying the pressure of the gas, typically air, contained within same. Antimicrobial material could be impregnated directly into the flexible material forming support bladder 48 and/or permanently bonded onto the surface of the flexible material forming support bladder 48.

Figure 2:
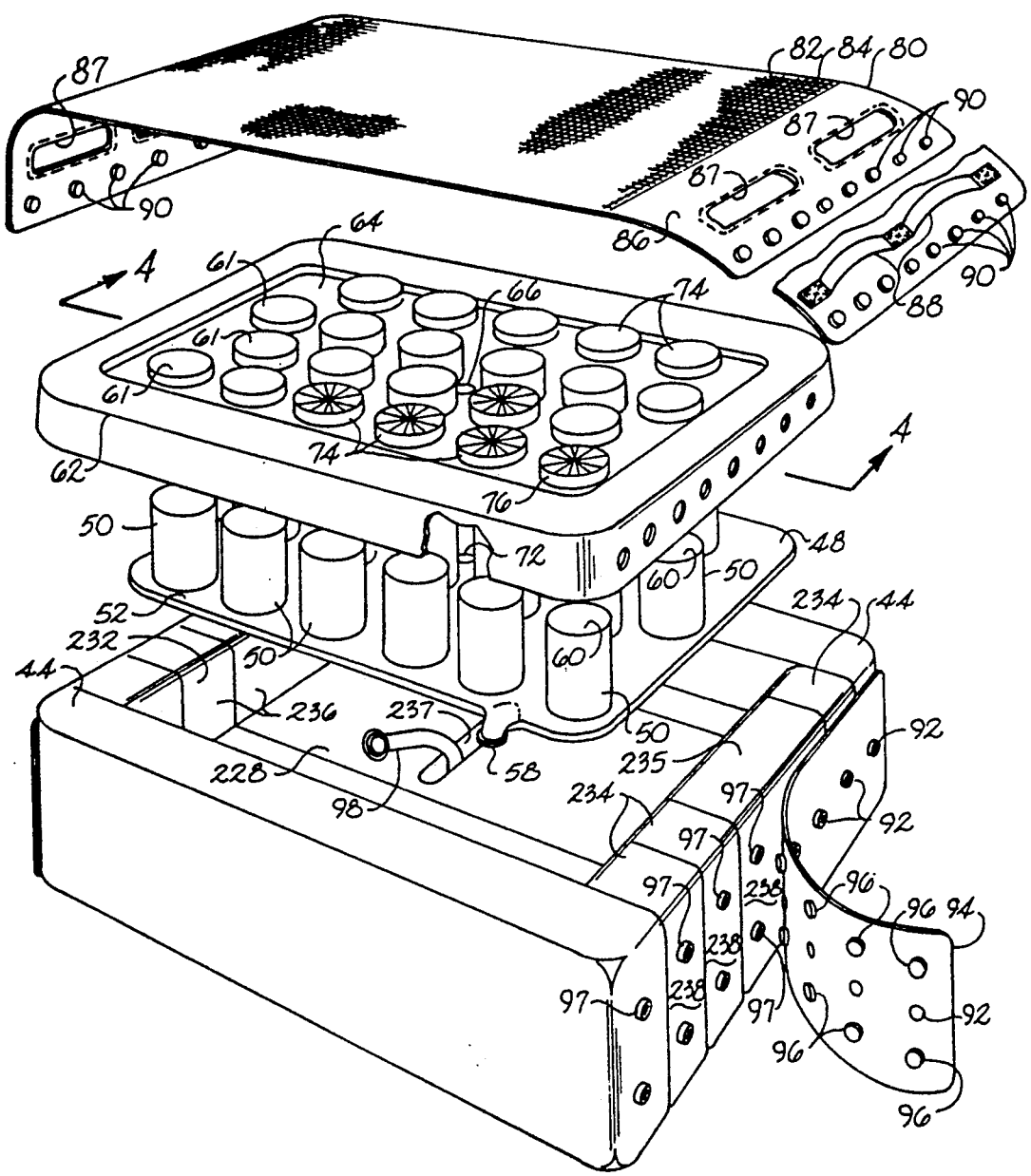
FIG. 2 schematically illustrates components of a preferred embodiment of the present invention from an elevated perspective view.
Figure 2A:
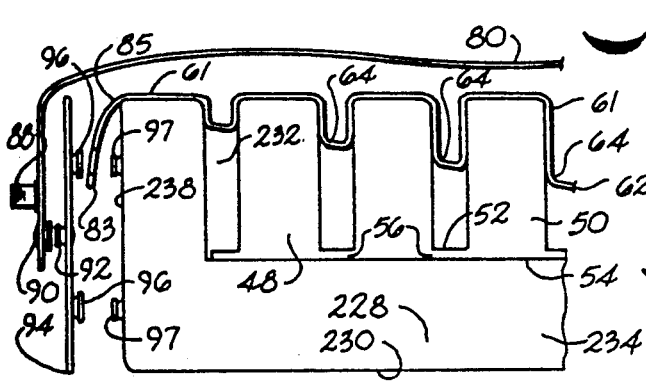
FIG. 2A schematically illustrates portions of components of a preferred embodiment of the present invention from a partially cut away side plan view.
Figure 5:
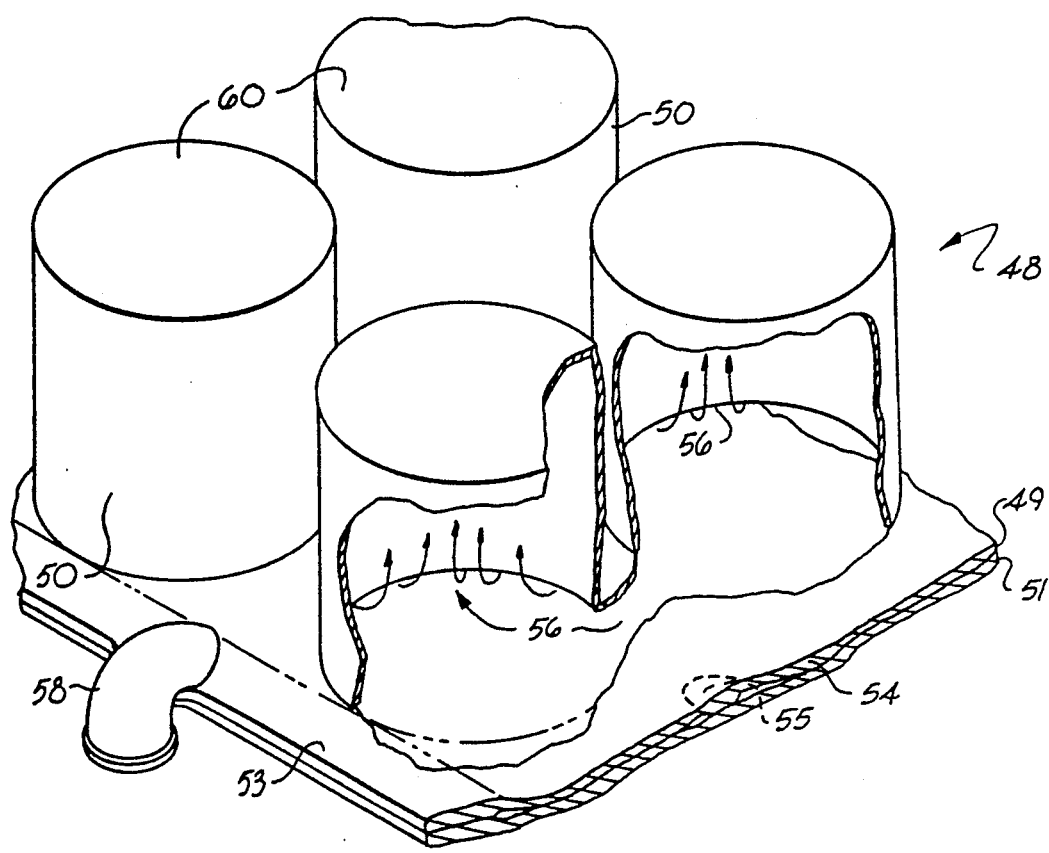
FIG. 5 schematically illustrates a portion of a component of a preferred embodiment of the present invention with portions of the component cut away for illustrating aspects normally hidden from view.
Figure 6:
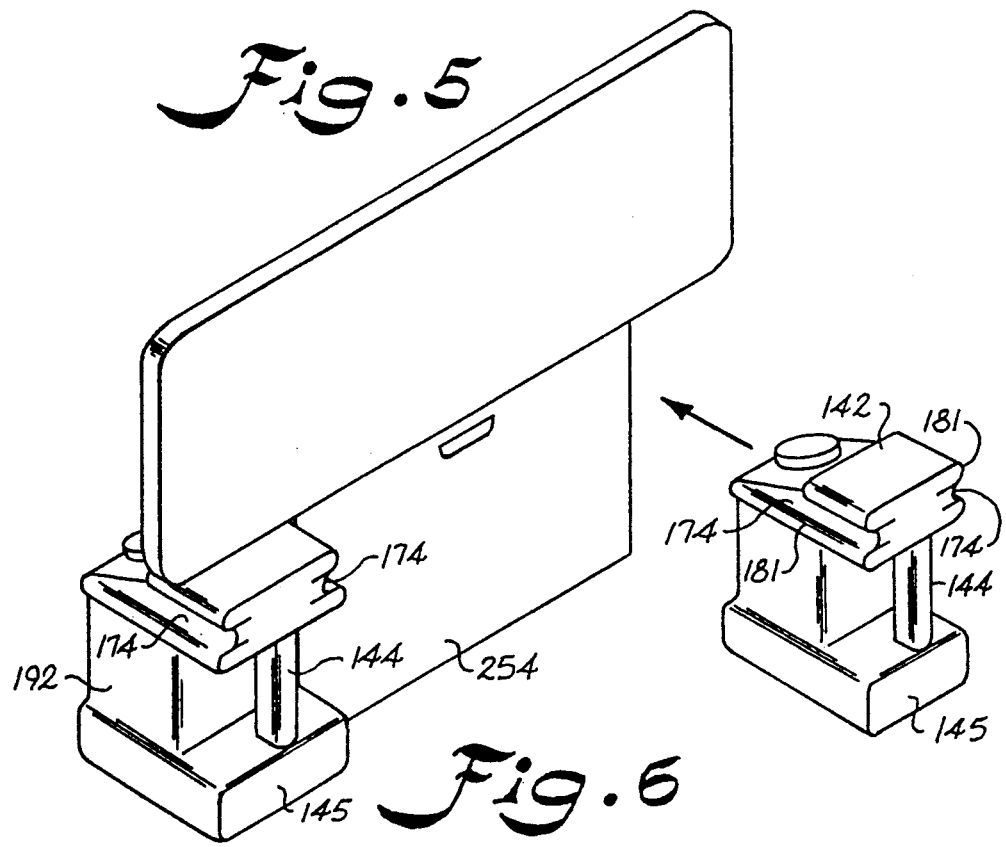
FIG. 6 schematically illustrates components of the present invention from an elevated perspective view.

As illustrated in FIG. 5 for example, support bladder 48 desirably is formed of two pieces, a top piece 49 and a bottom piece 51. As illustrated in FIGS. 2A and 5 for example, top piece 49 of support bladder 48 desirably is a unitary structure defining a plurality of cylindrical fingers 50 as well as the adjoining floor portions 52 which define the separation between fingers 50 and form the upper floor of the support bladder. Bottom piece 51 forms the continuous flat underside of the base portion 54 of the support bladder and is sealed to top piece 49 continuously around the peripheral border portions 53 and at selected points 55 in the interior portions away from the periphery. As shown schematically in FIG. 5 for example, each of top and bottom pieces 49, 51 of support bladder 48 can be formed by a dip molding process which uses a molding tool that defines stand-off adhesive points 55 of bladder 48. Top piece 49 can be attached in air tight fashion to bottom piece 51 by radio frequency (RF) sealing or adhesive bonding the periphery 53 and stand off adhesive points 55. This type of construction leaves channels 56 defining large open areas for air to travel between cylinders 50. These large internal channels 56 permit air to be distributed quickly and enter each of the cylinders 50 from one or more common fittings 58. Thus, support bladder 48 responds quickly to equalize pressures between cylinders 50. Moreover, the size of channels 56 poses no impediment to rapid deflation of support bladder 48 for purposes of implementing a CPR procedure.

Figure 19:
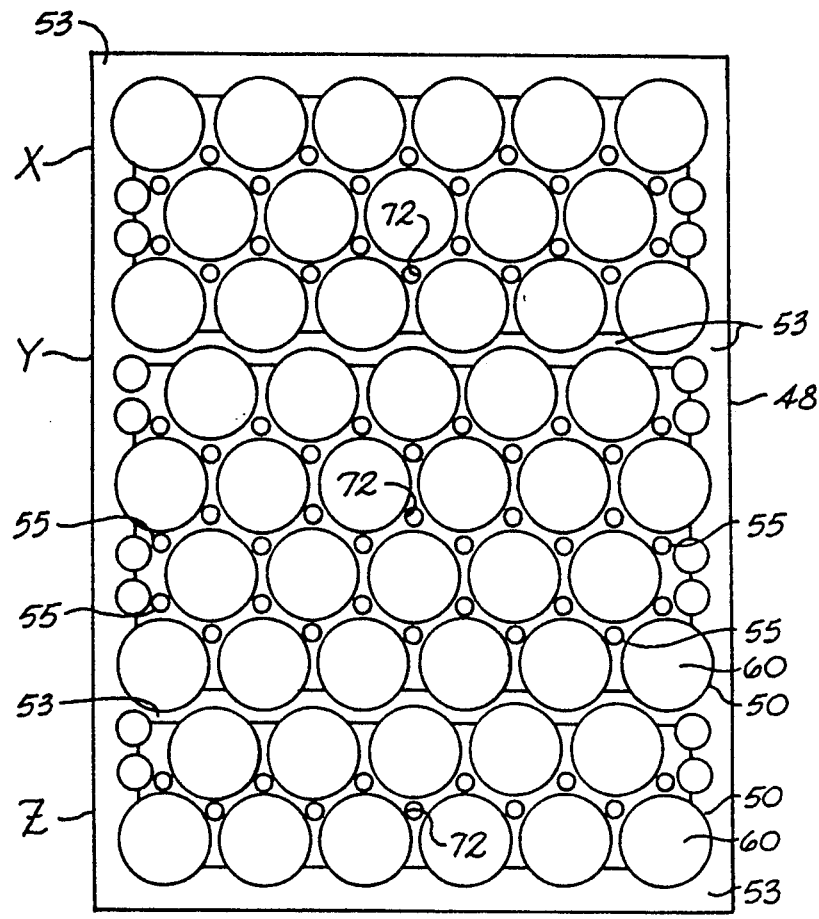
FIG. 19 schematically illustrates components of a preferred embodiment of the present invention from a top plan view.

An alternative embodiment of support bladder 48 is schematically illustrated in FIG. 19 for example. In this embodiment, three separately inflatable sections X, Y, and Z are defined by continuous peripheral sealed borders 53. Though not shown in the top plan view of FIG. 19, each section X, Y, Z is provided with an air inlet fitting through which pressurized air can be supplied. Depending on the length of each section, each section X, Y, Z can be provided with its own opening 72 to accommodate a drain opening 66 (described below). The FIG. 19 embodiment of support bladder 48 is desirable when the waste managing means of the present invention is to be carried on an articulating surface. Then each section X, Y, Z of bladder 48 can be carried on a separate articulating portion of the articulating surface. If the FIG. 19 embodiment of support bladder 48 were to be provided for a low air loss bed 30 such as shown in FIG. 1 for example, then section X would correspond to the calf zone of bed 30, section Y would correspond to the buttocks zone of bed 30, and section Z would correspond to the lower torso zone of bed 30. The FIG. 19 embodiment of support bladder 48 also is desirably provided for a low air loss surface for sponge bathing a patient or for treating trauma patients in a hospital emergency room setting.

An alternative dip molding manufacturing technique for producing a support bladder 48 for the present invention is described in part in one or more of U.S. Pat. Nos. 4,698,864; 4,541,136; 3,605,145; 3,870,450 and 4,005,236 to Graebe, the disclosures of which patents are all hereby incorporated into this patent application by this reference. However, the technique described in these patents is desirably modified to provide more open channels 56 between cylinders 50.

As described above and illustrated schematically in FIG. 5 for example, support bladder 48 defines a plurality of cylindrical pockets 50 which are inflatable with air to form air-filled cylindrical columns 50, also referred to as cylinders 50 or fingers 50. Air-filled cylindrical columns 50 are pressure-relieving cylinders. As shown in FIGS. 2, 4, 5 and 19 for example, each cylindrical column 50 has a circular transverse cross-section. However, other shapes, such as a triangular shape, a square shape, a rectangular shape, a pentagonal shape, a hexagonal shape, or another polygonal shape or closed curvilinear shape, can be used.

Each cylindrical column of the support member defines a discrete support finger 50 that is disposed adjacent to, but separated from, other support fingers 50 in a predetermined pattern of arrangement. As shown in FIGS. 2, 4, 5 and 19 for example, each support finger 50 has a free end which defines a patient support surface 60. Each patient support surface 60 of each finger 50 is disposed to support the weight of a second portion of the body of the occupant of the waste managing means of the present invention. When the invention is provided in an embodiment for incontinence management, desirably the portion of the patient's body defining the excretory organs is disposed to be supported by the patient support surfaces 60 of the support member. The pressure of the air in each cylindrical column 50 desirably is the same for each column located within a particular patient support zone (see FIG. 19 for example) of the bed or other structure in which the apparatus of the present invention is being used.

In an alternative embodiment of the support member, the support member can be defined as a support cushion formed of a resilient foam member. However, such an embodiment would not be recommended for an application that required a rigid surface for performing CPR. The rigidity of the support cushion embodiment of the support member can be varied only by varying the density and composition of the resilient foam used to form the cushion when the cushion is originally manufactured. The configuration of the support cushion embodiment of the support member is the same as described above with regard to support bladder 48 and thus includes a plurality of spaced apart cylindrical fingers 50.

Assuming that the individual cylinders 50 of the support member are arrayed according to a uniform pattern and assuming further that each of cylinders 50 is identically configured, the size and configuration of the support member is defined by one or more of a number of parameters. These parameters include: the rigidity/flexibility of the material forming the cylinders 50 (in an inflatable embodiment of the support member, the operating pressures of the support member also must be taken into account); the cylinder height measured from adjoining floor portions 52 to support surfaces 60; the area of the support surface 60 of the free end of each cylinder 50; the number of cylinders 50 per unit of area of the support member; and/or the relative percentage of area occupied by support surfaces 60 of cylinders 50 versus the area occupied by the gaps between cylinders 50 at the same height of the support surfaces 60. The design of the configuration, i.e., size and shape, of the support member and its fingers 50 proceeds according to certain requirements.

A basic design requirement pertains to the interface pressure, which is the pressure exerted on the body of the patient by the supporting surface area defined by the support surface 60 of each finger 50 of the support member. The interface pressure must be kept below the capillary closure threshold pressure, which most authorities would agree is 32 millimeters of mercury for most patients. Moreover, this threshold pressure must not be exceeded even when the head section of the bed is articulated so as to apply maximum pressure in the area supporting the buttocks of the patient. Thus, the supporting surface area defined by the support surface 60 of each cylinder 50 must be large enough to keep the pressure inside each cylinder, and thus the interface pressure between the surface of the cylinder and the patient supported thereon, less than 32 millimeters of mercury. The larger the area defined by support surface 60 of the cylinder in contact with the second portion of the patient's body, the lower is the interface pressure against the patient's body. The cumulative surface area of the support surfaces 60 of the cylinders 50 in contact with the patient's body, depends on the number of cylinders per unit of area of the support member and also on the area of each support surface 60 of the free end of each cylinder 50. The calculation also depends on the anticipated weight (primarily) and height (secondarily) of the patient to be supported.

There is a trade-off between the area occupied by the gaps between cylinders 50 in the plane containing support surfaces 60 on the one hand, and the area occupied by support surfaces 60 of the free ends of cylinders 50 on the other hand. As will become more apparent from the description of the invention provided hereafter, large area gaps are desirable to allow for maximum drainage capability and ease of drainage. However, as noted above, the larger the areas of support surfaces 60 of cylinders 50, the lower the interface pressure between the body of the patient and the support surface 60 of the cylinder 50.

Figure 7:
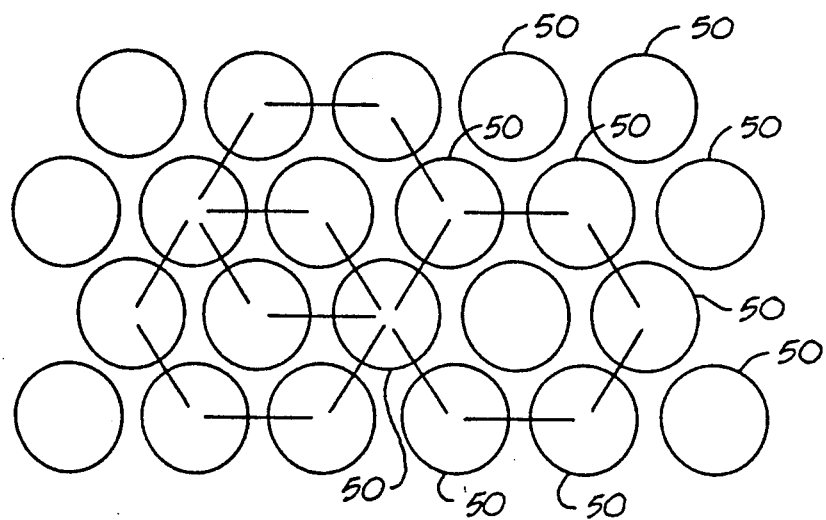
FIG. 7 schematically illustrates a pattern for portions of components of a preferred embodiment of the present invention from a top plan view.

In the present invention, fingers 50 are arrayed in a pattern that can be chosen depending upon manufacturing criteria, patient support criteria, and the environment in which the apparatus is going to be used. As to the patient support criteria, it is desirable that the supporting area of the cylinders versus the space between the cylinders have a so-called "support ratio" higher than 1. Thus, a support ratio of 2.33 (70% supporting area versus 30% area of gaps between the cylinders) is desirable. This permits lower internal pressures inside the cylinders to support a patient of a given weight and body surface area. As shown in FIG. 7 for example, one suitable pattern of arraying cylinders 50 is a hexagonal pattern in which each cylinder 50 is surrounded by six adjacent cylinders 50. However, as partially shown in FIG. 5 for example, another suitable pattern includes a square pattern, in which each cylinder 50 is surrounded by four adjacent cylinders 50. The square pattern results in a lower support ratio, something on the order of 50% of supporting surface and 50% of space between the cylinders. In the square pattern, the cylinders 50 are arrayed in straight rows and columns.

Another factor in these design requirements for the cylinders, takes account of the degree to which the cylinder buckles under a load, i.e., the ability of each individual cylinder to be compressed. This design requirement involves providing each cylinder 50 with sufficient height so that it can support a very heavy patient without bottoming the patient against a surface that is not pressure-relieving, i.e., a noninflated surface. As noted above, the support surfaces 60 of the cylinders 50 of the support member are configured to be disposed in a common plane which is intended to be a horizontal level plane co-terminus with the rest of the patient supporting surfaces 46 of the bed 30 or other patient supporting structure.

As noted above, when the body rests in its neutral plane, the body's muscular/skeletal system is maintained at equilibrium, i.e., without muscular tension. When the patient's body is being maintained in the neutral plane, it is desirable that the air pressurized cylinders 50 be configured so as to be capable of supporting even a heavy patient without bottoming any portion of the patient. Thus, the height of the cylinders must be tall enough to accommodate deformation that would still keep the patient's buttocks (the heaviest part of the body) supported by cylinders 50. Desirably, cylinders 50 are configured so that the largest possible deformation of each cylinder is about 4 inches. Accordingly, cylinders 50 of the support member of the present invention desirably are at least five inches tall. This allows the cylinders to maintain body alignment and accomodates compressive deformation of the cylinders without bottoming of the patient against any noninflated surface which might underlie the cylinders.

Yet another concern dictating the configuration of the cylinders 50 is a tendency for a tall, narrow cross-section cylinder to buckle and therefore become unstable. Thus, the height of the cylinder should not be so tall relative to its transverse cross-sectional area, that the cylinder becomes unstable. The ratio of the height of the cylinder to the diameter of the cross section of the cylinder, defines a useful parameter known as the "aspect ratio". In the present invention, the aspect ratio is desirably kept very close to one. In an effort to keep the aspect ratio at about 1 with the height of the cylinder at least five inches tall, the diameter of each circular transverse cross-section cylinder desirably should be on the order of four inches and preferably is in a range of from about 4 inches to about 4.5 inches.

Desirably, for patients weighing up to three hundred pounds, the height of the cylinders 50 of the support member is about five inches, the diameter of the circular transverse cross-sectional area of cylinders 50 is somewhere in the range of four inches to four and one-half inches, and the ratio of the area of supporting surfaces 60 of the cylinders 50 to the area of the gaps between cylinders is about 70% area of support surfaces 60 of cylinders 50 versus 30% area of gaps between cylinders 50.

In further accordance with the present invention, means can be provided for catching the waste from an incontinence event, bathing, wound irrigation, or emergency treatment, of the patient whose body is supported, at least as to a second portion of the patient's body, in the second portion supporting means. The catching means desirably is supported by the second portion supporting means and desirably is supported between the second portion of the patient's body and the second portion supporting means.

As embodied herein and shown schematically in FIGS. 1 (phantomed in dashed line), 2, 2A, 3, 4, 9, 17, 18 and 24 for example, the catching means desirably includes a basin member 62. As shown in FIGS. 2A, 3 and 4 for example, basin member 62 desirably is configured to conform snugly to the configuration of at least the free ends of support cylinders 50 of the support member. As shown in FIGS. 2 and 2A for example, basin member 62 thus defines a plurality of angularly truncated cylindrical portions 61, which snugly receive at least a plurality of at least the free ends and upper portions of support fingers 50 of support bladder 48. The height of the basin member should be designed to accomodate a wide range of vertical body displacement without bottoming, while maintaining proper body alignment.

Basin member 62 should be formed of material flexible enough so that basin member 62 offers no substantial impediment to collapsing into a flat surface when it is desired to deflate support bladder 48 in order to perform a CPR treatment on a rigid support surface. Basin member 62 desirably is formed of liquid impermeable material such as very flexible elastomer which is about 20 mils thickness. Moreover, antimicrobial properties can be built into the basin member 62 by impregnating antimicrobial material into the material forming basin member 62. Desirably, the basin member's upper surface (facing away from the lower surface, which receives the cylinders 50 of the support member) is formed of or coated with one or more layers of material that is hydrophobic and friction-reducing and thus assists in assuring gravity drainage of liquid waste toward one or more drain openings (described below). A suitable coating material contains a blend of polyurethane and silicone in the following proportions: 94 grams of CHEMGLAZE V-300 TM moisture cured urethane available from Lord Corp. of Erie, Pa.; 6 grams of CHEMGLAZE 9995 TM catalyst available from Lord Corp.; and 6 grams of DC-200 TM silicone fluid available from Dow Corning Corp. of Midland, Mich.

Figure 9:
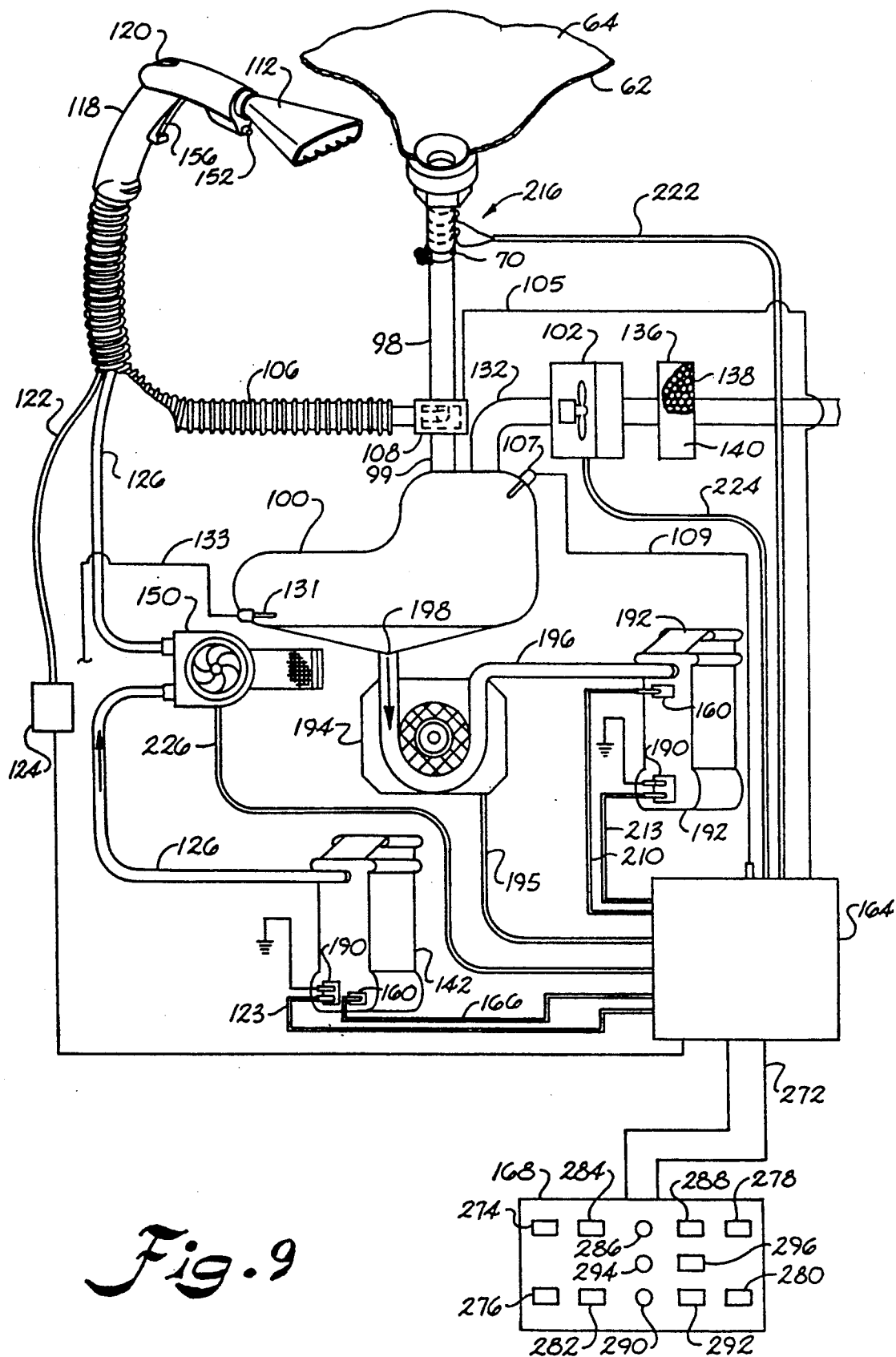
FIG. 9 presents a schematic representation of the interaction and cooperation of various components of a preferred embodiment of the present invention.

As shown in FIG. 4 in a cross-sectional view taken at an intermediate center line location shown in FIG. 2 by the arrows numbered 4—4 and as shown in FIGS. 2, 2A and 9 for example, basin member 62 is desirably further configured with a floor 64. Floor 64 is disposed beneath the level of support surfaces 60 of support fingers 50 when basin member 62 is fitted over support bladder 48 such that support fingers 50 are received in the conforming truncated cylindrical portions 61 (FIG. 2) of basin member 62.

As shown schematically in FIGS. 1, 2, 4, 9 and 24 for example, basin member 62 further is desirably configured with at least one drain opening 66 defined through the floor 64. The slope or height gradient of floor 64 is the rate of change of the height of floor 64 as one proceeds toward or away from drain opening 66. The angle at which truncated cylindrical portions 61 are joined to floor 64, is determined by the slope or height gradient of floor 64. As shown in solid line in FIG. 4 and in dashed line in FIG. 1 for example, basin floor 64 is desirably configured with a declining height gradient as one proceeds from the peripheral portion of basin member 62 toward drain opening 66. Drain opening 66 is disposed as the lowest height of this declining height gradient. Thus, in the embodiment shown in FIG. 4 and schematically in FIG. 24 for example, basin member 62 desirably is configured so that it has a single drain opening 66 at the center and has a floor 64 which slopes from the peripheral edges toward the center where drain opening 66 is located.

Figure 24:
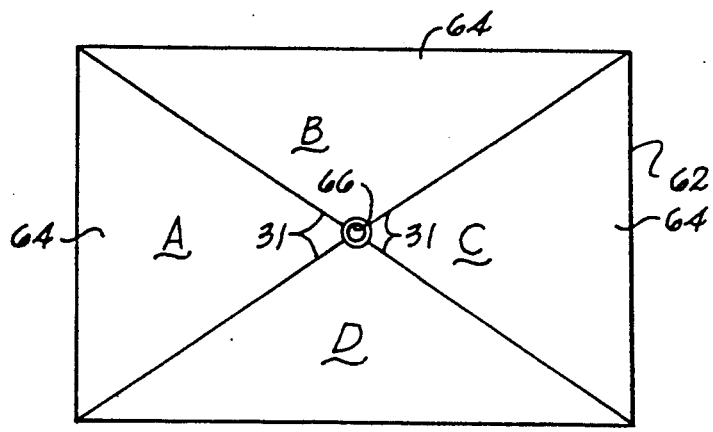
FIG. 24 schematically represents a top plan view of a preferred embodiment of a floor of a basin member component of the present invention for the purpose of illustrating one desirable configuration of the slope of the floor.

FIG. 24 schematically represents a top plan view of a rectangularly shaped basin member 62 for the purpose of illustrating one desirable configuration of the slope of floor 64. Four solid straight lines 31 emanate from drain opening 66 to divide floor 64 of basin 62 into triangular-shaped quadrants A, B, C, and D. If basin 62 were disposed in a low air loss bed 30 for example, then floor quadrant A would be situated toward the foot end of bed 30, quadrant C would be disposed toward the head end of bed 30, and quadrants B and D would be disposed toward either elongated side of bed 30. Desirably, each floor quadrant slopes downwardly from a horizontal plane toward drain opening 66 at a substantially constant slope. In one embodiment, the floor 64 in quadrant A has about an 8 degree slope, each of quadrants B and D has about a 13 degree slope, and quadrant C has about a 15 degree slope.

Figure 17:
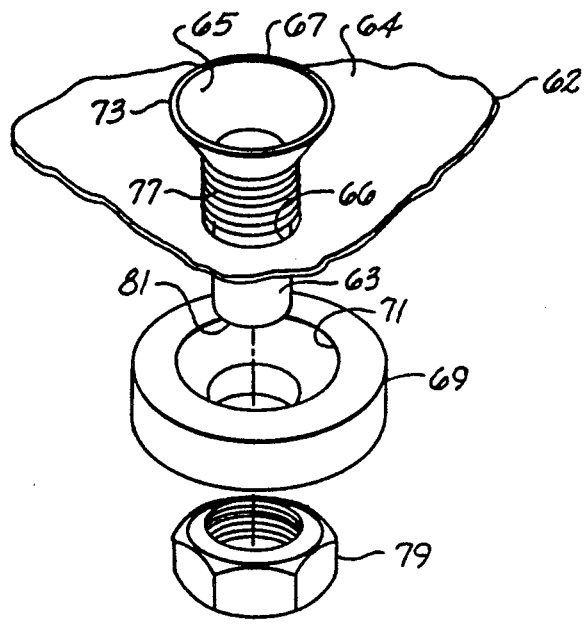
FIG. 17 schematically illustrates components of a preferred embodiment of the present invention from an elevated perspective view with portions cut away and separated from one another.
Figure 18:
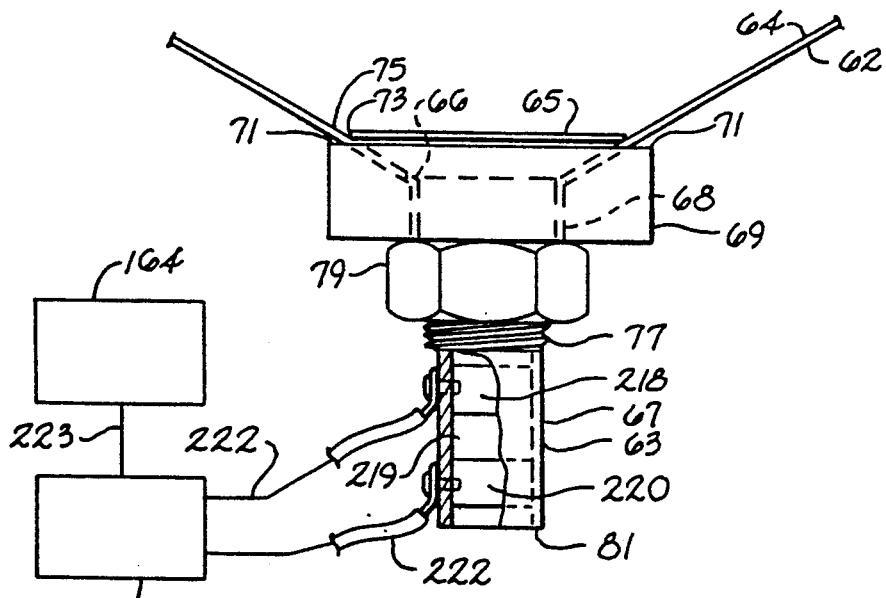
FIG. 18 schematically illustrates the components of FIG. 17 from a side plan view with portions cut away.

As shown in FIGS. 17 and 18 for example, a drain fitting 67 is disposed through drain opening 66 and defines a cylindrical portion 63 which extends from a truncated conical portion 65. Desirably, truncated conical portion 65 is configured with the same angular slope as the slope of floor 64 in the vicinity of drain opening 66. As schematically shown in FIG. 18 for example, a drain flange 68 defines a cylindrical extension of floor 64 of basin member 62 and extends beyond drain opening 66. Desirably, drain flange 68 forms a unitary structure with basin member 62. Drain fitting 67 extends into drain opening 66 with the cylindrical portion 63 extending down the inside of drain flange 68. A capture fitting 69 slides over the outside surface of drain flange 68 and captures drain flange 68 between capture fitting 69 and the exterior of truncated conical portion 65 of drain fitting 67. Capture fitting 69 is provided with a land configuration 71, which ensures that the interface 75 between the free edge 73 of drain fitting 67 and the lower portion 75 of basin floor 64 adjacent drain opening 66 is a smooth interface that disallows the pooling of any waste liquids in the vicinity of this interface 75. A threaded portion 77 is provided on the exterior surface of the cylindrical portion 63 of drain fitting 67 to receive a threaded nut 79, which secures capture fitting 69 to the truncated conical portion 65 of drain fitting 67. The free end 81 of the cylindrical portion 63 of drain fitting 67 is configured to be inserted through a centrally located opening 72 defined through the base 54 of support bladder 48.

In embodiments in which the support member extends the full length of an articulating supporting structure such as bed 30, one or more additional drain openings 66 might need to be provided in the basin member 62 because of the bending of the apparatus in accordance with the articulation of the underlying bed 30. A basin member that were to be configured to cover the embodiment of multi-zone bladder member 48 illustrated in FIG. 19 for example, likely would need to be provided with more than one drain opening 66. Each opening 72 in the FIG. 19 embodiment of support bladder 48 would accommodate a separate drain opening 66. Thus, each articulating section desirably would be provided with its own drain opening 66. In embodiments of the present invention having more than one drain opening 66, each particular drain opening 66 will define the localized lowest height of the floor's height gradient, which is constructed to allow gravity to assist movement of waste materials toward that local drain opening 66.

As embodied herein and shown in FIGS. 2 and 3 for example, basin member 62 defines a plurality of grid configurations 74. Each grid configuration 74 is desirably disposed in one of the portions of the basin member to be located above one of support surfaces 60 of one of support fingers 50 of the support member. Moreover, as shown schematically in FIG. 3 for example, each grid configuration defines a local exterior topography formed of a plurality of slightly raised portions 76 separated from one another by recessed channel portions 78. One example of the pattern of each grid configuration 74 includes rectilinear channels 78 and square raised portions 76 as shown for example in FIG. 3 (where only a sampling of the raised portions and channels are illustrated to avoid unduly complicating the drawing). As shown for example in FIG. 2, another grid configuration 74 includes channels 78 emanating radially from the center point and pie-shaped raised portions 76. Grid configurations 74 are only illustrated on a sampling of the upper surfaces of basin member 62 in FIG. 2 in order to avoid unduly complicating this drawing.

The channels 78 of the grid configurations 74 enable a filter sheet (described below) lying atop the basin member to readily transfer the waste fluids through the filter sheet to the basin member. To accomplish this purpose most effectively, the transverse width of the channel openings 78 are sized much larger than the pore size in the filter sheet. Thus, any particulate that was able to pass through the pore size of the filter sheet, could not block up the grid configuration channels 78 formed in the basin member surface which contacts the filter sheet.

Figure 25:
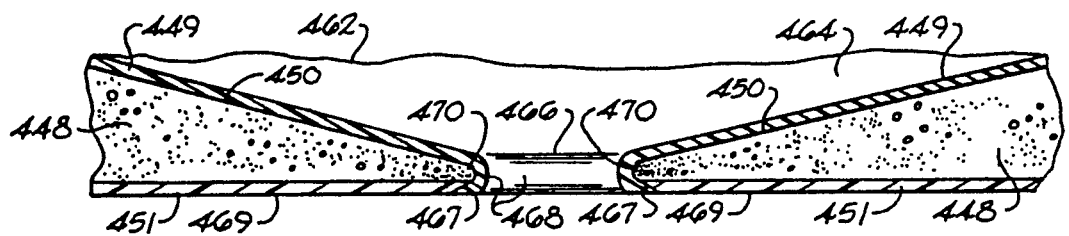
FIG. 25 schematically illustrates a partial cross-sectional view of a portion of a component of a preferred embodiment of the present invention shown in FIG. 4A.

In an alternative embodiment of the support member and the basin member illustrated in FIG. 4A and partially in FIG. 25 for example, the support member can include a resilient foam member 448 that is completely surrounded by a basin member 462 which is defined by a flexible envelope formed of resilient elastomeric material. The elastomeric basin member 462 is formed of two mating pieces, a top piece 449 and a bottom piece 451. Each of the mating pieces 449, 451 desirably is formed by dip molding. Top piece 449 of elastomeric basin member 462 is desirably eat sealed or sealed with adhesive coating to bottom piece 451 at an airtight seam 463. As shown in FIG. 25 for example, top piece 449 defines a drain opening 466 from which extends a cylindrical flange 468. Bottom piece 451 defines an opening 467 which is configured and disposed to be in registry with drain opening 466 and the free end of flange 468, which passes through opening 467 and is sealed in airtight fashion along opening 467 to bottom 469 of bottom piece 451. Thus, top piece 449 and bottom piece 451 are joined to surround and provide an air-tight enclosure for foam member 448. As shown in FIG. 4A for example, air can be supplied via a fill tube 458 which desirably is provided in bottom piece 451 of elastomeric basin member 462 and can be fitted with a valve 459 at the end thereof.

Top piece 449 is formed with a configuration similar to basin member 62 described above, and accordingly defines a plurality of angularly truncated cylindrical members 461 which are configured similarly to angularly truncated cylindrical members 61. Each angularly truncated cylindrical member 461 terminates in a substantially flat support surface 460 and is connected to an adjacent member 461 by a portion of a floor 464 which slopes toward a local drain opening 466. Desirably, all of the plurality of flat support surfaces 460 are disposed in a common plane. Each of the support surfaces 460 defines a grid configuration 474 which is configured similarly to grid configurations 74 described above and coated with a polymer that is both hydrophobic and has a very low coefficient of friction.

As embodied herein and shown in FIGS. 4A and 25 for example, foam member 448 is configured so that it provides support directly beneath the floor 464 of formed in top piece 449 of basin member 462. Foam member 448 has a top surface 450 that is configured to conform to floor 464 of top piece 449 of basin member 462. Opposite the top surface 450 of foam member 448 is a substantially flat bottom surface 452, which is received in bottom piece 451 of basin member 462.

Figure 20:
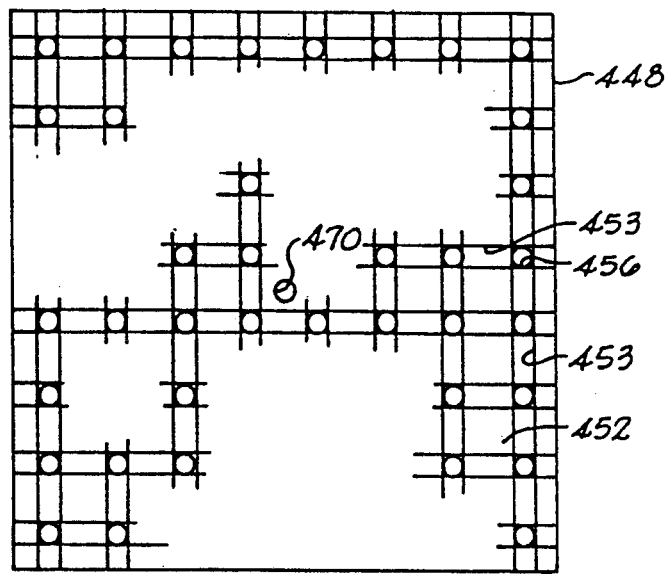
FIG. 20 schematically illustrates the foam member component of FIG. 4A, but from a bottom plan view.

Foam member 448 desirably is formed of material that is sufficiently permeable to the flow of air so that air can travel through the foam member itself. However, as shown in FIG. 4A for example, foam member 448 also desirably is provided with a plurality of vertically extending air passages 456. Each passage 456 extends completely through foam member 448 from top surface 450 to bottom surface 452. Foam member 448 desirably is configured and disposed within elastomeric basin member 462 so that each passage 456 is elastomeric basin member 462 so that each passage 456 is located beneath one of the angularly truncated cylinders 461 defined in top piece 449 of basin member 462. Moreover, as schematically shown in FIGS. 4A and 20 for example, the bottom surface 452 of the foam member desirably further defines a gridwork of horizontally extending grooves 453, which criss-cross through the bottom surface 452 and intersect at each opening of each passage 456 in bottom surface 452 of foam member 448.

When pressurized air is provided through fill tube 458 in bottom piece 451 of the basin member 462, the air flows through the grooves 453 in bottom surface 452 of foam member 448 and rises through each of the vertically extending air passages 456 defined in the foam member. The pressurized air fills the angularly truncated cylinders 461 defined in the top piece 449 of the elastomeric member 462. Moreover, the foam member 448 is sufficiently compressible so that the support member can be compressed by the weight of the patient when the pressurized air is released from the elastomeric basin member 462. Furthermore, as shown schematically in FIGS. 20 and 25 for example, foam member 448 further defines a drain opening 470. Cylindrical drain opening flange 468 extends through drain opening 470 of foam member 448 before passing through opening 467 in bottom piece 451 of basin member 462 and being sealed to bottom surface 469 of bottom piece 451. Thereafter, drain fitting 67 can be passed through drain openings 466 and 470 and opening 467 and then secured therein when capture fitting 69 and nut 79 are respectively slipped over and screwed onto cylindrical portion 63 and pinch top piece 449, foam member 448 and bottom piece 451 between conical portion 65 and capture fitting 69.

In yet further accordance with the present invention, the catching means desirably includes a liquid permeable filter sheet that is disposed to be carried above the basin member and closer to the second portion of the patient's body than the basin member. As embodied herein and shown in FIGS. 2 and 2A for example, a liquid permeable filter sheet 80 is disposed to be carried atop basin member 62 by those grid configuration 74 sections of basin member 62 which conform to support surfaces 60 of support fingers 50 of the support member. Thus, filter sheet 80 rests atop the flexible basin member that is supported by the inflated cylinders 50 of support bladder 48 for example. Filter sheet 80 constitutes a section of the catching means that is permeable to liquids.

The filter sheet is configured to trap larger solid waste material such as formed fecal matter and thus acts as a filter to prevent clogging of basin member 62 and drain fitting 67 (and other conduits described hereafter for transferring waste material). As embodied herein and shown in FIG. 2 for example, filter sheet 80 defines fabric having a plurality of small individual pores 82 between the threads 84 forming the filter sheet 80. The sizes of pores 82 are desirably very small so that there is a large number of them per unit of area of filter sheet 80, but not so small as to prevent rapid draining of liquids through the pores. Pores 82 render filter sheet 80 liquid permeable by allowing fluids to pass readily through filter sheet 80 to floor 64 of basin member 62. However, pores 82 are small enough to prevent passage of larger solid waste that otherwise might become lodged in the flexible basin member 62 or drain fitting 67 or waste removal conduit 98. The liquid permeable portion of filter sheet 80 containing pores 82 can be formed of woven material or spun bond continuous fibers, as desired.

In operation, filter sheet 80 performs the function of a draw sheet which also allows free flow of fluids away from the patient and into the basin member of the waste managing means. Thus, the material forming filter sheet 80 should have a very high tensile strength that is at least equal to the tensile strength of current hospital draw sheets. The material forming filter sheet 80 also should have a very small coefficient of friction, small enough so that it is equal to or less than the coefficient of friction of a material such as HY.TEX ™ fabric, which is available from Consoltex of Montreal, Canada. This small coefficient of friction facilitates use of filter sheet 80 when it is functioning as a draw sheet.

Desirably, as shown in FIG. 2 for example, filter sheet 80 has reinforced edges 86 forming a continuous border around the portion containing small pores 82. As shown in FIG. 2 for example, reinforced openings 87 desirably are formed in border portions 86 on opposite sides of filter sheet 80 and configured to accommodate the hands of an operator to facilitate the draw sheet function. In an alternative embodiment shown partially in FIGS. 2 and 2A for example, filter sheet 80 can be provided with handles or grips 88, which can be secured to the exterior surfaces of opposite border portions 86 of filter sheet 80 by such conventional means as sewing, rivets, adhesives, etc.

The filter sheet should be capable of withstanding multiple washings and should be formed of material that in addition to being antimicrobial, is also bacteriostatic, hypoallergenic, flame retardant, odor resistant, and sufficiently hydrophobic so as to dry quickly. Filter sheet 80 should be formed of material that is stain resistant for repeated use in an environment that anticipates staining from urine, from fecal matter, and from fluids normally used in the hospital environment. At least the liquid permeable portion of a suitable filter sheet 80 is formed of a monofilament plastic such as nylon or polyester filter mesh fabric of 114 pick. Antimicrobial properties can be built into the filter sheet. For example, antimicrobial material could be impregnated into the plastic material forming the filter sheet.

In accordance with the present invention, a means can be provided for detachably securing the filter sheet against movement away from a position resting over the basin member. However, the detachably securing means also should enable the hospital staff to release the filter sheet from its secured position by the use of only a small amount of manual effort. The filter sheet's detachably securing means desirably can be provided in the form of mechanical fastening means such as snaps or hook-and-loop substrates. As embodied herein and schematically shown in FIGS. 2 and 2A for example, a plurality of snaps 90 is mateable with a second plurality of snaps 92 mounted on the exterior surfaces of side panels 94, which are themselves attached to the exterior endwall surfaces 238 of an adaptor shell 228 (described hereafter). The fastening end of filter sheet snaps 90 desirably can be exposed for service on the interior surface of border portions 86 of filter sheet 80. As shown in FIG. 2A for example, filter sheet snaps 90 attach to panel snaps 92 mounted on the outside surfaces of side panels 94. The snaps 90, 92 engage one another to hold filter sheet 80 in place, yet permit easy disengagement of filter sheet 80 by grasping reinforced openings 87 or handles 88 and pulling away from the adaptor shell whenever use of filter sheet 80 as a draw sheet is desired.

Moreover, as shown in FIGS. 2 and 2A for example, the inside surfaces of side panels 94 are provided with a plurality of snaps 96, which are detachably attachable to a plurality of mating snaps 97 disposed on the peripheral walls 238 of legs 236 (described hereafter) of air inflated cushions 234 (described hereafter) or on the endwalls of air sacks 44 or on the endwalls of turning sacks 270 (described hereafter). Each corresponding pair of snaps 96, 97 engages one another through an attachment opening 83 defined through a side flap portion 85 of basin member 62 and thereby attaches basin member 62 to an adaptor shell 228 (described hereafter).

In still further accordance with the present invention, a means can be provided for removing the waste materials that are caught by the catching means. The waste removing means is configured and disposed so as to be in communication with the catching means. As embodied herein and shown in FIGS. 1, 2 and 9 for example, the waste removing means desirably includes at least one waste removal conduit 98. Waste removal conduit 98 preferably is formed of polyvinyl chloride (PVC) flexible tubing that desirably is sized with a three-quarter inch interior diameter and a circular transverse cross-section. As shown in FIG. 2 for example, waste removal conduit 98 has one end configured to be connected in communication with at least one drain opening 66 of basin member 62. Desirably, waste removal conduit 98 is disposed so as to be connected to the free end of cylindrical portion 63 (FIGS. 17 and 18) of drain fitting 67. Waste removal conduit 98 is configured to be easily attachable and detachable from drain fitting 67 for ease of cleaning and servicing. As embodied herein and shown in FIG. 9 for example, free end 81 of drain fitting 67 desirably fits inside one end of waste removal conduit 98 and is secured therein by a conventional band hose clamp 70, such as might be used to secure the radiator hose of an automobile. As schematically shown in FIG. 9 for example, waste removal conduit 98 desirably is vertically disposed in order to take advantage of the assistance provided by the force of gravity and is configured so as to provide a straight pat that does not contain any steps or shelves where waste might accumulate.

As embodied herein and shown schematically in FIG. 9 for example, the removing means also desirably includes a holding reservoir 100 connected in communication with the opposite end of waste removal conduit 98. Holding reservoir 100 defines a liquid impermeable plenum which desirably has a capacity of one gallon.

As embodied herein and shown schematically in FIG. 9 for example, the removing means can further include a vacuum blower 102 that is configured and disposed so that it can create a suction force in at least the catching means and waste removal conduit 98. As shown in FIG. 9 for example, vacuum blower 102 is connected via a conduit 132 in communication with holding reservoir 100, which enables vacuum blower 102 to communicate indirectly with waste removal conduit 98 connected in communication with holding reservoir 100 via a removal conduit extension 99 and a flow diverter valve 108 (described below). Desirably, vacuum blower 102 is designed to run at 27 cubic feet per minute at a vacuum pressure of 40 inches of water and is powered by a one phase, one horsepower motor operating from a 110 volt 60 cycle alternating current power source. Vacuum blower 102 desirably is set up for two speed active operation, a relatively low speed and a relatively high speed. The exact speeds will depend on the configuration of the other parameters of the waste management system. The higher speed provides the suction force for removing waste materials.

In accordance with the present invention, the vacuum blower operates essentially continuously at the lower speed for the purpose of providing air flowing beneath the occupant of the waste management system. The constant removal of air from beneath the occupant assists in the control of odor and moisture beneath the occupant.

Operation of vacuum blower 102 desirably is determined by a controller 164. A suitable controller 164 can be provided by an array of relays programmed in an appropriate logic circuit, but desirably is provided by a suitably programmed 8051 series microprocessor.

In still further accordance with the present invention, the removing means also can include a portable, manually directed suction device. As embodied herein and shown schematically in FIGS. 1 and 9-11 for example, a suitable portable, manually directed suction device can be provided in the form of a vacuum wand generally designated by the numeral 104. The free end of vacuum wand 104 can be a tip 112 formed of a rigid plastic material in the shape of a flattened horn. Alternatively, a soft, flexible, and smooth plastic material can be used to form tip 112. A friction fit mechanical connection between tip 112 and wand 104 permits manual detachment of tip 112 from wand 104. In some embodiments, tip 112 can be disposable. Moreover, as shown schematically in FIG. 9 for example, suction force is provided to tip 112 of vacuum wand 104 by connecting same via a suction line 106 and a flow diverter valve 108 (described below in communication with holding reservoir 100 and vacuum blower 102.

As shown schematically in FIGS. 1 and 9-11 for example, suction line 106, which connects vacuum wand 104 to holding reservoir 100, is desirably formed of flexible plastic, which desirably is reinforced by plastic spiraling 110 formed in a corrugated helix pattern in the outside of line 106 in order to prevent kinking of the suction line, especially when waste is being vacuumed. A suitable suction line 106 is provided by a 6.5 foot length of flexible three-quarter inch internal diameter PVC TYGON ™ tubing (available from Norton Performance Plastics of Akron, Ohio) with a bend radius of 1.5 inches.

Figure 21:
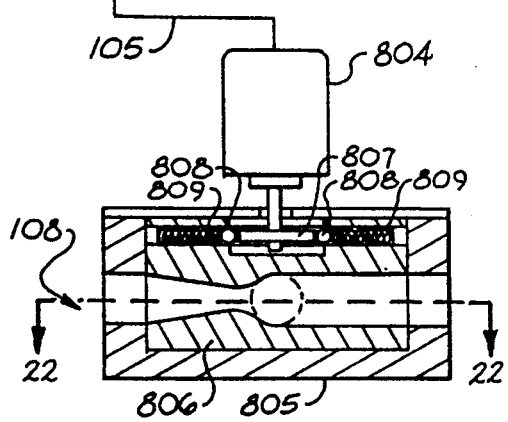
FIG. 21 schematically illustrates components of a preferred embodiment of the present invention from a side cross-sectional view.
Figure 22:
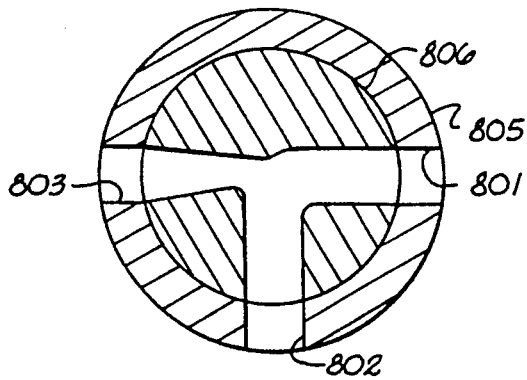
FIG. 22 schematically illustrates components of a preferred embodiment of the present invention from a top cross-sectional looking in the direction of arrows 22—22 in FIG. 21.

As embodied herein and shown schematically in FIGS. 9, 21 and 22 for example, flow diverter valve 108 desirably has three ports 801, 802, 803. Port 801 is connected to vacuum wand 104 via suction line 106. Port 802 is connected to holding tank 100 via extension 99 of waste removal conduit 98. Port 803 is connected in communication with basin member 62 via waste removal conduit 98 and drain fitting 67. Diverter valve 108 can be configured in one of two flow paths by operation of an electric motor 804, which is controlled by controller 164. In addition to motor 804, flow diverter valve 108 includes a valve body 805, a valve spool 806, a slip clutch hub 807, and a pair of spring-biased ball plungers. Each spring ball plunger includes a spheroidal member 808 mounted at the end of a coiled spring 809 which biases the spheroid into a semi-spherical cavity defined in slip clutch hub 807.

Operation of motor 804 rotates valve spool 806 between a first position and a second position. In a first position, which is schematically shown in FIG. 22 for example, diverter valve 108 provides a flow path in which each of basin 62, holding reservoir 100, suction line 106 of vacuum wand 104, and vacuum blower 102 are connected in communication with one another. This first position of diverter valve 108 thus disposes vacuum blower 102 so as to be able to create a suction force at tip 112 at the free end of vacuum wand 104 as well as a relatively smaller suction force at basin member 62. In this first position with the blower described above, roughly 20 cubic feet per minute (CFM) suction flow is applied to vacuum wand 104 and 10 CFM is applied to basin member 62. In a second position, which is not shown in the Figs., diverter valve 108 provides a flow path in which each of basin 62, holding reservoir 100, and vacuum blower 102 are connected in communication with one another. This second position of diverter valve 108 thus disposes vacuum blower 102 so as to be able to create a suction force that removes waste from basin 62 and pulls this removed waste into holding reservoir 100 without providing any suction force to vacuum wand 104. Moreover, since orientation of diverter valve 108 to assume the first position divides the suction provided by vacuum blower 102 between two paths, the suction force provided to vacuum wand 104 in the first position of diverter valve 108 is desirably less than the suction force provided to basin 62 alone when diverter valve 108 assumes the second position.

Desirably, the suction provided by vacuum wand 104 is intended to remove liquid waste such as urine and rinse solution, viscous waste such as running stool or loose stool, and solid waste that does not exceed the opening size of the vacuum tip 112. Desirably, the opening size of vacuum tip 112 is 0.4 inches wide by 2.5 inches long at the free end. However, at the attachment (or throat) end of tip 112, the length of the opening of tip 112 reduces to about 0.7 inch. Thus, larger solid waste, such as larger formed fecal matter, will not be able to be vacuumed directly with wand 104. In order to be vacuumed, the larger formed waste must first be eroded by the rinse spray into a semi-liquid condition. The maximum size fecal matter able to be suctioned in the configuration of the vacuum blower and tubing described above, is approximately 0.4 inches.

Figure 11:
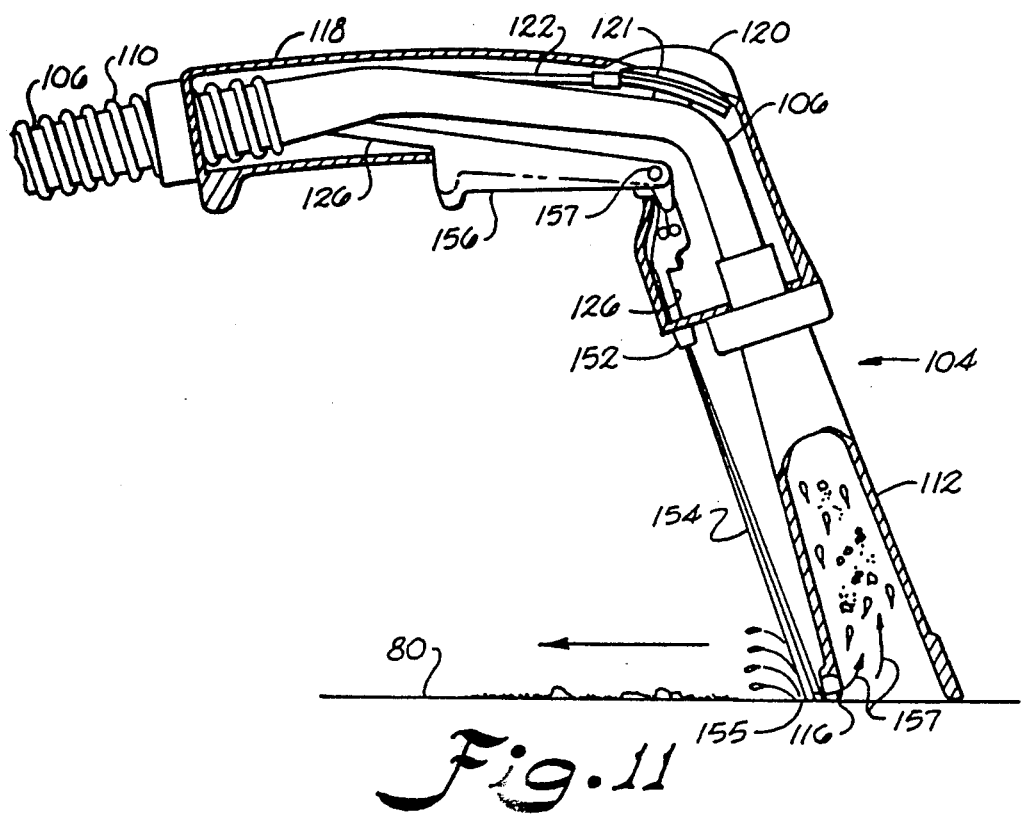
FIG. 11 schematically illustrates components of a preferred embodiment of the present invention from a side plan view with portions cut away.

Moreover, as shown schematically in FIGS. 9 and 11 for example, the provision of a plurality of safety louvers 116 at the underside surface of the free end of tip 112 is designed so that suction can be applied via tip 112 to suck off rinse solution, other fluids, and small particulates from the filter sheet 80. Safety louvers 116 also provide vacuum reduction, splash back protection from liquid spray impinging on the filter sheet 80, and lubrication of the inside of the vacuum tip with liquids, such as rinse solution (explained more fully hereafter) sucked into vacuum tip 112 through louvers 116 to help prevent sticking of fecal matter inside the vacuum tip.

Desirably, vacuum wand 104 can be maneuverable with one hand. As shown schematically in FIGS. 1 and 11 for example, vacuum wand 104 desirably is provided with a pistol grip 118 and has an activation mechanism that includes an "on/off" suction switch 120 by which the user's thumb can turn suction on and off while holding the wand in one hand Preferably, vacuum wand 104 itself is electrically isolated insofar as it does not contain any electrical components. The absence of electrical components in vacuum wand 104 eliminates the danger of transmitting electrical shocks to the patient or operator via vacuum wand 104. Thus, suction switch 120 in wand 104 desirably is a pneumatic switch.

As illustrated schematically in FIG. 11 for example, suction switch 120 can include a small flexible bladder 121 connected in communication with a pneumatic line 122. Pneumatic line 122 desirably is a length of one sixteenth inch internal diameter PVC TYGON TM tubing. Actuation of suction switch 120 occurs when the operator's thumb applies pressure to suction switch 120 which squeezes bladder 121. When the bladder is squeezed, a signal in the form of a pressure pulse travels via pneumatic line 122 to a pressure transducer 124 (FIG. 9), which is disposed at a location that is remote from wand 104 in order to eliminate electrical components from wand 104. Pressure transducer 124 converts this pressure signal into an electrical signal. As schematically shown in FIG. 9 for example, pressure transducer 124 is connected to controller 164.

Upon receipt of the pressure pulse from bladder switch, transducer 124 sends an electrical signal to controller 164, which responds to this electrical signal by sending two control signals. One of the control signals is sent via a cable 105 to motor-operated flow diverter valve 108 so that valve 108 configures itself to connect vacuum blower 102 in a manner that provides a suction force to remove waste from tip 112 of vacuum wand 104 and basin 62 and transports this removed waste into holding reservoir 100. The other control signal is sent via a cable 224 to operate vacuum blower 102 at high speed. The result of these two control signals is to provide suction in suction line 106 and moderate suction in waste removal conduit 98.

When the operator wants to discontinue suction through wand 104, the operator again presses bladder switch 120. Another pressure signal is transmitted via pneumatic line 122 to controller 164 via pressure transducer 124, and controller 164 is programmed to send a time delayed control signal via cable 105 to flow diverter valve 108 to reorient this valve 108 such that suction is removed from vacuum wand 104 and the normal amount of suction is applied to basin 62 from blower 102. Controller 164 is programmed to return vacuum blower 102 to low speed operation beginning about 20 seconds after flow diverter valve 108 removes suction from line 106.

In further accordance with the present invention, a means can be provided to prevent operation of the vacuum blower from drawing wastes out of the removing means and backing same into the vacuum blower conduits which enable the vacuum blower to communicate with the interior of the holding reservoir. The latter contamination is undesirable, as it could lead to the introduction of undesirable liquids, particulates, and gasses into the vacuum blower 102 and possibly into the patient environment. For example, the liquids and particulates could hinder operation of the blower or damage the blower. As embodied herein and shown schematically in FIG. 9 for example, the means for preventing waste back-up into the vacuum blower conduits, desirably includes a liquid level sensor 107 connected via an electric cable 109 in communication with controller 164, which in turn is connected so as to be able to control operation of vacuum blower 102. Liquid level sensor 107 is disposed so as to be able to detect liquid at a level within holding reservoir that is just below where the vacuum conduit 132, which leads between reservoir 100 and blower 102, enters holding reservoir 100. When sensor 107 detects liquid at this level, sensor 107 sends a liquid detection signal in the form of an electrical signal to controller 164. Controller 164 is preprogrammed so that upon receipt of this liquid detection signal from sensor 107, controller 164 deactivates operation of vacuum blower 102. In this way, controller 164 prevents operation of vacuum blower 102 when the waste level sensor 107 detects that holding reservoir 100 has become filled to a predetermined proportion of its capacity. The deactivation of vacuum blower 102 prevents suction from waste removal conduit 98 and/or a vacuum wand 104 from attempting to introduce additional wastes into a holding reservoir 100 which is nearing its capacity and thus disposing waste liquids very near to the entrance of the vacuum conduit 132 which leads to vacuum blower 102.

In further accordance with the present invention, the removing means can include means for controlling odor. As embodied herein and shown schematically in FIG. 9 for example, the odor control means can include a housing in the form of a cannister 136 containing an odor filter 138 such as activated carbon. Cannister 136 can be disposed in the conduit 132 that connects vacuum blower 102 to holding reservoir 100. As shown in FIG. 9 for example, vacuum blower 102 preferably can be disposed between cannister 136 and holding reservoir 100 so that vacuum blower 102 exhausts to atmosphere via the odor control means. Alternatively, cannister 136 can be disposed between the vacuum blower 102 and holding reservoir 100. In this latter configuration, the vacuum blower communicates with the holding reservoir via the odor control means. A suitable cannister 136 can be formed of rigid plastic or metal material capable of containing 2.3 pounds of activated charcoal and having a removable cover 140 to permit servicing of the odor control material and replacement of same at appropriate time intervals.

In yet further accordance with the present invention, the removing means can include means for cleansing. The cleansing means desirably provides a spray of a liquid that can be used to rinse, cleanse, disinfect, wound irrigate or the like. The cleansing means desirably can be directed and operated by one hand of the operator. The cleansing means desirably provides the liquid spray in a controlled manner so that the spray will not be likely to cause skin trauma to the patient being cleansed nor undue splashing from the surface being cleansed, yet provides sufficient pressure for effective cleansing action of the surface targeted for cleansing.

Figure 26:
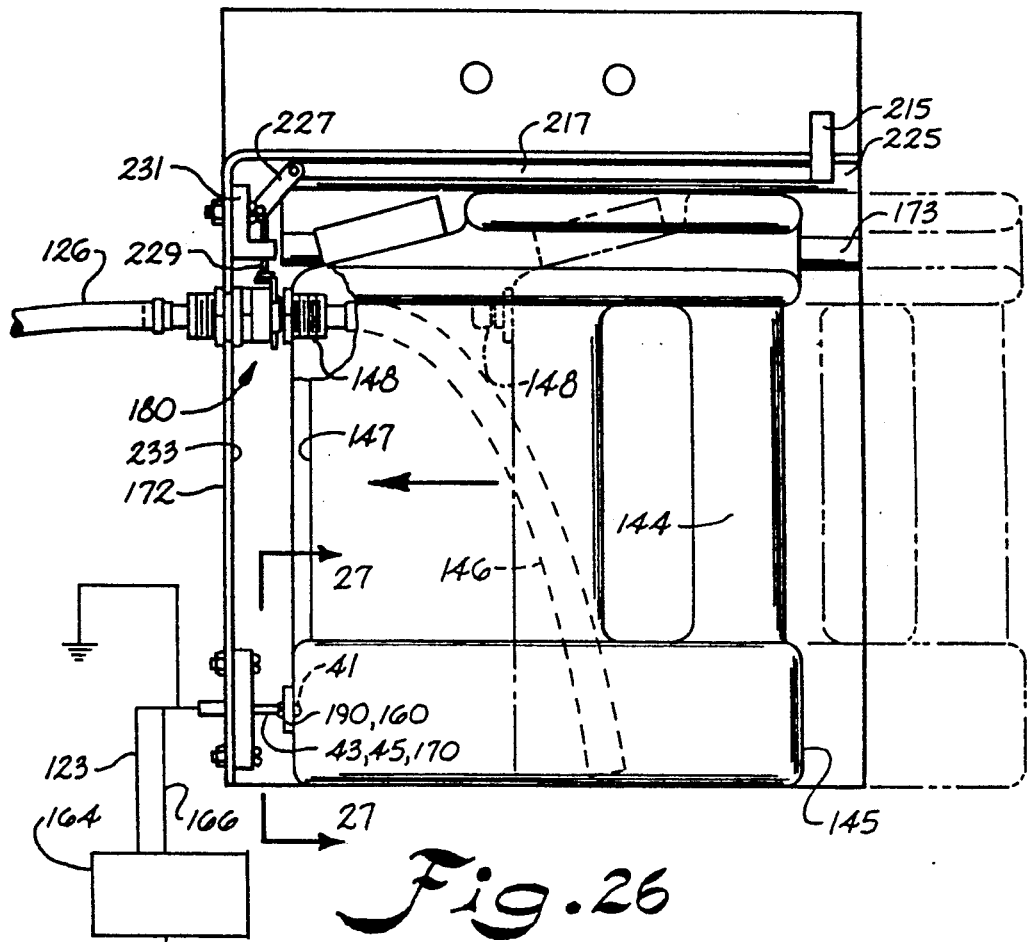
FIG. 26 schematically illustrates components of a preferred embodiment of present invention from a side plan view with portions indicated in phantom by the dashed lines and portions cut away.

As embodied herein and shown in FIGS. 6, 26, 28 and 29B for example, the cleansing means can include a rinse solution container 142 in the form of a rinse jug 142 having a handle 144 defined in the front endwall 145 of jug 142. Jug 142 desirably can be formed of liquid impermeable material such as high density polyethylene (HDPE), or polypropylene, or polycarbonate, or any similar rigid plastic material. Depending on the embodiment, the rinse solution container can be configured to be removably securable to the patient support apparatus (FIG. 1) or to a service cart 256 (FIGS. 12, 12A, 15 and 16 for examples). Rinse solution container 142 can be provided with a capacity of one-half gallon and can be filled with various rinse solutions such as tap water, saline rinse, PERI-WASH TM solution, and the like, via a fill opening 149 which is defined at the free end of a circularly cylindrical annular member 151. The annular member has an exterior surface which can be provided with screw threads so that fill opening is removably sealable by means of a screw-on threaded cap. As schematically shown in FIG. 26 for example, rinse jug 142 includes a siphon tube 146 (shown in phantom by the dashed lines) having an open mouth disposed near the bottom of jug 142 and an opposite end connected to an inlet/outlet valve 148 defined in or attached to the upper portion of the back endwall 147 of jug 142.

As embodied herein and shown in FIGS. 9, 11 and 26 for example, the cleansing means also can include a rinse solution conduit 126 having a free end carried by vacuum wand 104 and an opposite end connected so as to be in communication with valve 148 (FIG. 26) and siphon 146 of rinse solution container 142. A suitable tubing for rinse solution conduit 126 is provided by one-eighth inch internal diameter PVC TYGON TM tubing. Desirably, as shown in FIG. 9 for example, rinse solution conduit 126 is disposed within suction line 106. As shown in FIG. 11 for example, one end of conduit 126 exits a portion of line 106 disposed within the interior of vacuum wand 104. The opposite end of conduit 126 exits the portion of line 106 that is in the vicinity of where line 106 becomes connected to port 803 of flow diverter valve 108.

As embodied herein and shown schematically in FIGS. 9 and 11 for example, the cleansing means can include a rinse spray nozzle 152, which desirably can be provided on vacuum wand 104. Rinse spray nozzle 152 desirably is connected in communication with the free end of rinse solution conduit 126 and is configured to produce a fan-shaped pattern (FIG. 11) of rinse liquid 154. As schematically shown in FIG. 11 for example, rinse spray nozzle 152 desirably is disposed on wand 104 and configured so that this fan-shaped pattern of rinse solution 154 is directed to contact a site 155 on the target surface, such as filter sheet 80, just behind louvers 116 on Vacuum tip 112. In this Way, the vacuum force (schematically indicated by the arrows 157 inside tip 112 in FIG. 11) applied at the free edge of tip 112 pulls liquids through louvers 116 and reduces the amount of liquids that can collect at the target site 155 of the rinse liquid spray and be splashed by the spray of rinse liquid 154. As shown in FIG. 11 for example, rinse spray nozzle 152 desirably is configured so that it does not come into contact with vacuum wand suction tip 112, and this assists in the prevention of contamination or soilage. However, in some embodiments, nozzle 152 may be both removable and disposable.

In addition, the cleansing means forming a part of the removing means can further include a rinse pump. As shown schematically in FIG. 9 for example, a rinse pump 150 desirably is connected so as to be able to pump rinse solution from rinse solution container 142 through rinse solution conduit 126. A suitable rinse pump 150 is provided by a nutating head pump designed to flow 1.2 gallons per minute at 1 psi and powered by a 110 volt AC 60 cycle one phase electric motor. Liquid flow rates of rinse fluid are controlled by operation of rinse pump 150 to be at a safe velocity and pressure that will not debride open wounds or cause any skin trauma. Desirably, the pressure of the rinse solution should not be so great as to apply a dynamic impact pressure exceeding 8 psi on the patient's skin. The velocities and pressures of the rinse liquid provided by rinse pump 150 are nonetheless adequate to clean waste from the patient and filter sheet 80. Desirably, the rinse solution flow rates will be low enough to minimize or prevent splashing.

As schematically illustrated in FIG. 11 for example, the cleansing means can include a trigger-type rinse control valve 156 that provides rinse solution to rinse spray nozzle 152. Rinse control valve 156 desirably is a valve which can be operated mechanically to allow rinse solution, which is provided under pressure by pump 150 from rinse solution container 142 to conduit 126, to be dispensed through nozzle 152. Desirably, rinse control valve 156 is provided in the form of a lever pivotable about a pin 157 on the hand held portion of vacuum wand 104 and is spring-biased to crimp conduit 126 and prevent flow of rinse liquid to nozzle 152. Manual squeezing of trigger 156 toward pistol grip 118 works against the spring to uncrimp conduit 126 and provide rinse solution to nozzle 152.

In accordance with the present invention, means are provided so that the rinse pump automatically provides rinse solution to the vacuum wand whenever the vacuum wand is going to be used by the operator. As embodied herein, the automatic activation means for the rinse pump can include a microswitch which is activated to turn on the rinse pump whenever the operator tries to use the vacuum wand. As shown schematically in FIGS. 1 and 10 for example, vacuum wand 104 (without tip 112) and its associated suction line 106 desirably are stored when not in use. After use of wand 104, the soiled tip 112 is discarded before the wand is stored in a storage compartment 111, which is desirably provided at the footboard 113 of the bed 30. In alternative embodiments, a similar storage compartment can be provided as part of a service part 256 (FIGS. 12, 12A, 15 and 16 for examples). Access to storage compartment 111 desirably can be provided via a top mounted door 115 that swings open from the top down. Upon opening door 115, a microswitch 109 activates and sends an alert signal to a controller 164 which is electrically connected to rinse pump 150 via cables 226. Microswitch 109 can be disposed either on door 115 or within compartment 111, as desired. Controller 164 is programmed so that when controller 164 receives an alert signal from microswitch 109 indicating that the operator has obtained access to vacuum wand 104, controller 164 sends an electrical control signal which activates rinse pump 150 to provide rinse solution to vacuum wand 104. Thereafter, manual activation of rinse trigger switch 156 releases a spray of rinse solution 154 (FIG. 11) from spray nozzle 152.

Figure 10:
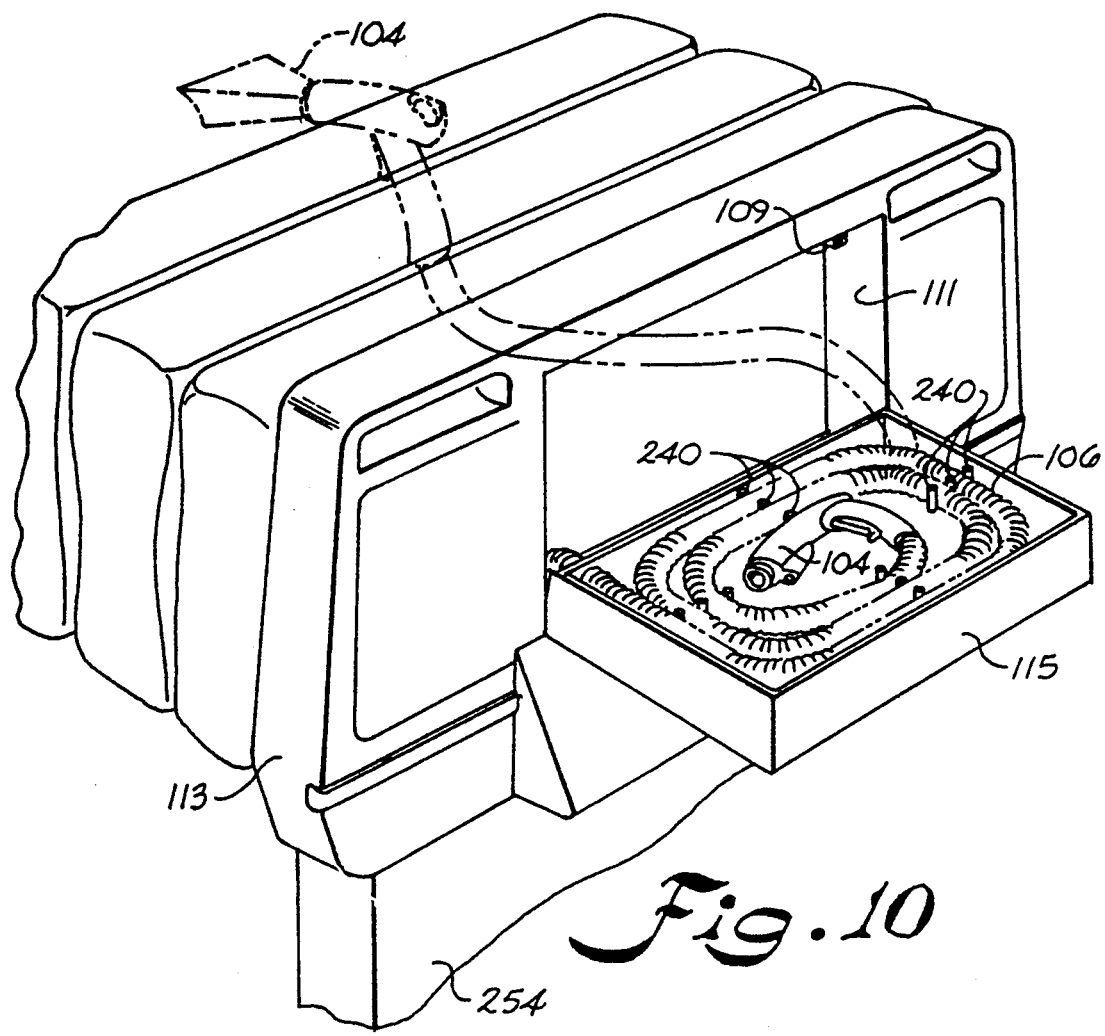
FIG. 10 schematically illustrates components of a preferred embodiment of the present invention from an elevated perspective view.

As shown schematically in FIG. 10 for example, suction line 106 is desirably secured in storage compartment 111 by friction fit between a plurality of pairs of opposed guide members 240 disposed in door 115 in a pattern that determines the wrap direction of line 106. In an alternative preferred embodiment, instead of the posts shown in FIG. 10 for guide members 240, the guide members desirably are configured as molded recesses which extend around the floor of door 115 and are shaped to receive the cylindrical tubing of suction line 106. Moreover, in an alternative preferred embodiment of the rinse pump automatic activation means, microswitch 109 can be disposed and configured so that it activates pump 150 when suction line 106 is removed from between a pair of guides 240 instead of when door 115 is opened.

During a cleansing operation, rinse solution at a low pressure is ejected from the center portion of the spray nozzle 152 to assist washing the filter sheet 80 and/or the patient. The pressure of this rinse solution is not so great that it might damage any wounds on the patient, bed sores on the patient, or peeling burns or other skin on the patient. After the majority of rinse liquids and waste materials have been vacuumed away through vacuum wand 104 at the conclusion of each waste-producing episode, the filter sheet desirably is toweled dry.

Figure 28:
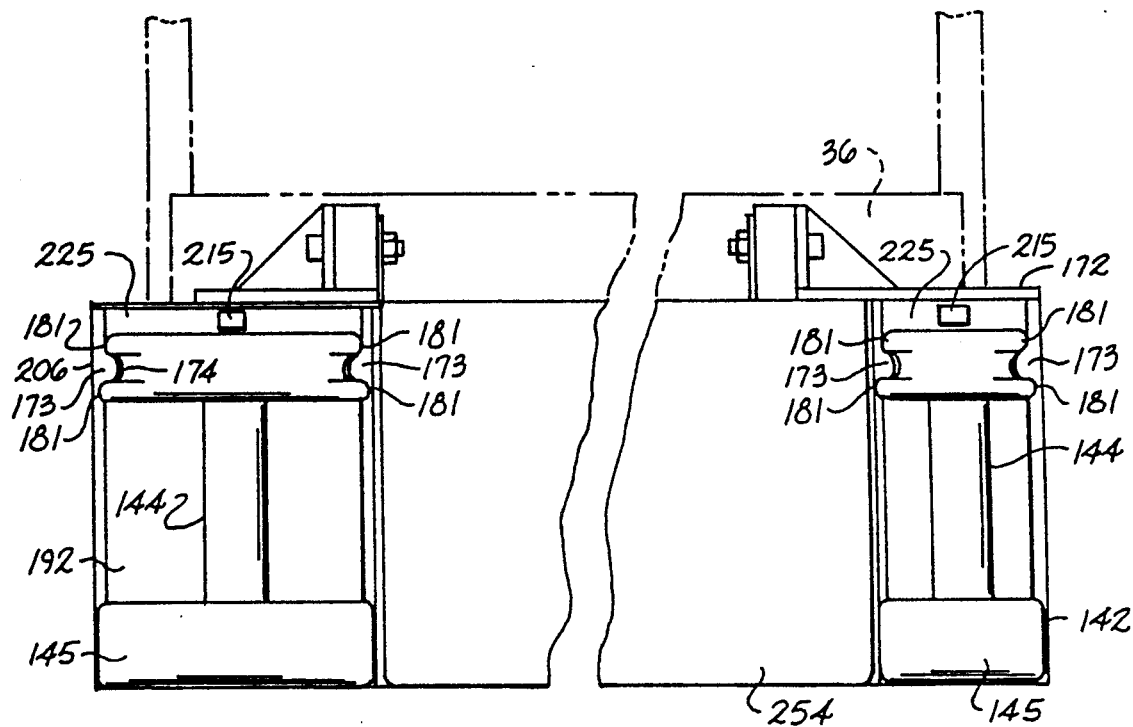
FIG. 28 illustrates a front plan view of components of a preferred embodiment of the present invention with portions broken and other portions shown in phantom by dashed lines.

In still further accordance with the present invention, a means can be provided for receiving the rinse solution container. As embodied herein and schematically shown in FIGS. 26 and 28 for example, the rinse container receiving means desirably includes a first housing 172 configured for receiving rinse solution container 142. Depending upon the particular embodiment of the present invention, first housing 172 can be provided as part of a bed, or as part of a service cart 256, or as part of an emergency treatment table, or the like. For example, first housing 172 can be carried by the bed frame beneath the footboard and fixed to upper frame 36 as shown generally in FIG. 28 for example. As schematically shown in FIG. 28 for example, first housing 172 desirably includes a slide receptacle 173 which slidably and nonrotatably receives a mating groove member 174 (FIGS. 6, 28 and 29B) defined by a pair of opposed overhanging flanges 181 which are formed as part of or connected to the upper portion of the exterior sides walls of rinse jug 142. As shown in FIG. 28 for example, insertion of opposed inward-facing elongated cam members of receptacle 173 into groove member 174 of rinse jug 142 ensures proper alignment of rinse jug 142 with respect to first housing 172 whenever the rinse jug is secured by first housing 172.

As shown schematically in FIGS. 12 and 12A or 15 and 16 for example, the first housing can be formed as part of the upright frame 258 (FIGS. 15 and 16) or low profile portion 264 of a mobile service cart 256. In some such embodiments, the rinse solution container 142 can be provided as a permanent part of the service cart. As shown schematically in FIG. 16 for example, a fill hose 143 is provided for introducing additional rinse solution into rinse jug 142 and is desirably held within the service cart by a bracket 141.

In still further accordance with the present invention, the first housing includes means for automatically connecting the rinse solution container in communication with the rinse spray nozzle of the vacuum wand when the first housing receives the rinse solution container. When the first housing receives the rinse solution container, the rinse container connecting means becomes engaged, and the rinse solution jug thereby automatically becomes engaged in communication with the rinse spray nozzle of the vacuum wand. Moreover, the rinse container connecting means is configured to prevent any of the rinse solution from escaping from the connecting means when the connecting means is disengaged and the first housing disengages from the rinse solution container.

As embodied herein and shown schematically in FIGS. 14 and 26 for example, the rinse container connecting means desirably includes a dripless connector, which is generally designated by the numeral 180 in FIG. 14 and forms inlet/outlet valve 148 shown in FIG. 26. As schematically shown in FIG. 14, dripless connector 180 includes both a male member 182 and a female member 184, either one of which being provided as inlet/outlet valve 148 (FIG. 9) attached to the exterior of rinse jug 142. The other of the male and female members of dripless connector 180 is formed as part of or attached to the portion of the exterior of first housing 172 that is connected in communication with rinse solution conduit 126. Each of male member 182 and female member 184 includes a hose fitting 183 which can be connected to the end of a hose such as rinse solution conduit 126 or siphon tube 146, depending whether the member 182 or 184 is attached to first housing 172 or rinse jug 142. Moreover, each of male member 182 and female member 184 includes a spring 186 disposed and configured to bias a poppet type closure 187 to seal the respective opening 188 to its respective passageway 189 immediately upon being disengaged from one another, thus rendering connector 180 dripless.

The receiving means for the rinse solution container also desirably includes means for positively locking the rinse solution container into the receiving means. As embodied herein and illustrated in FIGS. 14 and 26 for example, connector 180 also desirably is formed as a quick-disconnect type connector, which automatically snaps together or separates by the application of moderate manual force to a mechanical locking means. Thus, the positive locking means desirably includes a positive locking mechanism formed as part of dripless connector 180. As shown in FIG. 14 for example, connector 180 is provided with a quick-disconnect mechanism that includes a locking spring 199 configured and disposed to bias a locking member 200 which is configured with a ring portion 208 (FIG. 14B) that is slidably received in a locking slot 201 formed to extend circumferentially in a transverse direction within female member 184. When male member 182 is inserted into female member 184, the inner edge 205 of ring portion 208 of locking member 200 is engaged by a circumferential groove 202 formed in the exterior of male member 182. Such engagement provides a positive locking force which prevents unwanted movement of rinse jug 142 from first housing 172. Disengagement of locking mechanism involves pressing a release flange 203 formed as part of locking member 200. When the release flange 203 is pressed, locking member 200 moves against its biasing spring 199 and out of the circumferential groove 202 of male member 182. At the same time, the springs 186 which bias the poppet closures 187 in the male and female members 182, 184 provide forces in a direction that separates male member 182 from female member 184, thus providing a quick-disconnect force. In addition, as shown in FIGS. 14A and 14B, when ring portion 208 moves to compress locking spring 199, a pin biasing spring 207 moves a tapered bottle nose pin 209 out of a slot 211 defined in ring portion 208 and provides a force which acts in a direction that separates male member 182 from female member 184, thus providing a quick-disconnect force.

As shown in FIGS. 26 and 28 for example, release flange 203 is pressed when the operator pushes a release button 215 disposed near and above the entrance to slide receptacle 173. Release button 215 is connected to one end of an elongated push rod 217 which is confined within a narrow channel 225 disposed above and extending along the length of slide receptacle 173. The opposite end of push rod 217 is pivotally connected to one end of an arm 227. The opposite end of arm 227 is pivotally connected to one end of a plunger 229 which is slidably mounted to move in the vertical direction in a mounting block 231 attached to the back wall 233 of first housing 172. The opposite end of plunger 229 is configured and disposed to press against release flange 203 when the operator pushes release button 215 toward back wall 233 of first housing 172.

A suitable embodiment for dripless, quick-disconnect type connector 180 is a connector that is available from Colder Products Company as model PLCD-160-06 for the female member 184 and PLCD-420-06 for the male member 182. Desirably, dripless, quick-disconnect connector 180 is located in the upper portion of the back endwall 147 of rinse solution jug 142. Accordingly, rinse jug 142 can be removably securable to a patient support apparatus or to a service cart 256 via the first housing, the connecting means, and the coupling means.

Figure 26A:
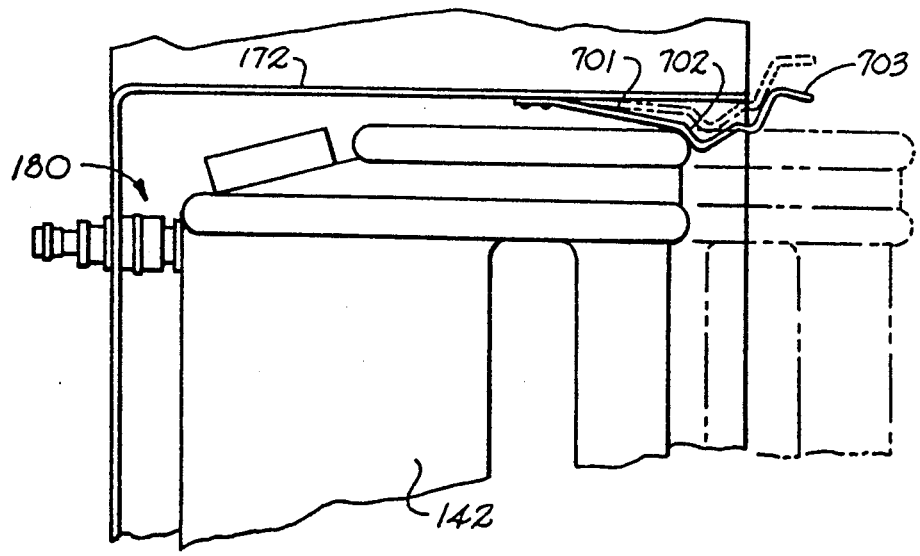
FIG. 26A schematically illustrates a side plan view of components of a preferred embodiment of the present invention with portions broken and other portions shown in phantom by dashed lines to illustrate two alternative positions of certain components.

In an alternative preferred embodiment of the positively locking means, and as shown schematically in FIG. 26A for example, a positive locking mechanism is provided in the form of a flat spring 701 disposed above slide receptacle 173 in narrow channel 225 between first housing 172 and slide receptacle 173. Flat spring 701 has one end attached to first housing 172 and defines a detent 702 near the free end thereof. Detent 702 is biased into a position that secures jug 142 into first housing 172 and male member 182 into female member 184 of connector 180. A release flange 703 defined at the free end of spring 701 can be lifted by the operator to the position shown in dashed lines in FIG. 26A to permit withdrawal of jug 142. In this alternative preferred embodiment, connector 180 would be modified to eliminate the positive locking mechanism that includes locking spring 199 and locking member 200 configured with ring portion 208 and release flange 203 as shown in FIGS. 14A and 14B. In this alternative preferred embodiment, release button 215, elongated push rod 217, and the remaining elements of this release mechanism can be eliminated.

Figure 27:
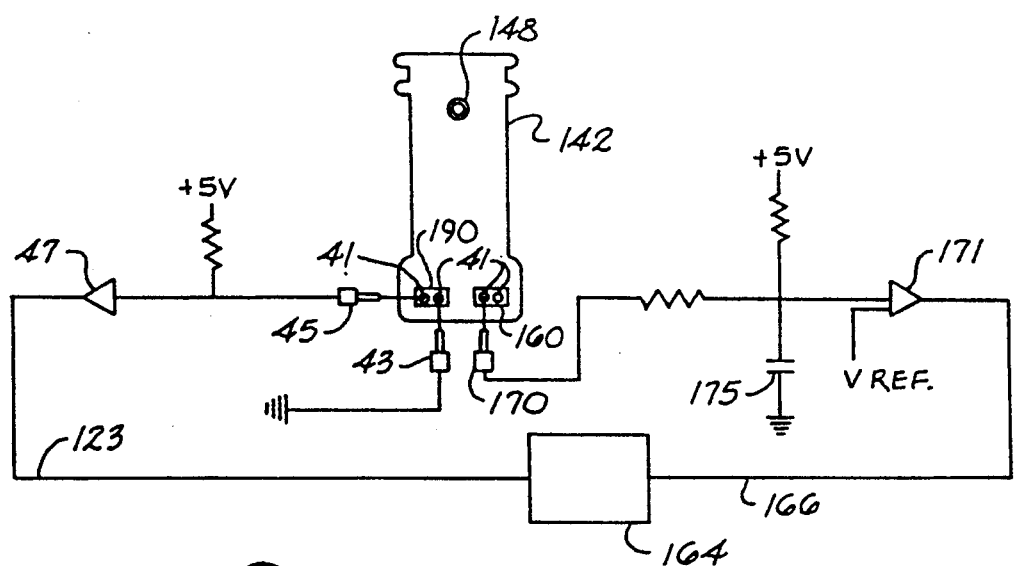
FIG. 27 is a schematic representation of components of a preferred embodiment of the present invention.

In accordance with the present invention, a means can be provided for detecting when the rinse solution container is securably received by the first housing and providing a signal upon detecting such securable receipt or the absence of same. Desirably, the securably received detecting means is connected to provide its signal to the controller, which can indicate receipt of such signal by actuating an indicator means of a control panel. As embodied herein and shown schematically in FIGS. 9, 27 and 29B for example, the securably received detecting means can include a first contact plate 190 that is electrically conducting and disposed on the exterior of the back endwall 147 of rinse jug 142 at a level near the bottom of jug 142. Plate 190 is mounted to jug back endwall 147 by at least one electrically conducting attachment screw 41, which extends into the interior of rinse jug 142 and contacts the rinse solution contained therein. As shown schematically in FIG. 26 for example, a pair (only one is visible in the FIG. 26 view) of electrical contact probes 43, 45 is disposed to extend from the back wall 233 of first housing 172, which back wall 233 faces opposite the back endwall 147 of jug 142 when rinse solution jug 142 is securely received by first housing 172. Each electrical contact probe is desirably a spring loaded probe with a waffle tip configuration such as is available from Interconnect Devices, Inc. of Kansas City, Kans. The waffle tip configuration (not shown) provides multiple point electrical contact. As schematically shown in FIG. 27 for example, one probe 43 is connected to ground, and the other probe 45 is connected to a gate circuit element 47 with a positive reference voltage connected between gate 47 and gate probe 45. These probes 43, 45 are disposed and configured so that they do not make contact with first contact plate 190 unless male member 182 of connector 180 is locked into female member 184. When both ground probe 43 and gate probe 45 touch first contact plate 190, they complete an electrical circuit that shorts the reference voltage to ground through first plate 190 and ground probe 43, and gate 47 sends a first signal to controller 164 via cable 123 indicating that both probes are touching plate 190.

Upon receipt of this first signal, controller 164 can be programmed to activate an indicator or not, depending on how the indicator scheme is designed to alert the operator for the secured presence of rinse jug 142. For example, when both probes fail to touch first contact plate 190, gate 47 continues to receive the reference voltage and sends a second signal to controller 164 indicating that contact plate 190 is not touching both probes 43 and 45. When controller 164 receives this second signal, controller 164 activates an indicator means that informs the operator that rinse jug 142 is not operatively connected to rinse solution conduit 126. As embodied herein and schematically shown in FIG. 9 for example, an indicator 280 in the form of a light or LED "JUG REMOVED" message (FIG. 23) and/or buzzer can be mounted on control panel 168 and would suffice for a suitable embodiment of the indicator means. Thus, indicator 280 enables the operator to determine when rinse jug 142 has been removed from first housing 172, as when jug 142 is being refilled with rinse solution. Moreover, if rinse jug 142 is removed, controller 164 desirably is programmed so that it does not permit activation of rinse pump 150.

As embodied herein and shown schematically in FIGS. 1, 9, 15 and 16 for example, the apparatus of the present invention desirably includes at least one control panel 168. Desirably, as shown in FIG. 1 for example, control panel 168 is mounted to a foot-end guard rail 39. Moreover, a separate and identical control panel 168 can be mounted to each of the foot-end guard rails 39 of a bed so that the user can have access to a control panel from each side of the bed. Each control panel 168 desirably is provided with a plurality of indicators, which desirably are in the form of short messages appearing in a LED display. Each control panel 168 desirably is provided in a fluidproof configuration and is electrically connected to controller 164 via a multi-conductor cable 272 (FIG. 9).

In accordance with the present invention, a means is provided for detecting a predetermined level of liquid in the rinse solution container and providing a signal upon detecting same. Desirably, the rinse solution level detecting means is configured to detect when the level of rinse solution has become so low as to require filling the rinse solution container with additional rinse solution. As embodied herein, the rinse solution level detecting means can include a liquid sensor element that is mounted and disposed inside rinse jug 142 for detecting a predetermined level of rinse liquid inside rinse jug 142. As shown schematically in FIGS. 26, 27 and 29B for example, the liquid sensor element includes at least two threaded metallic screws 41, though more than two can be provided. At least one screw 41 secures an electrically conducting second contact plate 160 to the exterior of jug 142 and extends through the back endwall of jug 142 and inside jug 142. Each screw 41 in second contact plate 160 desirably is disposed at the same low level near the bottom of rinse jug 142 and above the open entrance end of siphon tube 146. As shown schematically in FIG. 27 for example, each liquid sensor screw 41 attached to second plate 160 forms part of an electrical detection circuit that includes the second contact plate 160 and a third probe 170 and produces an electrical response when the level of liquid within rinse jug 142 uncovers all of the rinse liquid sensor screws 41 attached to plate 160 and extending inside jug 142.

As schematically shown in FIG. 9 for example, the detection circuit for the level of liquid inside rinse jug is electrically connected to controller 164 via electrical cables 166. As schematically shown in FIG. 27 for example, the voltage at a comparator circuit element 171 is connected to a positive reference voltage, a capacitor 175, and third probe 170. Capacitor 175 is connected to ground. The Voltage at the comparator 171 stays below the positive reference voltage, typically a low voltage of positive 5 volts for example, so long as the level of rinse solution inside rinse jug 142 stays above at least one of the liquid sensor screws 41 attaching second contact plate 160 to jug 142 and extending inside jug 142. This is because the capacitor shorts to ground through third probe 170, the electrically conducting rinse solution inside rinse jug 142, and ground probe 43. When the voltage at comparator 171 falls below the reference voltage, comparator 171 sends a first signal to controller 164. When the liquid inside jug 142 falls below the level of the liquid sensor screws 41 attaching second contact plate 160 to jug 142 and extending inside jug 142, the voltage at comparator 171 is the reference voltage, and comparator 171 sends a second signal to controller 164. This is because the electrical path to ground through ground probe 43, the electrically conducting rinse solution inside jug 142, and third probe 170, is broken.

An alternative embodiment of the rinse solution level detecting means can be provided in a form which includes a float switch, which can be disposed with respect to rinse jug 142 so as to detect when jug 142 is almost empty. The float switch can be a magnetic reed switch (not shown) which is configured and disposed so that when it reaches a predetermined low level inside jug 142, it sends a low level signal to controller 164.

In addition, the rinse level detecting means can include a means for emitting a signal when the rinse liquid level sensor detects a predetermined level of fluid in the rinse solution container. As embodied herein and shown schematically in FIG. 9 for example, the signal emitting means can include an indicator 278 such as a buzzer or LED "RINSE JUG EMPTY" message (FIG. 23) which is mounted on control panel 168 and activated by controller 164 when controller 164 receives the second signal from comparator circuit element 171 indicative of a low supply of rinse solution inside rinse jug 142. Thus, indicator 278 alerts the operator when the amount of rinse fluid in the rinse solution jug 142 is almost completely depleted, and therefore additional rinse solution should be added to fill rinse jug 142. Moreover, if rinse jug 142 is sufficiently empty to cause indicator 278 to be activated, controller 164 is programmed so that it does not permit activation of rinse pump 150.

In yet further accordance with the present invention, a means can be provided for automatically coupling the rinse level detecting means to the controller when the rinse jug is received by the first housing. As embodied herein and schematically shown in FIG. 27 for example, the automatic coupling means desirably includes a pair of electrically conducting probes 43, 170. As shown schematically in FIG. 26 for example, probes 43, 170 are attached to the back endwall 233 of first housing 172. Moreover, when rinse jug 142 is received in first housing 172 and connector 180 is engaged, ground probe 43 is configured and disposed to make contact with first contact plate 190 while comparator probe 170 is configured and disposed to make contact with second contact plate 160 as well as being connected to controller 164 via cables 166. Probes 43, 170 thus cooperate with the slide receptacle 173 and dripless connector 180 to provide a means for coupling the rinse liquid level sensor in communication with a signal emitting means wherein the coupling means is automatically engageable when first housing 172 securely receives rinse solution container 142.

In still further accordance with the present invention, the removing means desirably includes a means for detecting and signaling when liquids, such as from a patient incontinence event for example, need to be removed from the patient environment, collected and contained for disposal. The liquid detecting and signaling means desirably communicates with at least one of the catching means and the removing means. As embodied herein and shown in FIG. 9 for example, the liquid detecting and signaling means can include a moisture sensor, which is indicated generally by the designating numeral 216. Desirably, moisture sensor 216 is disposed so that it can detect moisture in at least one of the catching means and the removing means and be able to emit a signal in response to detecting such moisture. As shown in FIG. 9 for example, moisture sensor 216 desirably is disposed for detecting moisture in cylindrical portion 63 of drain fitting 67 near the entrance to waste removal conduit 98 and accordingly can detect moisture before that moisture passes through waste removal conduit 98. Moisture sensor 216 is desirably disposed to detect moisture before that moisture reaches the collecting means (described below). As shown schematically in FIGS. 9 and 18 for example, moisture sensor 216 can include a pair of electrically conducting rings 218, 220. Each element 218, 220 can be formed of a one half inch wide stainless steel strip having both ends connected to one another to form a ring. Each ring 218, 220 has an internal diameter of about one-half inch.

As embodied herein and schematically shown in FIG. 18 for example, each ring 218, 220 is press-fitted into a groove defined in the inside surface of a portion of drain fitting 67 disposed near the free end 81 of the cylindrical portion 63 of drain fitting 67. A one quarter inch width spacer ring 219 is formed of insulating material with the same radius and thickness as each ring 218, 220 and is press-fitted into the same groove between ring 218 and ring 220. As indicated schematically in FIGS. 9 and 18, rings 218, 220 are electrically connected in an electrical circuit including lead wires 222 and controller 164. As schematically shown in FIG. 18 for example, the moisture detection mechanism formed by rings 218, 220 is very sensitive to moisture such that when moisture flows between the two rings 218, 220, current flows through lead wires 222 to an electrical circuit 221 which sends an electrical signal via a cable 223 to controller 164.

The liquid detecting and signaling means further includes an electrical signaling mechanism that emits a signal perceivable by the patient or attending personnel when moisture flowing within drain fitting 67 forms an electrical connection between rings 218, 220 and sends an electrical signal to controller 164. A suitable signaling mechanism can produce an audible and/or visible signal. As schematically illustrated in FIGS. 9 and 23 for example, a suitable signaling mechanism can include an electrical buzzer 281 and/or a light emitting diode (LED) "EVENT ALERT" message 282 which can be mounted on a control panel 168 of a patient support apparatus (FIG. 12A) or service cart 256 (FIGS. 15, 16), if desired. Desirably, the indicator mechanism is activated by controller 164 when controller 164 receives a moisture detection signal from rings 218, 220 or any other embodiment of the moisture detection mechanism. In addition, as shown in FIGS. 9 and 23 for example, a reset button 284 also can be provided as part of control panel 168 to enable the user to reset the moisture detection indicator mechanism. Furthermore, controller 164 desirably is programmed to reset indicators 281, 282 automatically whenever rinse pump 150 has been activated subsequent to activation of indicators 281, 282.

In accordance with the present invention, a means can be provided for controlling operation of the vacuum blower in response to moisture detection by the liquid detecting and signaling means. The vacuum blower control means desirably is connected to the vacuum blower and to the liquid detecting and signaling means. As embodied herein and schematically shown in FIG. 9 for example, the vacuum blower control means desirably includes a controller 164 electrically connected to the circuit including rings 218, 220 via cable 222 and electrically connected to vacuum blower 102 via cable 224. Controller 164 can be programmed so that when controller 164 receives a signal from the moisture detection mechanism indicating that moisture has entered the cylindrical portion 63 of drain fitting 67, controller 164 activates indicators 281, 282 on control panel 168. In addition, controller 164 activates vacuum blower 102 to high speed operation to provide suction that pulls the moisture out of basin 62, fitting 67, and conduit 98 and into holding reservoir 100. Controller 164 continues to operate vacuum blower 102 at high speed until moisture sensor 216 no longer detects any liquid. After a short time interval from the time when moisture sensor 216 fails to detect any liquid, controller 164 sends a signal to return vacuum blower 102 to low speed operation. Controller 164 is programmed to delay the deactivation of blower 102 from high speed to low speed for about 10 or 20 seconds so that waste can continue to be vacuumed from waste removal conduit 98, which is located downstream from basin 62 and drain fitting 67. The short delay time ensures that basin 62, drain fitting 67, and conduit 98 have been cleared of all liquid.

In yet further accordance with the present invention, a means is provided for collecting the waste removed from the waste catching means by the waste removing means. The waste collecting means desirably is disposed so as to be in communication with the waste removing means and facilitates containment of the waste materials at a location that is isolated from the patient and from persons attending the patient. Moreover, the waste collecting means desirably facilitates permanent disposal of the waste materials. As embodied herein and schematically shown in FIGS. 6, 9 and 28 for example, the collecting means desirably includes a waste collection container 192 in the form of a waste jug 192. A handle 144 is defined in a front endwall 145 of jug 192, which desirably is formed of liquid impermeable material such as high density polyethylene (HDPE), or polypropylene, or polycarbonate, or any similar rigid plastic material. Depending on the embodiment, the waste collection container can be configured to be removably securable to the patient support apparatus (FIG. 1) or to a transportable service cart 256 (FIGS. 12, 12A, 15 and 16 for examples) or can be formed as a permanent tank of the service cart. As shown in FIG. 29A for example, waste jug 192 desirably has a capacity of one gallon and can be emptied of waste via a pour opening 149 (shown in dashed line in phantom) which is defined at the free end of a circularly cylindrical annular member 151 (shown in phantom). The annular member desirably can be provided with an exterior surface having screw threads so that pour opening 149 is removably sealable by means of a screw-on threaded cap.

As embodied herein and shown schematically in FIG. 9 for example, the collecting means further includes a waste transfer pump 194 and waste transfer conduits 196. Waste transfer conduits 196 connect an outlet opening 198 defined in the bottom of holding reservoir 100 to waste jug 192 via waste transfer pump 194. Thus, waste collection jug 192 is disposed so as to be in communication with holding reservoir 100 via waste transfer conduits 196 and waste transfer pump 194. Waste transfer conduits 196 desirably can be formed of polyvinyl chloride (PVC) flexible tubing having a three-eighths inch interior diameter and a circular transverse cross-section. A suitable waste transfer pump is provided by a single speed peristaltic pump with a rated flow rate of 774 ml/min. at 1 psi through three-eighths inch internal diameter tubing when powered by a 24 volt direct current 1 ampere electric motor.

In still further accordance with the present invention, a means can be provided for automatically controlling operation of the waste transfer pump so as to transfer waste from the removing means to the waste collection container whenever a predetermined minimum level of waste has accumulated within the holding reservoir. As embodied herein, the means for automatically controlling operation of the waste collection means so as to transfer waste from the removing means to the collection means, desirably includes a means for detecting when the removing means becomes filled to a predetermined proportion of its capacity.

As embodied herein and schematically shown in FIG. 9 for example, a means for detecting when the removing means becomes filled to a predetermined proportion of its capacity, desirably includes a low level liquid sensor. The low level liquid sensor desirably includes a low reservoir probe 131 which can be provided in the form of a stainless steel screw disposed near the bottom of holding reservoir 100 and extending into the interior of reservoir 100 from a wall thereof. Low reservoir probe 131 need not be a spring loaded probe, as is used for the rinse solution level detecting means for example. However, the low level liquid sensor for holding reservoir 100 desirably includes an electronic arrangement similar to the means for detecting the level of rinse liquid inside rinse jug 142, described above, and is electrically connected to controller 164. Thus, a second stainless screw (not shown) would be provided at the same height as screw 131 near the bottom of holding reservoir 100 and extending into the interior of reservoir 100 from a wall thereof. This second screw would be connected electrically to ground, and screw 131 would be connected to the same electronic configuration as probe 170 shown in FIG. 27. When probe 131 and the second screw are covered by liquid, an electrical signal is transmitted to controller 164 and indicates that a minimum level of liquid is contained in holding reservoir 100.

As embodied herein, the means for detecting when the removing means becomes filled to a predetermined proportion of its capacity, desirably further includes a high level liquid sensor which is electrically connected to controller 164. As schematically shown in FIG. 9 for example, the high level liquid sensor desirably includes a high reservoir probe 107, which desirably is provided in the form of a stainless steel screw 107 disposed near the top of holding reservoir 100 and extends into the interior of reservoir 100 from a wall thereof. The high level liquid sensor for holding reservoir 100 desirably includes an electronic arrangement similar to the means for detecting the level of rinse liquid inside rinse jug 142, described above, and is electrically connected to controller 164. Thus, a second stainless screw (not shown) would be provided at the same height as screw 131 near the bottom of holding reservoir 100 and extending into the interior of reservoir 100 from a wall thereof. This second screw would be connected electrically to ground, and high level screw 107 would be connected to the same electronic configuration as probe 170 shown in FIG. 27. When screw 107 and the second screw are covered by liquid, an electrical signal is transmitted to controller 164 and indicates that a high level of liquid is contained in holding reservoir 100. When the controller receives the signal from high reservoir sensor 107, the controller desirably performs several preprogrammed functions. For example, the controller can activate a warning indicator 128 on control panel 168 (FIG. 23) to alert the operator that the liquid inside holding reservoir 100 is at the predetermined level which indicates that the holding reservoir is nearing its full capacity. Detection of liquid at such a high level inside holding reservoir 100 could indicate the occurrence of a system malfunction that should be investigated by service personnel. Thus, warning indicator 128 desirably is provided in the form of an LED message such as "SERVICE REQUIRED". In addition, upon receipt of the high level signal from high level liquid sensor 107, controller 164 disables operation of vacuum blower 102, waste transfer pump 194, and rinse pump 150. When controller 164 disables vacuum blower 102, no suction from waste removal conduit 98 and/or a vacuum wand 104 can introduce additional wastes into the holding reservoir 100 which is nearing its capacity. Moreover, while controller 164 is preventing operation of waste transfer pump 194, no damage to pump 194 can occur before a service technician can correct the malfunction which permitted such a high level of waste to accumulate within holding reservoir 100.

In accordance with the present invention, a means can be provided for receiving the waste collection container. As embodied herein and shown schematically in FIG. 28 for example, the waste collection container receiving means includes a second housing 206, which desirably is configured almost identically as first housing 172. Accordingly, the description of second housing 206 will concentrate on the differences which exist between second housing 206 and first housing 172. Depending upon the particular embodiment of the present invention, second housing 206 can be provided as part of a bed 30, or as part of a service cart 256, or as part of an emergency treatment table, or the like. As schematically shown in FIG. 28 for example, second housing 206 can be carried by the bed frame beneath the footboard and fixed to the upper frame 36. As shown in FIG. 28 for example, second housing 206 includes at least one slide receptacle 173 which slidably and nonrotatably receives a mating groove member 174 (FIG. 6) defined as part of the exterior of waste jug 192 to ensure proper alignment of waste jug 192 with respect to second housing 206.

As shown schematically in FIGS. 12 and 12A or 15 and 16 for example, the second housing can be formed as part of the upright frame 258 (FIGS. 15 and 16) or low profile portion 264 of a mobile service cart 256. In some cart embodiments, the waste collection container 192 is provided as a permanent part of the service cart. As shown schematically in FIG. 16 for example, a drain hose 193 is provided for emptying waste material that has accumulated in waste collection container 192. Drain hose 193 is held by a bracket 191 and is connected to waste collection container 192 via a quarter turn valve 197, which governs fluid transfer from container 192 into hose 193.

In further accordance with the present invention, a means can be provided for connecting the waste collection container in communication with the holding reservoir. Desirably, the connecting means automatically engages the collection container into communication with the holding reservoir when the second housing receives the waste collection container. Moreover, the connecting means is configured to prevent waste from escaping when the collection container is disengaged from the second housing. As embodied herein and shown in FIG. 14 for example, the waste jug connecting means desirably includes the same type of dripless connector 180 which forms the rinse jug connecting means and is connected and disposed in waste jug 192 in a similar fashion as connector 180 is connected and disposed in rinse jug 142 shown in FIG. 26 for example. Thus, the waste jug connecting means desirably includes a dripless connector 180, which forms the inlet/- outlet valve 148 and includes both a male member 182 and a female member 184. In addition, the receiving means (second housing 206) for the waste collection container 192 also includes substantially the same type of means for positively locking the waste jug into second housing 206 as the positive locking means (both embodiments) for locking the rinse jug into first housing 172 and described above.

In further accordance with the present invention, a means can be provided for detecting when the waste collection container is securably received by the second housing and providing a signal upon detecting such securable receipt. Desirably, the securably received detecting means is connected to provide its signal to the controller, which can indicate receipt of such signal by actuating an indicator means of a control panel. As embodied herein and shown schematically in FIG. 9 for example, the securably received detecting means for waste jug 192 can include the same type of arrangement described above (see FIG. 27) for detecting when the rinse jug 142 is securably received by the first housing 172. A pair of electrical probes 43, 45 is similarly disposed with respect to a first contact plate 190 mounted on waste jug 192. As embodied herein and schematically shown in FIG. 9 for example, first contact plate 190 of waste jug 192 can provide an electrical detection signal to controller 164 via a cable 213. Controller 164 then sends a signal via cable 272 to activate a suitable embodiment of the indicator means such as an LED "JUG REMOVED" message 276 shown in FIG. 23 for example and/or buzzer 276 mounted on control panel 168. Thus, indicator 276 informs the operator when waste jug 192 has been removed from second housing 206, as when jug 192 is being emptied.

In accordance with the present invention, a means can be provided for detecting a predetermined high level of waste liquid in the waste collection container and providing a signal upon detecting same. Desirably, the waste level detecting means is configured to detect when the level of liquid waste has become so high as to require emptying the waste collection container of its contents. As embodied herein and shown schematically in FIG. 9 for example, the waste level detecting means can include the same type of arrangement described above (FIG. 27) for detecting when the rinse jug 142 has only a low level of rinse solution and needs to be refilled. However, as schematically shown in FIGS. 9 and 29A for example, in the high level liquid detecting means for waste jug 192, the second contact plate 160 and its liquid level sensor screws 41 are disposed at a high level on waste jug 192 near the top of waste jug 192. Moreover, each liquid sensor screw 160 in second contact plate 160 forms part of an electrical detection circuit that includes the second contact plate 160, a pair of probes 43, 170, and first contact plate 190 and produces an electrical response when the level of liquid within waste jug 192 covers at least one waste liquid sensor screw 41 attaching second plate 160 to jug 192. As schematically shown in FIG. 9 for example, this detection circuit 170 is electrically connected to controller 164 via electrical cables 210 and provides an electrical signal to controller 164 upon detection of the predetermined high level of liquid within waste jug 192.

In addition, the level detecting means can include a means for emitting a signal when the waste liquid level sensor detects a predetermined high level of fluid in waste jug 192. As embodied herein, the signal emitting means can include a buzzer and/or LED which is activated by controller 164 on control panel 168 when controller 164 receives a high liquid level detection signal from waste liquid sensor screws 41 disposed into waste jug 192. In addition, controller 164 desirably is programmed so that operation of waste transfer pump 194 is not permitted by controller 164 unless controller 164 receives a signal indicating that waste jug 192 has been installed securely in second housing 206 with sufficient capacity to receive additional waste material via waste transfer conduits 196.

In yet further accordance with the present invention, a means can be provided for automatically coupling the high liquid level detecting means located in the waste jug to the controller when the waste jug is received by the second housing. As embodied herein, the automatic coupling means desirably includes substantially the same arrangement as described above for the low liquid level detecting means of the rinse solution jug and thus includes probes 43, 170. However, probe 170 for the waste jug is disposed at the high level of the waste jug in order to be in a position to contact the second contact plate 160 bearing its respective screws 41. Probes 43, 170 thus are provided as a means for coupling a high liquid level sensor in communication with a signal emitting means wherein the coupling means is automatically engageable when the second housing receives the waste collection container securably therein.

Each of the jugs 142, 192 disposed within their respective housings 172, 206, whether beneath the bed in some embodiments (FIGS. 12 and 12A for example) attached to the bed frame in other embodiments (FIGS. 6 and 28 for example) or carried by a service cart 256 in still other embodiments (FIGS. 12, 12A, 15 and 16 for example), would be provided with means that would make it impossible to interchange the waste collection jug 192 with the rinse solution jug 142. As embodied herein and schematically shown in FIGS. 6, 28, 29A and 29B for example, rinse solution jug 142 has a narrower width, as evidenced by its narrower front and rear endwalls 145, than waste jug 192. Similarly, as shown in FIG. 28 for example, first housing 172 has a norrower slide receptacle 173 than the slide receptacle 173 defined by second housing 206. Accordingly, it is impossible for waste jug 192 to be received by first housing 172 and equally impossible for rinse jug 142 to be received by second housing 206. Alternatively, each of the jugs 142, 192 could be provided with a different configuration connector 180 and/or have the same configuration connector 180 located in a relatively different position so that it would be impossible to interchange the waste collection jug with the rinse solution jug.

In accordance with the present invention, a means can be provided for keeping track of the amount of liquids that is collected in the waste jug. For example, these liquids could be the kind expelled by the patient through incontinence events. As embodied herein and shown schematically in FIG. 29A for example, the expelled liquid accounting means can include waste collection jugs 192 formed of translucent material and provided with volume graduations 214 in 50 ml increments, which indicate the liquid volume contained inside the jug. The same sort of graduations 214 (FIG. 29B) can be provided for the rinse solution jug, which can be formed of material that is almost transparent. In this way, each jug is provided with a visually observable level indicator for the liquid in the jug.

In accordance with the present invention, a means can be provided for controlling operation of the waste transfer pump in response to the detection of liquid by the low level liquid sensor disposed in the waste removing means. The waste transfer pump control means desirably is connected to communicate with each of the waste transfer pump, the low level liquid sensor in the waste removing means, and the high level liquid sensor in the waste jug. As embodied herein and schematically shown in FIG. 9 for example, a waste transfer pump control means desirably includes controller 164 electrically connected to each of the waste transfer pump 194, low level liquid sensor 131 inside holding reservoir 100, and the high liquid level screws 41 of the waste jug 192. Controller 164 can be programmed so that when it receives a signal from the low level liquid sensor 131 indicating that moisture has reached a high enough level inside reservoir 100 to cover sensor 131, controller 164 checks for signals indicating that waste jug 192 is both securely connected to second housing 206 and has sufficient empty capacity to be able to accept additional waste material. If and only if the latter two conditions are detected by controller 164, controller 164 activates waste transfer pump 194 to pump waste from holding reservoir 100 to waste collection jug 192. Controller 164 continues to operate pump 194 until controller 164 receives a signal indicating that waste jug 192 is nearing capacity or that the level of waste inside holding reservoir 100 is beneath sensor 131 and thus near outlet opening 198 of reservoir 100. However, instead of immediately turning off waste transfer pump 194, controller 164 delays about fifteen seconds before signaling waste transfer pump 194 to stop. This prevents pump 194 from cycling on and off in rapid succession. Controller 164 also is programmed so that when controller 164 receives a signal from the waste jug's high liquid level sensor 160 indicating that waste jug 192 is nearing capacity, controller 164 deactivates waste transfer pump 194 and activates an indicator 274 on control panel 168 (FIG. 9) to alert the operator to empty waste jug 192. As shown in FIG. 23 for example, indicator 274 can be provided in the form of an LED message such as "HOLDING JUG FULL."

In an alternative embodiment of the present invention, a means can be provided for controlling operation of the waste transfer pump in response to the detection of liquid by the liquid detecting and signaling means. In this alternative embodiment, the waste transfer pump control means desirably is connected to communicate with each of the waste transfer pump, the liquid detecting and signaling means, and the high level liquid sensor in the waste jug. As embodied herein and schematically shown in FIG. 9 for example, a waste transfer pump control means desirably includes a controller 164 electrically connected to each of the waste transfer pump 194, the moisture detecting and signaling means, and the high liquid level screws 41 of the waste jug 192. Controller 164 can be programmed so that when it receives a signal from the liquid detection circuit indicating that moisture has entered the lower region of drain fitting 67, controller 164 checks for signals indicating that waste jug 192 is both securely connected to second housing 206 and has sufficient empty capacity to be able to accept additional waste material. If and only if the latter two conditions are detected by controller 164, controller 164 activates waste transfer pump 194 to pump waste from holding reservoir 100 to waste collection container 192. Controller 164 continues to operate pump 194 until controller 164 receives a signal indicating that waste jug 192 is nearing capacity or that the level of waste inside holding reservoir 100 is near outlet opening 198 of reservoir 100. Controller 164 also is programmed so that when controller 164 receives a signal from the waste jug's high liquid level sensor 160 indicating that waste jug 192 is nearing capacity, controller 164 deactivates waste transfer pump 194 and activates indicator 274 on control panel 168 (FIGS. 9 and 23) to alert the operator to empty waste jug 192.

In further accordance with the present invention, a means can be provided for adapting the waste managing means to be carried by the frame of a patient support apparatus. The adapting means desirably is supported by the frame of the patient support apparatus and is configured for receiving the second portion supporting means and for being carried by the frame. As embodied herein and shown in FIGS. 1, 2 and 2A for a low air loss bed for example, the adapting means desirably includes an adaptor shell 228. The embodiment of adaptor shell 228 shown in FIG. 1 desirably defines a bottom surface 230 configured substantially flat for being carried by a frame for a low air loss bed. However, a different frame could form part of a conventional hospital bed with an articulatable frame, a wheelchair, a hospital emergency room treatment table, or the like, and bottom surface 230 of adaptor shell 228 would be configured to adapt to such different frame.

Adaptor shell 228 further generally defines at a central location, a receiving opening 232. Receiving opening 232 desirably is defined with a configuration for securingly and supportingly receiving the waste managing means such that the supporting means of the waste managing means is disposed substantially coplanar with the patient support surface of the patient support apparatus. In a low air loss bed 30 as illustrated in FIG. 1 for example, this patient support surface is defined by the upper surfaces 46 of sacks 44. Accordingly, as shown in FIGS. 2 and 2A for example, base portion 54 of support bladder 48 is received by receiving opening 232 of adaptor shell 228, which securely receives this support member.

As shown in FIGS. 1 and 2 for example, in an embodiment of the waste managing means designed to be used in a low air loss bed embodiment, adaptor shell 228 desirably is formed by a plurality of individual inflatable cushions 234 having a generally U-shaped external configuration defining receiving opening 232. Each oppositely disposed leg portion 236 of each cushion 234 stands the same ten inches tall as the normal height of a conventional sack 44 of a low air loss bed. However, the intermediate base portion of each U-shaped cushion 234 stands only about five to five and one half inches inches high as opposed to being 10 inches high as a normal height sack 44 of a low air loss bed. The interior surfaces of the legs 236 of the U-shaped cushions 234 cooperate with the base portion of the U-shaped cushions to define receiving opening 232. As schematically shown in FIGS. 1 and 2 for example, adaptor shell 228 also can include a conventional height air sack 44 disposed at each opposite end of the plurality of side-by-side cushions 234 and further defining receiving opening 232.

As shown in FIG. 2 for example, an elongated slot 237 can be defined in the intermediate portion of a centrally located cushion 235, which is about three times wider than adaptor shell cushions 234 located on opposite sides of central cushion 235 of adaptor shell 228. Slot 237 provides access for drain fitting 67 and/or waste removal conduit 98 to provide communication between holding reservoir 100 and drain opening 66 defined in floor 64 of basin member 62. In addition, the external surfaces of the legs 236 of the U-shaped configuration of each cushion 234 or 235 define opposed externally facing peripheral walls 238.

Desirably, cushions 234, 235 are entirely formed of HY TEX TM fabric, which is a urethane film laminated to nylon twill material that can be heat sealed to form an air tight enclosure, and are inflatable with pressurized air. Alternatively, a fabric coated with polytetrafluoroethylene (TEFLON) can be used to form cushions 234 if such material is mechanically sealed, as by sewing for example. Each cushion 234 desirably is provided with inlet fittings (not shown) so that it can be inflated with air using the air supply system of a low air loss bed or an independent air supply system. Thus, at least a first section of adaptor shell 228 can be configured to be inflatable with a gas. Because the means for supplying pressurized air to cushions 234 and support bladder 48 can be easily adapted to the air supply system that exists to supply pressurized air to the support sacks 44 of a low air loss bed, the waste managing means of the present invention is easily retrofitted to existing low air loss beds.

Additionally, an alternative embodiment of adaptor shell 228 can be formed of a flexible and resilient foam material for example, or of another flexible material capable of providing the proper supportive receiving configuration for the waste managing means.

As embodied herein and schematically shown in FIGS. 1 and 1A for example, a means for carrying the waste managing means can include a tray 242. Tray 242 has a pair of opposed sidewalls 244 which extend vertically from a tray bottom 246. The free edge of each sidewall is configured to form a flange 248 disposed perpendicularly to sidewall 244 and parallel to tray bottom 246. The height of each sidewall 244 is desirably configured to be at least as high as the height of frame rails 38 of lower frame 34, and can be higher as shown in FIG. 1 for example. The width of each flange 248 desirably is configured to the same dimensions as the width of frame rails 38 of lower frame 34. Flanges 248 rest atop frame rails 38 of lower frame 34, which carries tray 242. Tray 242 desirably can carry four 17 Amp-Hr batteries 252 and is located at about the midpoint of lower frame 34.

As embodied herein and schematically shown in FIGS. 1, 6, 10 and 28 for example, the means for carrying the waste managing means can further include a foot-of-the-bed-mounted container 254. Foot-mounted container 254 desirably includes an enclosure and a base plate mounted on slides which enable the base plate to slide horizontally in and out from within the enclosure. Holding reservoir 100, waste transfer pump 194, and vacuum blower 102 are all desirably mounted on and carried atop the base plate of foot-mounted container 254.

Figure 12:
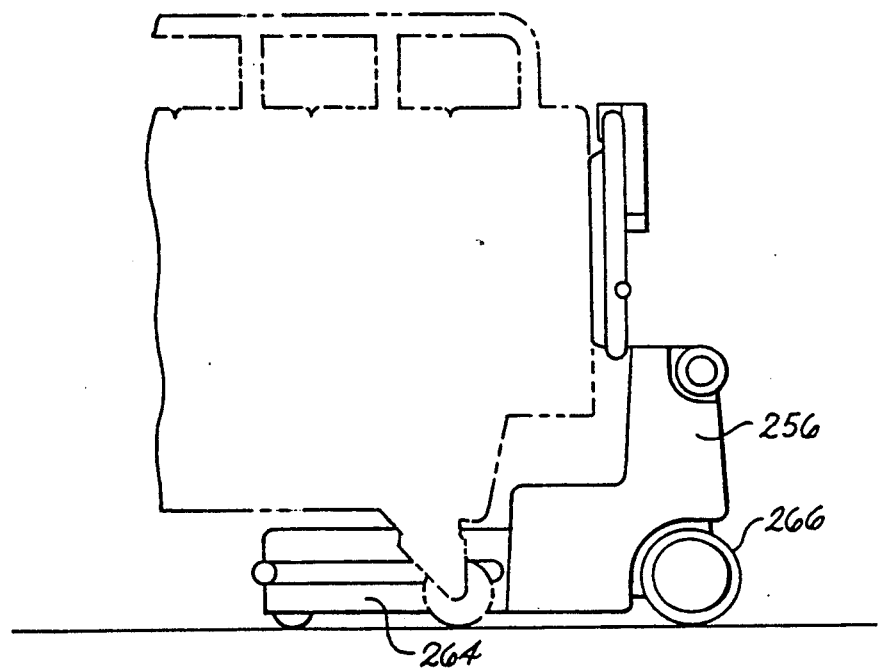
FIG. 12 schematically illustrates components of an alternative preferred embodiment of the present invention from a side plan view with portions indicated in phantom by the dashed lines.
Figure 12A:
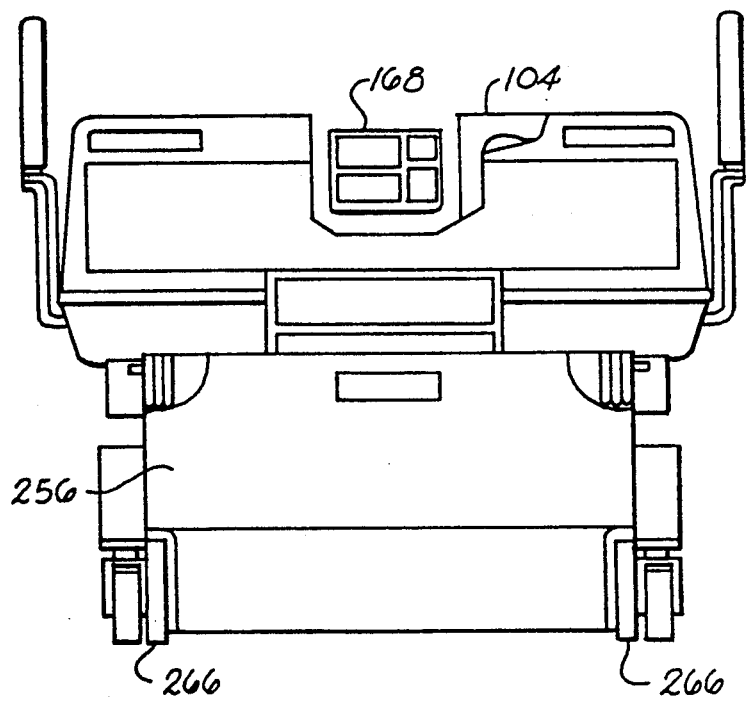
FIG. 12A schematically illustrates components of the alternative preferred embodiment of the present invention shown in FIG. 12, but from a front plan view with portions indicated in phantom by the dashed lines and with portions partially cut away.
Figures 15, 16:
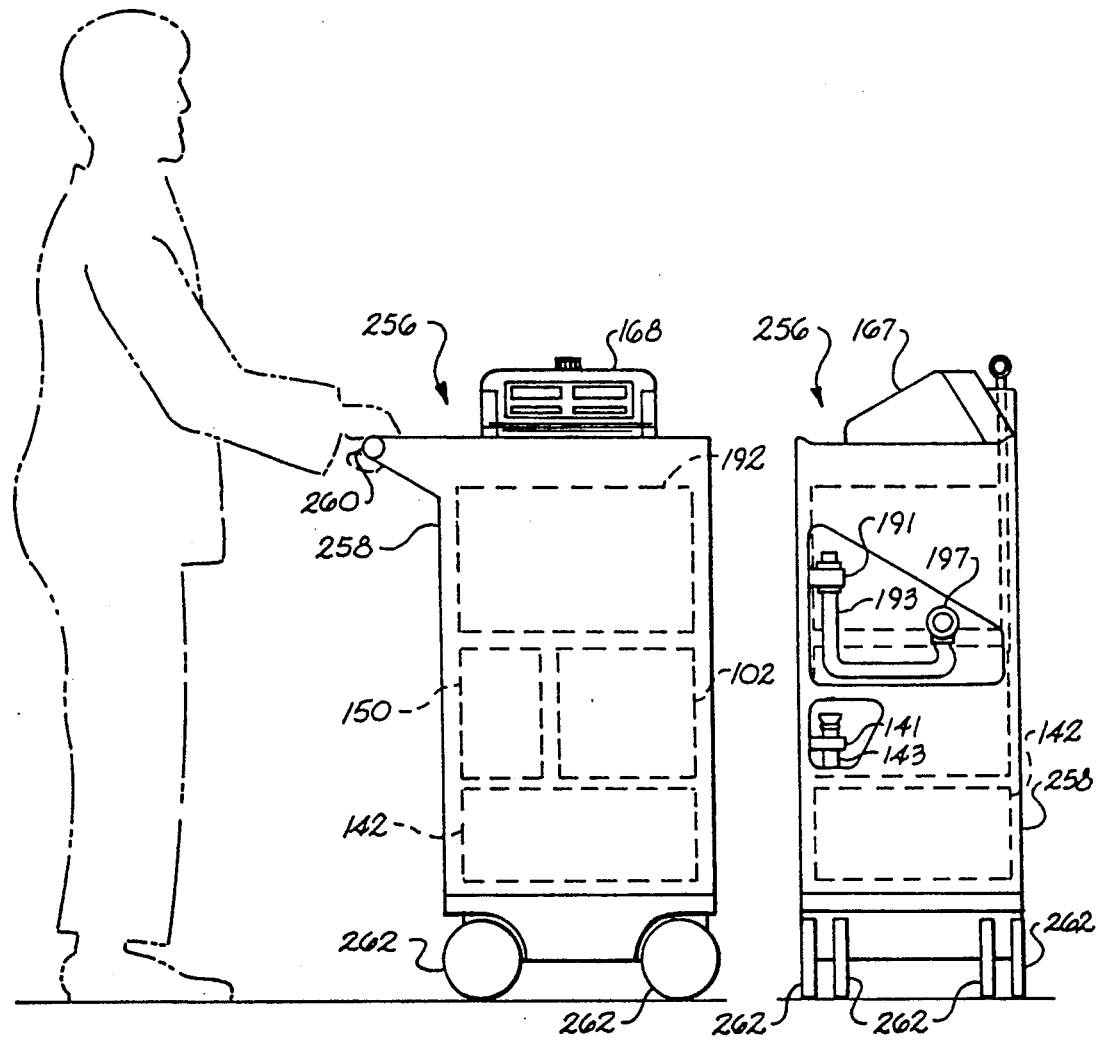
FIG. 16 schematically illustrates components of the alternative preferred embodiment of the present invention shown in FIG. 15, but from a front plan view with portions indicated in phantom by the dashed lines and with portions partially cut away.

Alternatively, and as shown in FIGS. 12, 12A, 15, and 16 for example, the means for carrying the waste managing means can include a mobile service cart 256. As schematically shown in FIGS. 15 and 16 for example, an upright mobile service cart 256 can include an upright frame 258, a handle 260 and wheels 262. As schematically shown in FIGS. 12 and 12A for example, an undercarriage service cart 256 has a low profile portion 264 that can be slid beneath one end of the frame of a bed and is carried by larger support wheels 266 disposed at one end and smaller wheels 268 disposed at the low profile end.

In still further accordance with the present invention, a means can be provided for turning the patient to facilitate cleansing of the patient after an incontinence event for example. Desirably, the apparatus of the present invention is capable of turning the patient automatically about 20 degrees from the horizontal plane in order to enable a single member of the hospital staff to turn the patient the rest of the way to the patient's side to facilitate cleansing of the patient with vacuum wand 104. In addition, the turning means desirably is carried by the frame of the patient support apparatus. As embodied herein and shown schematically in FIGS. 2 and 2A for example, the turning means desirably includes filter sheet 80 described above and used to perform the function of a drawing sheet. However, as embodied herein and shown in FIGS. 8 and 13 for example, the turning means also desirably includes a plurality of specially configured turning sacks 270 which are provided with pressurized air in one or more configurations under the control of a controller 164. Turning sacks 270 assist the turning operation by automatically, and without the effort of hospital staff, turning the patient about 20 degrees toward one side or the other. This automatic partial turning of the patient enables a single nurse or other member of the hospital staff to completely turn the patient entirely to the patient's side by pulling on filter sheet 80.

Figure 8:
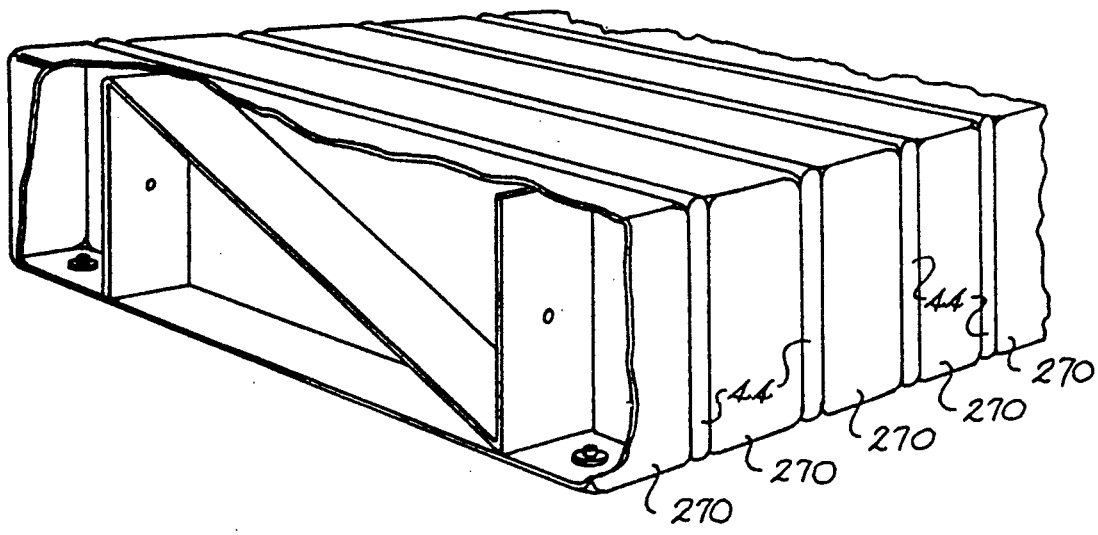
FIG. 8 schematically illustrates an elevated perspective view of components of an embodiment of the present invention.

As schematically shown in FIG. 8 for example, the operative turning sacks 270 can be configured as the so-called RESTCUE® type sacks disclosed in U.S. Pat. No. 4,949,414 to Thomas et al, the disclosure of which patent is hereby incorporated into this patent application by this reference. In addition, a plurality of turning sacks 270 can be alternated with a plurality of conventional low air loss bed support sacks 44 such as the so-called FLEXICAIR® sacks disclosed in U.S. Pat. Nos. 4,745,647 to Goodwin; 4,768,249 to Goodwin: and 4,949,413 to Goodwin. the disclosures of which patents are hereby incorporated into this patent application by this reference.

Figure 13:
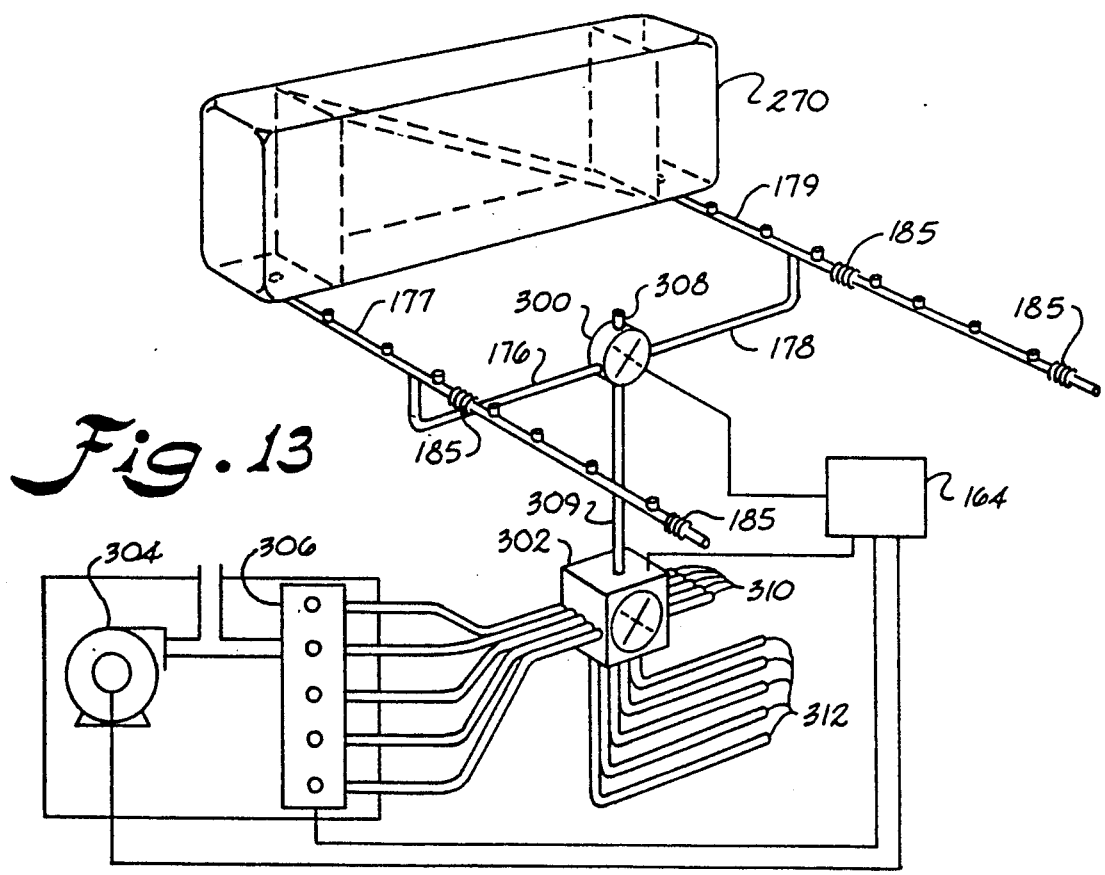
FIG. 13 schematically illustrates components of a preferred embodiment of the present invention from an elevated perspective view.

As embodied herein and shown schematically in FIG. 13 for example, the means for controlling the air supplied to the turning means includes a pair of air flow diverter valves 300, 302 through which low pressure air is selectively supplied to turning sacks 270 via air flow conduits 176, 177, 178, 179. Conduits 177, 179 are provided with an accordian section 185 at each location where conduits 177, 179 pass across an articulating section of the frame carrying conduits 177, 179. A first diverter valve 300 is a 4-port 2-way valve, while a second diverter valve is a 16-port 2-way valve. Both diverter valves 300, 302 are motor operated under the control of controller 164 and can be supplied with low pressure air from a blower 304 and a multi-valve manifold 306, which also are controlled by controller 164. First diverter valve 300 can be configured (solid diagonal line in FIG. 13) to supply low pressure air to the right sides of turning sacks 270 while connecting the left sides of sacks 270 to atmosphere via a vent port 308. Alternatively, first diverter valve 300 can be configured (dashed diagonal line in FIG. 13) to supply low pressure air to the left sides of turning sacks 270 while connecting the right sides of sacks 270 to atmosphere via vent port 308. Second diverter valve 302 can be configured (solid diagonal line in FIG. 13) to supply low pressure air to the turning sacks 270 through turning sack port 309 and first diverter valve 300, while simultaneously connecting the support sacks 44, which as shown in FIG. 8 are disposed alternately between each pair of turning sacks 270, to atmosphere via five vent ports 310, one vent port 310 for each zone group of support sacks in bed 30, and five support sack ports 312. The air flow conduits used to supply air to the support sacks 44 are different than conduits 176, 177, 178, 179 shown in FIG. 13 and are not shown in FIG. 13. In a second alternative configuration (dashed diagonal line in FIG. 13) of second diverter valve 302, low pressure air is supplied from blower 304 via five support sack ports 312 to the support sacks 44, which as shown in FIG. 8 are disposed alternately between each pair of turning sacks 270, while connecting the turning sacks 270 through first diverter valve 300 and vent ports 310 to atmosphere.

Controller 164 desirably is preprogrammed to use both diverter valves 300, 302 to control the air supplied to the two groups (turning 270 and support 44) of air sacks forming the patient turning means. During the turning operation, one of the two groups (turning sacks 270 for example) of air sacks is either completely filled or being filled, while the other of the two groups (support sacks 44 for example) of air sacks is either completely empty or being deflated. Controller 164 desirably is preprogrammed so that inflation of the fully deflated group of air sacks begins to occur at the same time as the onset of deflation of the fully inflated group of air sacks begins to occur.

Furthermore, each control panel 168 desirably contains controls and indicators for turning the patient using the turning sacks 270. As embodied herein and shown schematically in FIGS. 9 and 23 for example, a control button 286 causes controller 164 to implement turning of the patient to the right and to activate an indicator 288, which indicates that the patient has been turned to the right side of the support surface. Similarly, a control button 290 causes controller 164 to implement turning of the patient to the left and to activate an indicator 292, which indicates that the patient has been turned to the left side of the support surface. In addition, a control button 294 causes controller 164 to implement turning of the patient back to the center from either the left or the right side of the support surface and to activate an indicator 296, which indicates that the patient has been turned back to the center portion of the support surface.

When the operator presses the left turn or right turn button, controller 164 activates a diverter valve motor to configure the second diverter valve 302 to provide air from the air supply means, such as blower 304 and multi-valve manifold 306, to the turning device such as turning bags 270 (FIGS. 8 and 13). Controller 164 also sends a control signal to activate the proper turning indicator 288, 292, 296 as well as configuring first diverter valve 300 to divert air into the proper side, left or right, of turning sacks 270.

The turning device remains in the turned condition until the operator presses center button 294. When center button 294 is pressed, controller 164 sends a signal to reconfigure (as shown schematically by the dashed diagonal line in FIG. 13) second diverter valve 302 to allow air from the heretofore inflated side of turning sacks 270, to exhaust through vent ports 310. At the same time, controller 164 sends a signal to the air supply source, such as blower 304, to inflate support sacks 44 to a maximum inflation condition for a period of one minute in order to assist bringing the patient back to the center position. After the one minute maximum inflation, controller 164 signals blower 304 to operate in a manner that supplies the normal air pressure to support sacks 44. In addition, controller 164 activates center indicator 296 on control panel 168 to indicate that the system is returning the patient to the center position. Controller 164 returns center indicator 296 to the off condition as soon as the air supply source returns sacks 44 to a normal pressurized condition.

At articulation angles of 30 degrees and higher, it becomes undesirable to permit the patient turning means to be activated. Accordingly, controller 164 is preprogrammed to prohibit initiation of the turning operation if the angle of the head section of the bed is elevated above 30° from the horizontal. Moreover, each control panel 168 desirably includes a warning indicator actuatable by controller 164 to alert the operator when the patient support surface has been articulated to at least an angle of 30 degrees above the horizontal.

In accordance with the present invention, means can be provided to prevent operation of the patient turning means unless the side rail is in the raised position in the patient support system. As embodied herein and schematically shown in dashed line in FIG. 1 for example, the means for preventing operation of the turning means while the side rail is in the lowered position desirably includes an appropriately disposed and wired side rail interlock microswitch 169 which sends a signal to controller 164 when side rail 167 is locked in the upright position (schematically shown in FIG. 1 for example). Controller 164 is preprogrammed to prevent activation of the patient turning means unless the signal received from each microswitch 169 indicates that the side rails 167 are locked in the upright position. In addition, controller 164 activates a warning indicator 165 (FIG. 23) on control panels 168 to alert the operator when the side rail is oriented in the lowered position and the operator is attempting to activate the patient turning means. As shown in FIG. 23 for example, indicator 165 can be provided in the form of an LED "SIDE RAIL DOWN" message 165.

In accordance with the present invention, a means can be provided for counting the number of incontinence events that occur during a given period of time. As embodied herein and shown schematically in FIG. 9 for example, the counting means can include controller 164 suitably programmed to keep account of the number of signals received from the moisture detecting and signaling means during a given interval of time.

As embodied herein, controller 164 desirably provides the capability for automatically controlling various electrically actuatable devices such as rinse pump 150, waste transfer pump 194, vacuum blower 102, and the various valves 300, 302, 306 provided for the inflatable sacks 44, 270, cushions 234, and the support bladder 48. Controller 164 also desirably provides interfaces between various components of the system and the control panel's visual indicators that allow the operator to monitor the status of the system. In this regard, controller 164 desirably automatically monitors existing functions of the patient support apparatus, monitors the occurrence of events which create waste materials that need to be removed from the patient environment and contained for disposal, and monitors liquid volume levels in the rinse jug 142, holding reservoir 100, and waste collection jug 192.

Whenever a CPR procedure must be performed, controller 164 sends the appropriate signals to stop whatever operation the waste management apparatus was performing. For example, controller 164 removes power from waste transfer pump 194, vacuum blower 102, and rinse pump 150. In addition, controller 164 also opens any valves necessary to deflate turning sacks 270, support bladder 48, and adaptor shell 228. Furthermore, notwithstanding whether a CPR procedure is being performed, if the waste management apparatus of the present invention is provided in conjunction with an articulatable low air loss bed, controller 164 desirably is programmed to turn off vacuum blower 102 and rinse pump 150 during both articulation and raising or lowering of the bed, in order to prevent power circuit overloads.

What is claimed is:

1. An apparatus for managing waste arising from at least one of the care, maintenance, and treatment of a patient, the apparatus comprising:
   a) means for supporting at least a portion of the patient's body;
   b) means for catching waste, said waste catching means being carried by said supporting means;
   c) a vacuum blower disposed for sucking the wastes from said catching means;
   d) a holding reservoir disposed in communication with said catching means and said vacuum blower to receive the waste sucked from said catching means by said vacuum blower, wherein:
   e) said supporting means includes:
      i) a support member configured to contain pressurized air,
      ii) said support member defining a plurality of discrete support fingers disposed adjacent to each other and separated from each other, and
      iii) each said support finger having a free end defining a patient support surface, said patient support surfaces being disposed to support the weight of the second portion of the patient's body, wherein said supporting means further includes:
      iv) an air permeable foam member disposed inside said support member and beneath said plurality of discrete support fingers.

2. An apparatus as in claim 1, wherein:
   d) said support member further defines a drain opening and a floor configured to slope toward said drain opening; and
   e) said foam member is configured to conform to and rest against said floor of said support member and is further configured with an opening in registry with said drain opening of said support member.

3. An apparatus for managing waste arising from at least one of the care, maintenance, and treatment of a patient, the apparatus comprising:
   a) means for supporting at least a portion of the patient's body;
   b) means for catching waste, said waste catching means being carried by said supporting means, said catching means including:
      i) a liquid impermeable basin member,
      ii) said basin member being configured to conform to and receive said supporting means,
      iii) said basin member being further configured with a floor disposed beneath the upward-most level of said supporting means when said basin member is fitted over said supporting means and receives said supporting means,
      iv) said basin member being further configured with at least one drain opening defined through said floor, and
      v) said floor being configured so as to slope toward said at least one drain opening, and
      vi) a liquid permeable filter sheet disposed to be carried atop said basin member, wherein:
      vii) said basin member defines a plurality of grid configurations,
      viii) each said grid configuration being configured and disposed to support said filter sheet, and
      ix) each said grid configuration defining a plurality of slightly raised portions and a plurality of recessed channel portions separated from one another by said raised portions;
   c) a vacuum blower disposed for sucking the wastes from said catching means; and
   d) a holding reservoir disposed in communication with said catching means and said vacuum blower to receive the waste sucked from said catching means by said vacuum blower.

4. An apparatus as in claim 3, wherein:
   x) said channel portions of said grid configurations being wider than the liquid openings which render said filter sheet liquid permeable.

5. An apparatus as in claim 3, wherein:
   x) said filter sheet and said grid configurations are formed of materials such that the coefficient of friction between them is practically frictionless.

6. An apparatus for managing waste arising from at least one of the care, maintenance, and treatment of a patient, the apparatus comprising:
   a) means for supporting at least a portion of the patient's body, said supporting means including a flexible member inflatable with pressurized air, said flexible member including a plurality of flexible surfaces forming in combination a discontinuous surface for receiving said portion of the patient's body;
   b) means for catching waste, said waste catching means being carried by said supporting means;
   c) a vacuum blower disposed for sucking the wastes from said catching means;
   d) a holding reservoir disposed in communication with said catching means and said vacuum blower to receive the waste sucked from said catching means by said vacuum blower;
   e) means for collecting the waste received by said holding reservoir, said collecting means being removably securable in communication with said holding reservoir, wherein said collecting means includes a waste collection container, and a waste transfer pump connected in communication with said waste collection container and said holding reservoir;
   f) a waste transfer conduit connected to said waste transfer pump; and
   g) a dripless, quick-disconnect connector, said connector being configured and disposed to selectively render said waste collection container in communication with said waste transfer pump via said waste transfer conduit, said connector being further configured so as to be automatically open when said waste collection container is disposed to receive waste and automatically sealed when said waste collection container is being transported to a waste disposal site.

7. An apparatus for managing waste arising from at least one of the care, maintenance, and treatment of a patient, the apparatus comprising:

a) means for supporting at least a portion of the patient's body;
b) means for catching waste, said waste catching means being carried by said supporting means;
c) a vacuum blower disposed for sucking the wastes from said catching means;
d) a holding reservoir disposed in communication with said catching means and said vacuum blower to receive the waste sucked from said catching means by said vacuum blower, wherein:
e) means for cleansing said catching means, said cleansing means including a rinse solution container, a rinse solution nozzle, and a rinse solution pump connected in communication with said rinse solution container and said rinse solution nozzle;
f) a rinse solution conduit connected to said rinse solution nozzle; and
g) a dripless, quick-disconnect connector, said connector being configured and disposed to render said solution container in communication with said rinse solution nozzle via said rinse solution conduit, said connector being further configured so as to be automatically open when said rinse solution container is disposed in communication with said rinse solution pump and automatically sealed when said rinse solution container is disengaged from communication with said rinse solution pump.

8. An apparatus for managing waste arising from at least one of the care, maintenance, and treatment of a patient, the apparatus comprising:
a) means for supporting at least a portion of the patient's body;
b) means for catching waste, said waste catching means being carried by said supporting means;
c) a vacuum blower disposed for sucking the wastes from said catching means;
d) a holding reservoir disposed in communication with said catching means and said vacuum blower to receive the waste sucked from said catching means by said vacuum blower; and
e) means for adapting the waste managing means to be carried by a patient support system, said adapting means including at least one inflatable U-shaped cushion configured and disposed for receiving at least a portion of said patient body portion supporting means.

9. An apparatus for managing waste arising from at least one of the care, maintenance, and treatment of a patient, the apparatus comprising:
a) means for supporting at least a portion of the patient's body;
b) means for catching waste, said waste catching means being carried by said supporting means;
c) a vacuum blower disposed for sucking the wastes from said catching means;
d) a holding reservoir disposed in communication with said catching means and said vacuum blower to receive the waste sucked from said catching means by said vacuum blower; and
e) means for turning the patient to facilitate cleansing of waste, said turning means being disposed adjacent said patient body portion supporting means.

10. An apparatus as in claim 9, wherein:
said turning means includes at least one turning sack and a pair of air flow diverter valves disposed for selective communication with said turning sack.

11. An apparatus as in claim 9, further comprising:
means for preventing operation of said turning means unless at least one predetermined safety condition has been met.

12. An apparatus for managing waste arising from at least one of the care, maintenance, and treatment of a patient, the apparatus comprising:
a) means for supporting at least a portion of the patient's body;
b) means for catching waste, said waste catching means being carried by said supporting means;
c) a vacuum blower disposed for sucking the wastes from said catching means;
d) a holding reservoir disposed in communication with said catching means and said vacuum blower to receive the waste sucked from said catching means by said vacuum blower; and
e) means for counting the number of events producing waste caught by said catching means.

13. An apparatus for managing waste arising from at least one of the care, maintenance, and treatment of a patient, the apparatus comprising:
a) means for supporting at least a portion of the patient's body;
b) means for catching waste, said waste catching means being carried by said supporting means;
c) a vacuum blower disposed for sucking the wastes from said catching means;
d) a holding reservoir disposed in communication with said catching means and said vacuum blower to receive the waste sucked from said catching means by said vacuum blower;
e) means for detecting and signaling the presence of liquid waste, said detecting and signaling means being disposed downstream of said catching means, wherein:
   i) said detecting and signaling means including a pair of electrically conducting elements,
   ii) each said element being separated by a small predetermined distance from each other said element in said pair,
   iii) said detecting and signaling means further including an electrical circuit including said pair of elements and a signaling mechanism for emitting a signal, and
   iv) wherein moisture flowing between said pair of elements forms an electrical connection between said elements and completes said electrical circuit containing said signaling mechanism for emitting a signal in response to detecting such moisture; and
f) means for controlling operation of said vacuum blower responsive to moisture detection by said detecting and signaling means, said control means being connected in communication with said vacuum blower and to said detecting and signaling means.

14. An apparatus for managing waste from the treatment and/or care and maintenance of a patient who is supported at least as to a first portion of the patient's body on a support surface of a patient support system, the apparatus comprising:
a) means for supporting at least a second portion of the body of the patient, said second patient body portion supporting means defining an inflatable first surface configured and disposed substantially coextensive with the support surface of the patient support system; and
b) means for catching waste, i) said waste catching means being supported by said second patient body portion supporting means so as to be disposed between the patient and said second patient body portion supporting means;

c) means for removing the waste from said catching means, said removing means being disposed in communication with said catching means; and d) means for collecting the waste removed from said catching means by said removing means, said collecting means being disposed in communication with said removing means, wherein said collecting means includes:
   i) a collection container connected in communication with said removing means, and
   ii) said collection container having an opening configured so as to be removably securable to the patient support system and automatically open when secured to the patient support system and automatically sealed when unsecured to the patient support system.

15. An apparatus as in claim 14, wherein:
f) said collecting means further includes:
   i) a pump for transferring waste from said removing means to said collection container.

16. An apparatus as in claim 14, further comprising:
f) means for detecting a predetermined level of liquid waste inside said waste collection container and providing a signal upon detecting same, said liquid waste level detecting means including:
   i) a liquid sensor element having a portion disposed for detecting a predetermined level of liquid inside said waste collection container, and
   ii) a means for emitting a signal in response to said sensor detecting said predetermined level of liquid in said collection container.

17. An apparatus for managing waste from the treatment and/or care and maintenance of a patient who is supported at least as to a first portion of the patient's body on a support surface of a patient support system, the apparatus comprising:

a) means for supporting at least a second portion of the body of the patient, said second patient body portion supporting means defining an inflatable first surface configured and disposed substantially coextensive with the support surface of the patient support system;

b) means for catching waste,
   i) said waste catching means being supported by said second patient body portion supporting means so as to be disposed between the patient and said second patient body portion supporting means;

c) means for removing the waste from said catching means, said removing means being disposed in communication with said catching means;

d) means for collecting the waste removed from said catching means by said removing means, said collecting means being disposed in communication with said removing means, said collecting means including:
   i) a collection container connected in communication with said removing means, and
   ii) said collection container having an opening configured so as to be removably securable to the patient support system and automatically open when secured to the patient support system and automatically sealed when unsecured to the patient support system;

e) means for detecting a predetermined level of liquid waste inside said waste collection container and providing a signal upon detecting same, said liquid waste level detecting means including:
   i) a liquid sensor element having a portion disposed for detecting a predetermined level of liquid inside said waste collection container, and
   ii) a means for emitting a signal in response to said sensor detecting said predetermined level of liquid in said collection container; and f) a second housing configured for receiving said waste collection container,
   i) said second housing including a means for connecting said collection container in communication with said holding reservoir,
   ii) wherein said connecting means is automatically engagable with said collection container when said second housing receives said collection container,
   iii) wherein said connecting means is configured to prevent waste from escaping when said connecting means is disengaged from said collection container,
   iv) said second housing further including a means for coupling said liquid level sensor element in communication with said signal emitting means, and
   v) wherein said coupling means is automatically engagable when said second housing receives said collection container.

18. An apparatus for managing waste from the treatment and/or care and maintenance of a patient who is supported at least as to a first portion of the patient's body on a support surface of a patient support system, the apparatus comprising:

a) means for supporting at least a second portion of the body of the patient, said second patient body portion supporting means defining an inflatable first surface configured and disposed substantially coextensive with the support surface of the patient support system;

b) means for catching waste,
   i) said waste catching means being supported by said second patient body portion supporting means so as to be disposed between the patient and said second patient body portion supporting means;

c) means for removing the waste from said catching means, said removing means being disposed in communication with said catching means;

d) means for collecting the waste removed from said catching means by said removing means, said collecting means being disposed in communication with said removing means; and e) means for detecting and signaling the presence of liquid waste, said detecting and signaling means being in communication with at least one of said catching means, said removing means, and said collecting means.

19. An apparatus for managing waste from the treatment and/or care and maintenance of a patient who is supported at least as to a first portion of the patient's body on a support surface of a patient support system, the apparatus comprising:

a) means for supporting at least a second portion of the body of the patient, said second patient body portion supporting means defining an inflatable first surface configured and disposed substantially coextensive with the support surface of the patient support system;

b) means for catching waste,
  i) said waste catching means being supported by said second patient body portion supporting means so as to be disposed between the patient and said second patient body portion supporting means; and c) means for removing the waste from said catching means, said removing means being disposed in communication with said catching means, said removing means including:
  i) at least one waste removal conduit connected in communication with said catching means,
  ii) a holding reservoir connected to said waste removal conduit,
  iii) a vacuum blower disposed for creating a suction force in said waste removal conduit,
  iv) means for controlling odor, and
  v) said odor control means being disposed between said holding reservoir and said vacuum blower so that said vacuum blower communicates with said holding reservoir via said odor control means.

20. An apparatus for managing waste from the treatment and/or care and maintenance of a patient who is supported at least as to a first portion of the patient's body on a support surface of a patient support system, the apparatus comprising:

a) means for supporting at least a second portion of the body of the patient, said second patient body portion supporting means defining an inflatable first surface configured and disposed substantially coextensive with the support surface of the patient support system;

b) means for catching waste,
  i) said waste catching means being supported by said second patient body portion supporting means so as to be disposed between the patient and said second patient body portion supporting means;

c) means for removing the waste from said catching means, said removing means being disposed in communication with said catching means, said removing means including:
  i) at least one waste removal conduit connected in communication with said catching means,
  ii) a holding reservoir connected to said waste removal conduit, and
  iii) a vacuum blower disposed for creating a suction force in said waste removal conduit,
  iv) said vacuum blower being connected in communication with said holding reservoir; and
  v) a vacuum wand selectively connected in communication with said holding reservoir wherein said vacuum blower can create a suction force in said vacuum wand.

21. An apparatus as in claim 20, wherein:
h) said removing means further includes:
  i) a rinse solution conduit having one end carried by said vacuum wand,
  ii) a rinse solution container configured to be removably securable to the patient support system and connected for communicating with said rinse solution conduit, and
  iii) a rinse pump connected for pumping rinse solution from said rinse solution container through said rinse solution conduit to be dispensed via said vacuum wand.

22. An apparatus as in claim 21, further comprising:
h) means for activating operation of said rinse pump responsive to operator access to said vacuum wand.

23. An apparatus as in claim 21, further comprising:
f) means for detecting a predetermined level of liquid in said rinse solution container and providing a signal upon detecting same, said rinse solution level detecting means including:
  i) a liquid sensor element having a portion disposed for detecting a predetermined level of rinse liquid inside said rinse solution container, and
  ii) a means for emitting a signal in response to said sensor element detecting said predetermined level of liquid in said rinse solution container.

24. An apparatus as in claim 23, further comprising:
f) a first housing con for receiving said rinse solution container,
  i) said first housing including a means for connecting said rinse solution container in communication with said vacuum wand,
  ii) wherein said connecting means is automatically engagable with said rinse solution container when said first housing receives said rinse solution container,
  iii) wherein said connecting means is configured to prevent rinse solution from escaping when said connecting means is disengaged from said rinse solution container,
  iv) said first housing further including a means for coupling said liquid level sensor element in communication with said signal emitting means, and
  v) wherein said coupling means is automatically engagable when said first housing receives said rinse solution container.

25. Apparatus for managing waste from the care and/or treatment of a patient, the apparatus comprising:
a) means for supporting at least a portion of the patient's body at less than capillary closure pressures; and
b) means for receiving, removing and collecting for disposal, waste from events associated with care and/or treatment of the patient supported by said patient body portion supporting means, independent of active cooperation of the patient prior to the occurrence of the event, independent of prepositioning the excretory organs of the patient over an enlarged opening defined through said patient body portion supporting means, independent of active cooperation of the hospital staff prior to the occurrence of the care and/or treatment event, independent of movement of any section of said patient body portion supporting means prior to the occurrence of the event.

26. An apparatus for supporting a patient in the presence of at least one liquid associated with the treatment and/or care and maintenance of a patient, the apparatus comprising:
a) a support member configured to contain pressurized air,
  i) said support member defining a base portion and a plurality of discrete, elongated, inflatable, cylindrical support fingers extending upwardly from said base portion to define their lengths thereof and disposed adjacent to each other and separated from each other along their lengths thereof when inflated, ii) each said support finger having a free end defining a patient support surface at the end of its length opposite the end extending from said base portion, said patient support surfaces being disposed to support the weight of at least a portion of the patient's body, and iii) said base portion of said support member further defining a drain opening extending through said base portion and configured to receive a drain conduit passing between said support fingers.

27. An apparatus as in claim 26, wherein said support member further includes:

iii) an air permeable foam member disposed inside said support member and beneath said plurality of discrete support fingers.

28. An apparatus as in claim 27, wherein said support member further defines:

iv) a drain opening and a floor configured to slope toward said drain opening; and v) said foam member is configured to conform to and rest against said floor of said support member and is further configured with an opening in registry with said drain opening of said support member.

29. An apparatus as in claim 26, wherein said support member further defines:

iii) a drain opening; and iv) a floor configured to slope toward said drain opening.

30. An apparatus for supporting a patient in the presence of at least one liquid associated with the treatment and/or care and maintenance of a patient, the apparatus comprising:

a) a support member configured to contain pressurized air, i) said support member defining a plurality of discrete, elongated, cylindrical support fingers disposed adjacent to each other and separated from each other, ii) each said support finger having a free end defining a patient support surface, said patient support surfaces being disposed to support the weight of at least a portion of the patient's body; and b) a liquid impermeable basin member, i) said basin member being configured to conform to and receive a plurality of at least said free ends of said support fingers of said support member, ii) said basin member being further configured with a floor disposed beneath the level of said support surfaces of said support fingers when said basin member is fitted over said support member and receives said support fingers, iii) said basin member being further configured with at least one drain opening defined through said floor, and iv) said floor being configured so as to slope toward said at least one drain opening.

31. An apparatus as in claim 30, further comprising:

c) a liquid permeable filter sheet disposed to be carried atop said basin member by the portions of said basin member conforming to said support surfaces of said support fingers of said support member.

32. An apparatus as in claim 30, wherein:

v) said basin member defines a plurality of grid configurations, vi) each said grid configuration being disposed over one of said support surfaces of one of said support fingers of said support member, and vii) each said grid configuration defining a plurality of slightly raised portions and a plurality of recessed channel portions separated from one another by said raised portions.

33. An apparatus as in claim 32, further comprising:

c) a liquid permeable filter sheet disposed atop said basin member, said sheet defining a plurality of liquid openings which render said filter sheet liquid permeable; and wherein:

viii) said channel portions of said grid configurations being wider than said liquid openings which render said filter sheet liquid permeable.

34. Apparatus for receiving and containing liquid associated with the treatment and/or care and maintenance of a patient, the apparatus comprising:

a) a housing defining a receptacle configured for receiving a container;

b) a liquid impermeable container having an exterior portion configured and disposed to engage said receptacle of said housing, said container further defining an opening;

c) a conduit mounted to said housing;

d) means for selectively, detachably connecting said conduit to said container opening, said connecting means being configured so as to automatically open a flow path between said conduit and said container when said container is connected to said conduit and automatically close said flow path when said container is disconnected from said conduit.

35. An apparatus as in claim 34, further comprising:

e) means for detecting a predetermined level of liquid in said container.

36. An apparatus as in claim 34, further comprising:

e) means for disconnecting said connecting means, said disconnecting means being remotely actuatable from said connecting means and including a spring actuated cam mechanism, an arm and a push rod, said push rod being pivotally connected to said arm, said arm being connected and disposed in communication with said cam mechanism.

37. A method for managing waste arising from at least one of the care, maintenance, and treatment of a patient, the method comprising:

a) supporting at least a portion of the patient's body on the top surfaces of a plurality of pressure-relieving fingers, each finger defining an elongated gas inflatable cylinder formed of a flexible material and filled with pressurized gas;

b) catching waste arising from events associated with at least one of the care, treatment, and bodily functions of the patient;

c) using a vacuum force and gravity to transfer the caught fluid wastes away from the immediate environment of the patient; and d) containing the transferred fluid waste in a portable waste collection container that automatically remains open when disposed to receive waste and automatically seals itself upon being removed from the disposition for receiving waste and remains sealed when being transported to a waste disposal site.

38. A method as in claim 37, wherein:

a) said step of catching waste, includes the step of using a fluid permeable filter sheet to catch particulate wastes that are too large to pass through the filter sheet.

39. A method as in claim 37, further comprising:
a) using a liquid sensor to trigger activation of the vacuum force that transfers the caught fluid wastes away from the immediate environment of the patient.

40. A patient support apparatus comprising:
a frame;
a support surface conforming to at least a first portion of the patient's body for supporting the patient above said frame;
means for managing waste associated with a patient who is supported at least in part on said support surface, said waste managing means being carried by said frame and including:
  i) means for supporting at least a second portion of the patient coextensive with said support surface, and
  ii) means for catching the waste associated with the patient,
    A) said catching means being supported by said second portion supporting means between the patient and said second portion supporting means; and
means for adapting said waste managing means to be carried by said frame, said adapting means being supported by said frame and configured for receiving said second portion supporting means, wherein said adapting means includes:
  i) an adaptor shell, said adaptor shell defining:
    A) a bottom surface configured for being carried by said frame, and
    B) a generally centrally located receiving opening, said receiving opening being defined with a configuration for securingly receiving said waste managing means such that said second portion supporting means is disposed substantially coplanar with said support surface.

41. An apparatus as in claim 40, wherein:
C) at least a first section of said adaptor shell is configured to be inflatable with a gas.

42. An apparatus as in claim 40, wherein:
C) said adaptor shell defines a peripheral wall extending from said bottom surface and disposed surrounding said receiving opening.

43. A patient support apparatus comprising:
a) a frame;
b) a support surface conforming to at least a first portion of the patient's body for supporting the patient above said frame;
c) means for managing waste associated with a patient who is supported at least in part on said support surface, said waste managing means being carried by said frame and including:
  i) means for supporting at least a second portion of the patient coextensive with said support surface, and
  ii) means for catching the waste associated with the patient, said catching means being supported by said second portion supporting means between the patient and said second portion supporting means,
  iii) means for removing the waste from said catching means, said removing means being disposed in communication with said catching means, said removing means including a holding reservoir and a vacuum blower, said vacuum blower being connected in communication with said holding reservoir, said removing means including a vacuum wand selectively connected in communication with said holding reservoir wherein said vacuum blower can create a suction force in said vacuum wand, said removing means including a rinse solution conduit having one end carried by said vacuum wand, said removing means including a rinse solution container configured to be removably securable to said frame and connected for communicating with said rinse solution conduit, and said removing means including a rinse pump connected for pumping rinse solution from said rinse solution container through said rinse solution conduit to be dispensed via said vacuum wand;
d) means for detecting a predetermined level of liquid in said rinse solution container and providing a signal upon detecting same, said rinse solution level detecting means including:
  i) a liquid sensor element having a portion disposed for detecting a predetermined level of rinse liquid inside said rinse solution container, and
  ii) a means for emitting a signal in response to said sensor element detecting said predetermined level of liquid in said rinse solution container;
e) a first housing configured for receiving said rinse solution container,
  i) said first housing including a means for connecting said rinse solution container in communication with said vacuum wand,
  ii) wherein said connecting means is automatically engagable with said rinse solution container when said first housing receives said rinse solution container,
  iii) wherein said connecting means is configured to prevent rinse solution from escaping when said connecting means is disengaged from said rinse solution container,
  iv) said first housing further including a means for coupling said liquid level sensor element in communication with said signal emitting means, and
  v) wherein said coupling means is automatically engagable when said first housing receives said rinse solution container.

44. An apparatus as in claim 43, wherein:
said first housing is carried by said frame.

45. An apparatus as in claim 43, further comprising:
a service cart, said first housing being carried by said service cart.

46. A patient support apparatus, comprising:
a frame;
a support surface conforming to at least a first portion of the patient's body for supporting the patient above said frame; and
means for managing waste associated with a patient who is supported at least in part on said support surface, said waste managing means being carried by said frame and including:
  i) means for supporting at least a second portion of the patient coextensive with said support surface,
  ii) means for catching the waste associated with the patient, said catching means being supported by said second portion supporting means between the patient and said second portion supporting means, iii) means for removing the waste from said catching means, said removing means being disposed in communication with said catching means, and iv) means for collecting the waste removed from said catching means by said removing means, said waste collecting means being disposed in communication with said removing means.

47. An apparatus as in claim 46, wherein:

d) said collecting means includes:
   i) a collection container connected in communication with said removing means, and
   ii) said collection container having an opening configured so as to be removably securable to said frame and automatically open when secured to said frame and automatically sealed when unsecured to said frame.

48. An apparatus as in claim 47, wherein:

e) said collecting means further includes:
   i) a pump for transferring waste from said removing means to said collection container.

49. An apparatus as in claim 47, further comprising:

f) means for detecting a predetermined level of liquid waste inside said waste collection container and providing a signal upon detecting same, said liquid waste level detecting means including:
   i) a liquid sensor element having a portion disposed for detecting a predetermined level of liquid inside said waste collection container, and
   ii) a means for emitting a signal in response to said sensor detecting said predetermined level of liquid in said collection container.

50. An apparatus as in claim 49, further comprising:

g) a second housing configured for receiving said waste collection container,
   i) said second housing including a means for connecting said collection container in communication with said removing means,
   ii) wherein said connecting means is automatically engagable with said collection container when said second housing receives said collection container,
   iii) wherein said connecting means is configured to prevent waste from escaping when said connecting means is disengaged from said collection container,
   iv) said second housing further including a means for coupling said liquid level sensor element in communication with said signal emitting means, and
   v) wherein said coupling means is automatically engagable when said second housing receives said collection container.

51. An apparatus as in claim 46, further comprising:

e) means for detecting and signaling the presence of liquid waste, said liquid waste detecting and signaling means being in communication with at least one of said catching means, said removing means, and said collecting means.

52. A patient support apparatus, comprising:

a) a frame;

b) a support surface conforming to at least a first portion of the patient's body for supporting the patient above said frame;

c) means for managing waste associated with a patient who is supported at least in part on said support surface, said waste managing means being carried by said frame and including:
   i) means for supporting at least a second portion of the patient coextensive with said support surface, and
   ii) means for catching the waste associated with the patient, said catching means being supported by said second portion supporting means between the patient and said second portion supporting means; and d) means for automatically partially turning the patient to facilitate cleansing after a waste-producing event, said turning means being carried by said frame.

53. A patient support apparatus, comprising:

a) a frame;

b) a plurality of low air loss sacks,
   i) said sacks being carried by said frame,
   ii) said sacks being configured to be connected in communication with a source of pressurized gas and configured to be inflatable with pressurized gas, and
   iii) said sacks being configured to define a low air loss support surface conforming to at least a first portion of the patient's body for supporting the patient above said frame when said sacks are inflated with pressurized gas;

c) means for managing waste associated with a patient who is supported at least in part on said low air loss support surface, said waste managing means including:
   i) means for supporting at least a second portion of the patient coextensive with said low air loss support surface of said sacks, and
   ii) means for catching the waste associated with the patient,
   said catching means being supported by said second portion supporting means between the patient and said second portion supporting means; and d) means for adapting said waste managing means to be carried by said frame, said adapting means being supported by said frame and configured for receiving said second portion supporting means, wherein said adapting means includes:
   i) an adaptor shell, said adaptor shell defining:
      A) a bottom surface configured for being carried by said frame, and
      B) a generally centrally located receiving opening, said receiving opening being defined with a configuration for securingly receiving said waste managing means such that said second portion supporting means is disposed substantially coplanar with said low air loss support surface defined by said sacks.

54. An apparatus as in claim 53, wherein:

C) at least a first section of said adaptor shell is configured to be inflatable with a gas.

55. An apparatus as in claim 53, wherein:

C) said adaptor shell defines a peripheral wall extending from said bottom surface and disposed surrounding said receiving opening.

56. A low air loss patient support apparatus, comprising:

a) a frame;

b) a plurality of low air loss sacks,
   i) said sacks being carried by said frame,
   ii) said sacks being configured to be connected in communication with a source of pressurized gas and configured to be inflatable with pressurized gas, and iii) said sacks being configured to define a low air loss support surface conforming to at least a first portion of the patient's body for supporting the patient above said frame when said sacks are inflated with pressurized gas; and c) means for managing waste associated with a patient who is supported at least in part on said low air loss support surface, said waste managing means including:

i) means for supporting at least a second portion of the patient coextensive with said low air loss support surface of said sacks, and ii) means for catching the waste associated with the patient, A) said catching means being supported by said second portion supporting means between the patient and said second portion supporting means; and d) means for automatically partially turning the patient to facilitate cleansing after a waste-producing event, said turning means being carried by said frame.

57. An apparatus for managing waste arising from at least one of the care, maintenance, and treatment of a patient, the apparatus comprising:

a) means for catching the waste arising from at least one of the care, maintenance, and treatment of the patient, said waste catching means including a flexible basin member, i) said basin member defining an upper surface disposed to receive the waste arising from at least one of the care, maintenance, and treatment of the patient, said upper surface being configured with a floor and a plurality of discrete, elongated, hollow, cylindrical support fingers extending upwardly from said floor to define their lengths thereof and disposed adjacent to each other and separated from each other along their lengths thereof, ii) each said support finger having a free end defining a patient support surface at the end of its length opposite the end extending from said floor, iii) said basin member being further configured with at least one drain opening defined through said upper surface at a level beneath said patient support surface, and iv) said floor being configured so as to slope toward said at least one drain opening and intersect said fingers so as to angularly truncate said cylinders.

58. An apparatus as in claim 57, further comprising:
b) a liquid impermeable coating disposed to cover said upper surface of said basin member and render said basin member liquid impermeable.

59. An apparatus as in claim 58, wherein said coating includes polyurethane and silicone.

60. An apparatus as in claim 58, wherein said coating includes an antimicrobial composition.

61. An apparatus for managing waste arising from events connected with at least one of the care, maintenance, and treatment of a patient, which waste includes moisture, the apparatus comprising:

a) means for catching waste arising from at lest one of the care, maintenance, and treatment of a patient;

b) a vacuum blower disposed for sucking the wastes from said catching means;

c) a holding reservoir disposed in communication with said catching means and said vacuum blower to receive the waste sucked from said catching means; and d) means for detecting the presence of moisture arising from events connected with at least one of the care, maintenance, and treatment of the patient before the moisture reaches said holding reservoir.

62. An apparatus as in claim 61, wherein said moisture detecting means includes:

a pair of electrically conducting rings disposed in the path to be travelled by moisture sucked from said catching means on the way to said holding reservoir.

63. An apparatus as in claim 61, further comprising:
e) means for signaling the detection of moisture, said signaling means being connected in communication with said moisture detecting means.

64. An apparatus as in claim 63, wherein said means for signaling the detection of moisture includes a lighted indicator.

65. An apparatus as in claim 61, further comprising:
e) means for counting the number of waste producing events that occur during a given period of time, said waste event counting means being connected in communication with said moisture detecting means.

66. An apparatus as in claim 65, wherein said moisture detecting means is configured to send signals to said waste event counting means when said moisture detecting means detects moisture, and said waste event counting means includes a controller that is programmed to keep track of the signals received from said moisture detecting means during a given interval of time.

67. An apparatus for managing waste arising from events connected with at least one of the care, maintenance, and treatment of a patient, which waste includes moisture, the apparatus comprising:

a) means for catching waste arising from at least one of the care, maintenance, and treatment of a patient;

b) a vacuum blower disposed for sucking the wastes from said catching means; and c) means for controlling odor, said odor control means being connected in communication with said vacuum blower.

68. An apparatus as in claim 67, wherein said vacuum blower is disposed between said catching means and said odor control means so that the exhaust from said vacuum blower communicates with the surrounding atmosphere via said odor control means.

69. An apparatus as in claim 67, wherein said odor control means includes an odor filter having activated charcoal.

70. An apparatus for managing waste arising from events connected with at least one of the care, maintenance, and treatment of a patient, which waste includes moisture, the apparatus comprising:

a) a frame;

b) means for catching waste arising from at least one of the care, maintenance, and treatment of a patient, said catching means being carried by said frame;

c) means for collecting the waste received by said catching means, said collecting means being removably securable in communication with said catching means;
d) a housing carried by said frame and configured for removably receiving and securing said collecting means; and
e) wherein said collecting means includes a waste jug,
  i) said waste jug defining an enclosed container configured with a handle for manual portability, and
  ii) said waste jug being further configured with a translucent portion and graduations defined in said translucent portion.

71. An apparatus as in claim 70, wherein said waste jug includes an opening and a self-closing inlet/outlet valve disposed in said opening and configured so as to be removably securable to said housing and automatically open when secured to said housing and automatically sealed when unsecured from said housing.

72. An apparatus for managing waste arising from at least one of the care, maintenance, and treatment of a patient, the apparatus comprising:
a) a means for supporting at least a portion of the patient's body, said supporting means including a flexible member inflatable with pressurized air, said flexible member including a plurality of flexible surfaces forming in combination a discontinuous surface for receiving said portion of the patient's body;
b) a means for catching waste, said waste catching means being carried by said supporting means;
c) a vacuum blower disposed for sucking the wastes from said catching means;
d) a holding reservoir disposed in communication with said catching means and said vacuum blower to receive the waste sucked from said catching means by said vacuum blower;
e) means for cleansing, said cleansing means being connected in communication with said holding reservoir, wherein:
said cleansing means includes a vacuum wand and a diverter valve configured and disposed to selectively connect said vacuum wand in communication with said vacuum blower, said vacuum wand defining a free end with a tip, said tip defining a plurality of safety louvers at the underside surface of the free end thereof.

* * * * *

UNITED STATES PATENT AND TRADEMARK OFFICE
CERTIFICATE OF CORRECTION

PATENT NO. : 5,269,030

DATED : December 14, 1993

INVENTOR(S) : Pahno et al

It is certified that error appears in the above-identified patent and that said Letters Patent is hereby corrected as shown below:

Column 11, line 19: after "FIG. 4", insert --A--.

Column 11, line 65: insert --1-- between "FIG." and "5".

Column 37, line 2: delete "rings" and insert --elements--.

Column 50, line 30: after "a)", insert --a--.

Column 50, line 37: after "b)", insert --a--.

Column 51, line 10: change "," to ";" and delete "wherein:".

Column 51, line 20: between "said" and "solution", insert --rinse--.

Column 53, line 45: delete --an inflatable, insert "a"

Column 54, line 43: after "system;", add --and--.

Column 54, line 52: after "means;" add --and--.

Column 55, line 1: delete --an inflatable, insert "a"

Column 55, line 34, delete --an inflatable, insert "a"

Column 55, line 44: after "means;" add --and--.

Column 56, line 21: after "con" add --figured--.

Column 59, line 8: between "apparatus" and "comprising" insert --,--.

UNITED STATES PATENT AND TRADEMARK OFFICE
CERTIFICATE OF CORRECTION

PATENT NO. : 5,269,030

DATED : December 14, 1993

INVENTOR(S) : Pahno et al

It is certified that error appears in the above-identified patent and that said Letters Patent is hereby corrected as shown below:

Column 59, line 47: between "apparatus" and "comprising", insert --,--.

Column 60, line 53: before "a frame;" insert --(a)--.

Column 60, line 54: before "a support", insert (b)--.

Column 60, line 57: before "means for", insert --(c)--.

Column 62, line 13: between "A" and "patient", insert --low air loss--.

Column 63, line 67: change "lest" to read --least--.

Signed and Sealed this

Twenty-first Day of June, 1994

*Attest:*

BRUCE LEHMAN

*Attesting Officer*   *Commissioner of Patents and Trademarks*